(12) United States Patent
Kramer et al.

(10) Patent No.: US 10,898,569 B2
(45) Date of Patent: Jan. 26, 2021

(54) TREATMENT OF PEANUT ALLERGY

(71) Applicant: ALLERGY THERAPEUTICS (UK) LIMITED, Worthing (GB)

(72) Inventors: Matthias F. Kramer, Worthing (GB); Andris Zeltins, Riga (LV); Murray A. Skinner, Worthing (GB); Matthew D. Heath, Worthing (GB)

(73) Assignee: ALLERGY THERAPEUTICS (UK) LIMITED, Worthing (GB)

( * ) Notice: Subject to any disclaimer, the term of this patent is extended or adjusted under 35 U.S.C. 154(b) by 0 days.

(21) Appl. No.: 16/097,182

(22) PCT Filed: Apr. 26, 2017

(86) PCT No.: PCT/EP2017/059965
§ 371 (c)(1),
(2) Date: Oct. 26, 2018

(87) PCT Pub. No.: WO2017/186808
PCT Pub. Date: Nov. 2, 2017

(65) Prior Publication Data
US 2019/0134189 A1 May 9, 2019

(30) Foreign Application Priority Data
Apr. 27, 2016 (EP) .................................... 16167298

(51) Int. Cl.
*A61K 39/35* (2006.01)
*A61K 39/00* (2006.01)

(52) U.S. Cl.
CPC ...... *A61K 39/35* (2013.01); *A61K 2039/5258* (2013.01); *A61K 2039/577* (2013.01); *A61K 2039/60* (2013.01); *A61K 2039/6075* (2013.01); *C12N 2770/14023* (2013.01); *C12N 2770/14034* (2013.01); *C12N 2770/14041* (2013.01); *C12N 2770/14042* (2013.01)

(58) Field of Classification Search
None
See application file for complete search history.

(56) References Cited

U.S. PATENT DOCUMENTS

2006/0251623 A1* 11/2006 Bachmann ............. A61K 39/00 424/93.2
2011/0229523 A1* 9/2011 Koppelman ........... A61K 39/35 424/275.1
2017/0312371 A1* 11/2017 Bachmann ......... A61K 39/0007

FOREIGN PATENT DOCUMENTS

WO  WO 2005/100995 A2   10/2005
WO  WO 2016/062720 A1   4/2016

OTHER PUBLICATIONS

Lazdina et al. Priming of cytotoxic T cell responses to exogenous hepatitis B virus core antigen is B cell dependent. Journal of General Virology (2003), 84, 139-146.*
Nuzzaci et al. Structural and biological properties of Cucumber mosaic virus particles carrying hepatitis C virus-derived epitopes. Journal of Virological Methods 155 (2009) 118-121.*
Natilla et al. Cucumber mosaic virus as carrier of a hepatitis C virus-derived epitope. Arch Virol (2004) 149: 137-154.*
Frasca et al. Antibody-Selected Mimics of Hepatitis C Virus Hypervariable Region 1 Activate Both Primary and Memory Th Lymphocytes. Hepatology 2003;38:653-663.*
GenBank: AAQ82699.1. coat protein [Cucumber mosaic virus]. Sep. 22, 2013.*
Nuzzaci et al., "Structural and biological properties of Cucumber mosaic virus particles carrying hepatitis C virus-derived epitopes," *J Virol Meth* 155(2):118-121 (2009).
Schmitz et al. "Displaying Fel d1 on virus-like particles prevents reactogenicity despite greatly enhanced immunogenicity: a novel therapy for cat allergy," *J Exp Med* 206(9):1941-1955 (2009).
International Search Report for PCT/EP2017/059965, dated Jun. 26, 2017.

* cited by examiner

*Primary Examiner* — Nianxiang Zou
(74) *Attorney, Agent, or Firm* — Medler Ferro Woodhouse & Mills PLLC

(57) ABSTRACT

The present invention relates to compositions, immunogenic or vaccine compositions and pharmaceutical compositions for the prevention or treatment of peanut allergy in humans. Furthermore, the invention provides methods for preventing or treating of peanut allergy in humans.

20 Claims, 19 Drawing Sheets
Specification includes a Sequence Listing.

Su Ft w1 w2 w3 w4 E30 E30* M catATGaatcataaagtgcgccagcagtgggaactgcagggcgatcgtcgctgccagagccagctggaacgc
gcgaacctgcgtccgtgcgaacagcatctgatgcagaaaattcagcgcgatgaagatagctatggccgcgatcc
gtatagcccaagccaagatccgtatagcccaagccaggatccggatcgccgtgatccgtatagcccaagcccgt
atgatcgtcgcggcgcgggcagcagccagcatcaggaacgctgctgcaacgaactgaacgaatttgaaaaca
accagcgctgcatgtgcgaagcgctgcaacagattatggaaaaccagagcgatcgcctgcaaggccgccagc
aagaacagcagtttaaacgcgaactgcgtaacctgccgcagcagtgcggcctgcgtgcgccgcagcgctgcga
tctggaagtggaaagcggcggccgtgatcgctatggtggttgtggaTAATAAgcttctcgag

FIG. 11B

MNHKVRQQWELQGDRRCQSQLERANLRPCEQHLMQKIQRDEDSYGRDPYSPSQDPYSPSQDPD
RRDPYSPSPYDRRGAGSSQHQERCCNELNEFENNQRCMCEALQQIMENQSDRLQGRQQEQQFK
RELRNLPQQCGLRAPQRCDLEVESGGRDRYGGCG

FIG. 11C

TREATMENT OF PEANUT ALLERGY

The present invention relates to compositions, immunogenic or vaccine compositions and pharmaceutical compositions for the prevention or treatment of peanut allergy in humans. Furthermore, the invention provides methods for preventing or treating of peanut allergy in humans.

RELATED ART

Food allergies are common diseases in Western countries. According to the US Department of Health and Human Services about 5 million Americans present a food allergy with high public cost, probably with increasing prevalence. Especially peanut allergy is a frequent disease affecting all age groups (0.6% of the population in US) but develops often already early in life. In most cases peanut allergy does not resolve with age and is a serious health-treat as small amount of peanut can induce strong allergic reaction (Al-Muhsen, S., Clarke, A. E., and Kagan, R. S. (2003), Canadian Medical Association Journal, 168(10):1279-1285). The high reactogenicity of peanuts (symptoms are caused in affected people with allergy with less than 1 mg ingested peanut) may be also due to an elevated amount of allergen protein in the fruit. One peanut contains about 200 mg of protein. Indeed, the dominant protein species in peanuts are allergens, which is vastly different for most other sources of allergens as e.g. pollen. Peanuts harbor a variety of different antigens. Currently, 17 *Arachis* allergens are suggested (www.allergen.org). The major allergens are Ara h1, Ara h2, Ara h3 and Ara h6. Reports by Burks et al indicated that, in particular, Ara h1 and Ara h2 are recognized by IgE from greater than 95% of peanut-sensitive patients (Burks, W., Sampson, H. A., and Bannon, G. A. (2008) Allergy, 53(8): 725-730). Moreover, Ara h 3 is recognized by about 45% of patients with peanut allergy (Li, X., et al., J Allergy Clin. Immunol. (2000) 106:150-158).

The symptoms of an allergic reaction against peanut vary from itching, cutaneous rash, vomiting, diarrhea, dyspnea to acute anaphylaxis and are mostly caused by IgE. The typical type I allergy pathway is dependent on a T-helper cell type 2 response with production of IL-4 and induction of IgE (Georas, S. N., Guo, J., De Fanis, U., and Casolaro, V. (2005) The European Respiratory Journal, 26(6):1119-1137). Cross-linking to FcεRI-IgE complexes by allergen on circulating basophils and especially tissue resident mast cells induces cellular degranulation with liberation of inflammatory mediators including histamine, prostaglandins and leukotrienes (in case of peanuts when allergens penetrate mucosal barriers of the gastrointestinal tract).

At present most therapies block mast cell effector molecules (antihistamines) or nonspecifically suppress immune response (steroids). For food allergies the widely-used treatment is the elimination of the allergenic food from the diet. Although oral immunotherapy has shown some successes, the procedures remain time consuming and bear a risk for undesired allergic reactions (Yu, G. P., Weldon, B., Neale-May, S., and Nadeau, K. C. (2012) International Archives of Allergy and Immunology, 159(2): 179-182). Hence, there is a need for safe and efficacious treatment of peanut allergies.

SUMMARY OF THE INVENTION

The present invention provides for compositions for the prevention and treatment of peanut allergy in humans. In particular, the present invention provides for compositions and its uses for prevention and treatment of peanut allergy in humans, wherein preferred inventive compositions comprise at least one peanut allergen displayed on virus-like particles of plant virus Cucumber Mosaic Virus (CMV) modified by incorporation of Th cell epitopes, in particular universal Th cell epitopes. Furthermore, these modified VLPs serve as vaccines for generating immune responses, in particular antibody responses, against said at least one peanut allergen. The presence of the Th cell epitopes, in particular universal Th cell epitopes, leads to a further increase in the generated immune response and, thus, the beneficial effect for the prevention and treatment of peanut allergy.

Thus, in a first aspect, the present invention provides for a composition comprising (a) a modified virus-like particle (VLP) with at least one first attachment site, wherein said modified VLP comprises, essentially consists of, or consists of, at least one modified VLP polypeptide, wherein said modified VLP polypeptide comprises, or preferably consists of, a) a VLP polypeptide, and b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%; and (b) at least one peanut allergen with at least one second attachment site, wherein preferably said peanut allergen is selected from the peanut allergens, and isoforms thereof, of Ara h1, Ara h2, Ara h3 and Ara h6 and proteins with an amino acid sequence of at least 90%, preferably of at least 92%, further preferably of at least 95%, and again further preferably of at least 98% amino acid sequence identity with said peanut allergens and isoforms thereof; and wherein further preferably said peanut allergen comprises, or preferably consists of, a protein with the amino sequence selected from SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30, or a protein with an amino acid sequence of at least 90%, preferably of at least 92%, further preferably of at least 95%, and again further preferably of at least 98% amino acid sequence identity with SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30; wherein (a) and (b) are linked through said at least one first and said at least one second attachment site via at least one non-peptide covalent bond.

In a preferred embodiment, said virus-like particle (VLP) is a recombinant VLP. In a further preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, a) a CMV polypeptide, and b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. In a further very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 90% with SEQ ID NO:23. In a further very preferred embodiment, said VLP is a modified VLP of cucumber mosaic virus (CMV), wherein said modified CMV polypeptide comprises, preferably consists of, an amino acid sequence of SEQ ID NO:6 or SEQ ID NO:7.

In a further very preferred embodiment, said at least one peanut allergen comprises, or preferably consists of, a protein with the amino sequence selected from: (a) SEQ ID NO:17; (b) SEQ ID NO:18; (c) SEQ ID NO:19; (d) SEQ ID NO:20, (e) SEQ ID NO:22 or f) SEQ ID NO:30. In a further very preferred embodiment, said at least one peanut allergen comprises, or preferably consists of, a protein with the amino sequence of SEQ ID NO:18, an isoform thereof, or of a protein with an amino acid sequence of at least 90%, preferably of at least 92%, further preferably of at least 95%, and again further preferably of at least 98% amino acid sequence identity with SEQ ID NO:18. In a further very preferred embodiment, said second attachment site is a sulfhydryl group, and wherein preferably said sulfhydryl group is derived from reaction of said at least one peanut allergen with N-succinimidyl S-acetylthioacetate (SATA) or a derivate thereof, preferably with SATA. In a further very preferred embodiment, said second attachment site is a sulfhydryl group, and wherein preferably said sulfhydryl group is derived from reaction of a lysine residue of said at least one peanut allergen.

In a further aspect, the present invention provides for an immunogenic or vaccine composition comprising an effective amount of said composition of the invention, wherein preferably said immunogenic or vaccine composition further comprises an adjuvant.

In a further aspect, the present invention provides for a pharmaceutical composition comprising: (a) the inventive composition or the inventive immunogenic or vaccine composition; and (b) a pharmaceutically acceptable carrier.

In a further aspect, the present invention provides for a method of immunization, wherein said method comprises administering the inventive composition, the inventive immunogenic or vaccine composition or the inventive pharmaceutical composition to human.

In a further aspect, the present invention provides for the inventive composition, the inventive immunogenic or vaccine composition, or the inventive pharmaceutical composition for use as a medicament.

In a further aspect, the present invention provides for the inventive composition, the inventive immunogenic or vaccine composition, or the inventive pharmaceutical composition for use in a method of prevention or treatment of peanut allergy in a human, wherein an effective amount of said inventive composition, said inventive immunogenic or vaccine composition, or said inventive pharmaceutical composition is administered to said human. Preferably, said administration of said inventive composition, said inventive immunogenic or vaccine composition, or said inventive pharmaceutical composition reduces at least one symptom of said peanut allergy when compared to the at least one symptom before said administration.

In a further aspect, the present invention provides for a method of prevention or treatment of peanut allergy in a human, wherein said method comprises administering an effective amount of said inventive composition, said inventive immunogenic or vaccine composition, or said inventive pharmaceutical composition to human.

In another aspect, the present invention provides for the use of said inventive composition, said inventive immunogenic or vaccine composition, or said inventive pharmaceutical composition for the manufacture of a medicament for the prevention or treatment of peanut allergy in a human, wherein typically and preferably an effective amount of said inventive composition, said inventive immunogenic or vaccine composition, or said inventive pharmaceutical composition is administered to human.

In another aspect, the present invention provides a composition for use in a method of preventing or treating peanut allergy in a human, wherein an effective amount of said composition is administered to said human, and wherein said composition comprises (a) a modified virus-like particle (VLP) with at least one first attachment site, wherein said modified VLP comprises, essentially consists of, or consists of, at least one modified VLP polypeptide, wherein said modified VLP polypeptide comprises, or preferably consists of, a) a VLP polypeptide, and b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%; and (b) at least one peanut allergen with at least one second attachment site, wherein preferably said peanut allergen is selected from the peanut allergens, and isoforms thereof, of Ara h1, Ara h2, Ara h3 and Ara h6 and proteins with an amino acid sequence of at least 90%, preferably of at least 92%, further preferably of at least 95%, and again further preferably of at least 98% amino acid sequence identity with said peanut allergens and isoforms thereof; and wherein further preferably said peanut allergen comprises, or preferably consists of, a protein with the amino sequence selected from SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30, or a protein with an amino acid sequence of at least 90%, preferably of at least 92%, further preferably of at least 95%, and again further preferably of at least 98% amino acid sequence identity with SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30; wherein (a) and (b) are linked through said at least one first and said at least one second attachment site via at least one non-peptide covalent bond.

In a further aspect, the present invention provides for a composition comprising (a) a modified virus-like particle (VLP) with at least one first attachment site; (b) at least one peanut allergen with at least one second attachment site, wherein said at least one peanut allergen comprises, or preferably consists of, a protein with the amino sequence of SEQ ID NO:18, an isoform thereof, or of a protein with an amino acid sequence of at least 90%, preferably of at least 92%, further preferably of at least 95%, and again further preferably of at least 98% amino acid sequence identity with SEQ ID NO:18; wherein (a) and (b) are linked through said at least one first and said at least one second attachment site via at least one non-peptide covalent bond. Preferably, said VLP is a modified VLP of cucumber mosaic virus (CMV), wherein said modified CMV polypeptide comprises, preferably consists of, an amino acid sequence of SEQ ID NO:6 or SEQ ID NO:7.

In a further very preferred embodiment, said at least one peanut allergen with at least one second attachment site, wherein said peanut allergen comprises, or preferably consists of, a protein with the amino sequence selected from SEQ ID NO:18, SEQ ID NO:17 or SEQ ID NO:22. In a further very preferred embodiment, said second attachment site is a sulfhydryl group, and wherein preferably said sulfhydryl group is derived from reaction of said at least one peanut allergen with N-succinimidyl S-acetylthioacetate (SATA). In a further very preferred embodiment, said second attachment site is a sulfhydryl group, and wherein preferably said sulfhydryl group is derived from reaction of a lysine residue of said at least one peanut allergen.

Further aspects and embodiments of the present invention will be become apparent as this description continues.

BRIEF DESCRIPTION OF FIGURES

FIG. 3 Mass spectrometric analysis of purified CMV-derived VLPs. Matrix-assisted laser desorption/ionization (MALDI)-TOF MS analysis was carried out on an Autoflex MS (Bruker Daltonik, Germany). The protein molecular mass (MM) calibration standard II (22.3-66.5 kDa; Bruker Daltonik) was used for mass determination.

FIG. 13 Analysis of coupling of Ara-h202-nhk protein to CMV-Ntt830 VLPs.

DETAILED DESCRIPTION OF THE INVENTION

Figure 1:
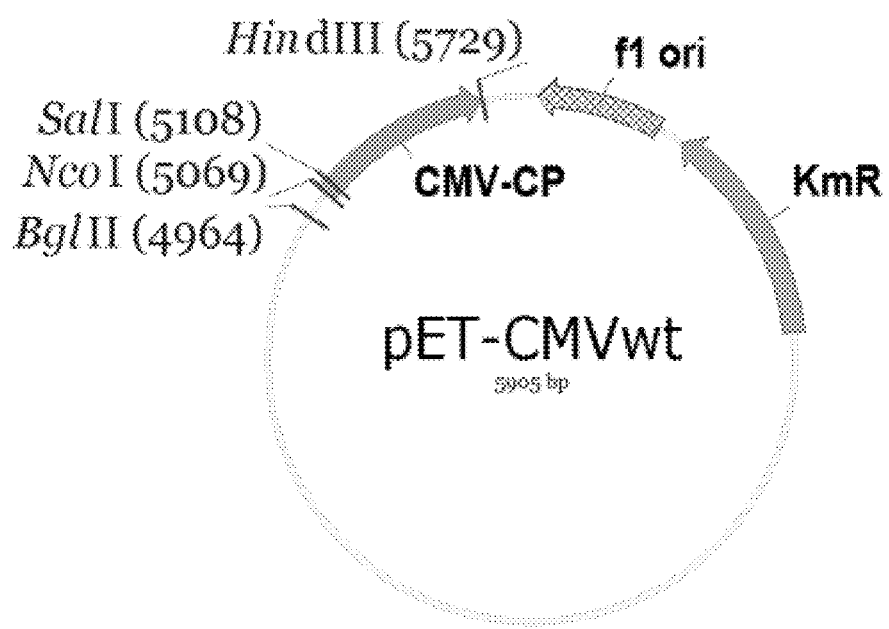
FIG. 1 pET-CMVwt plasmid map. The relative positions of relevant genes and restriction enzyme sites are denoted.
Figure 2A:
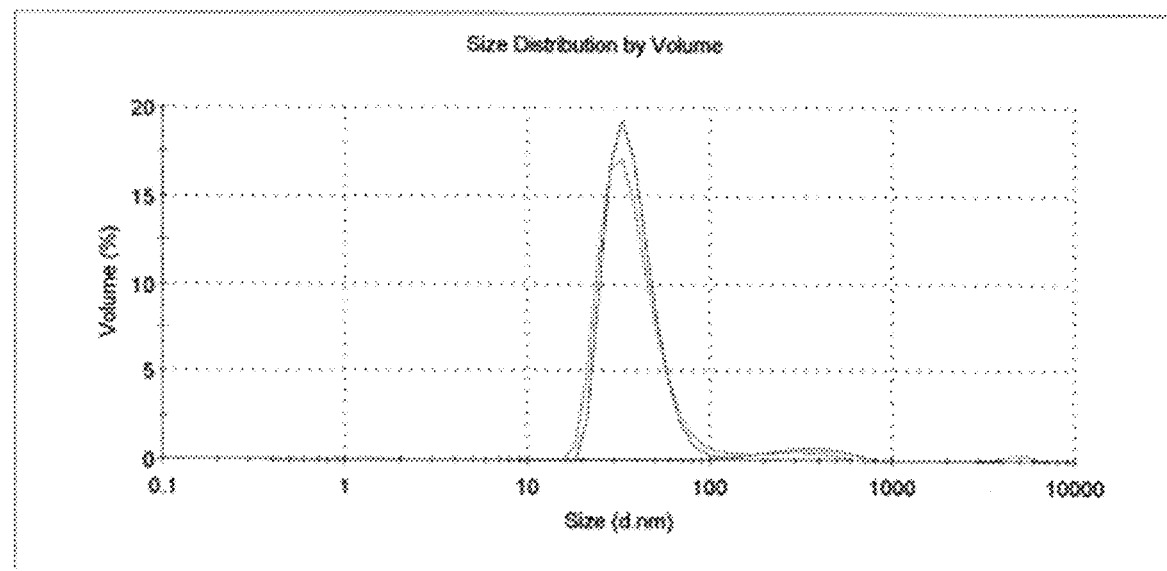
FIG. 2A Dynamic light scattering of purified CMVwt VLPs. The size of particles was detected by using Zetasizer Nano ZS (Malvern Instruments Ltd., United Kingdom).
Figure 2B:
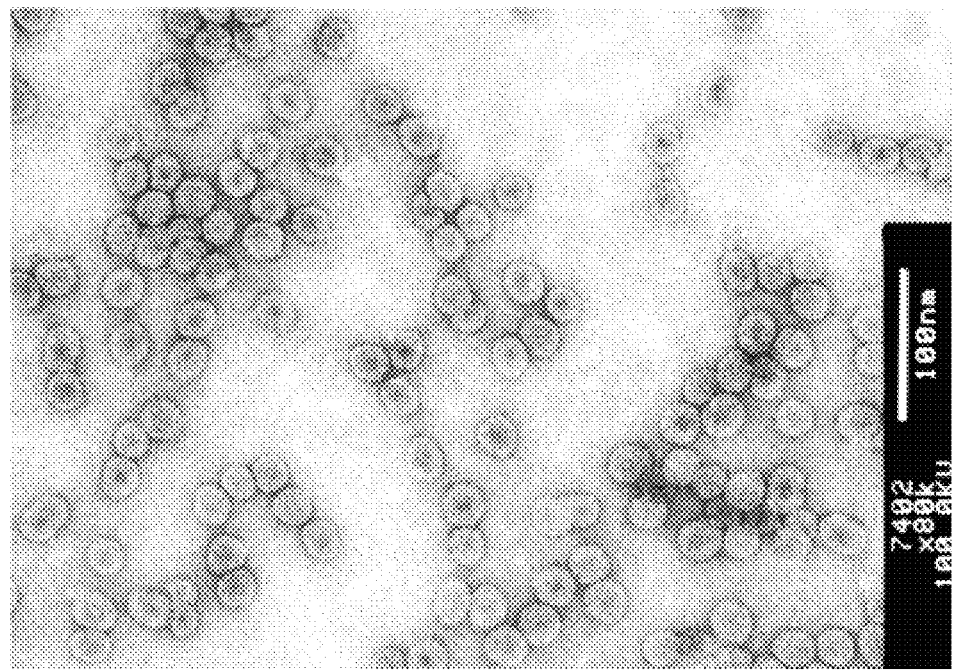
FIG. 2B Electron-microscopy analysis of purified CMVwt VLPs. For the morphological analysis of VLPs the JEM-1230 electron microscope (Jeol Ltd., Tokyo, Japan) was used.
Figure 3A:
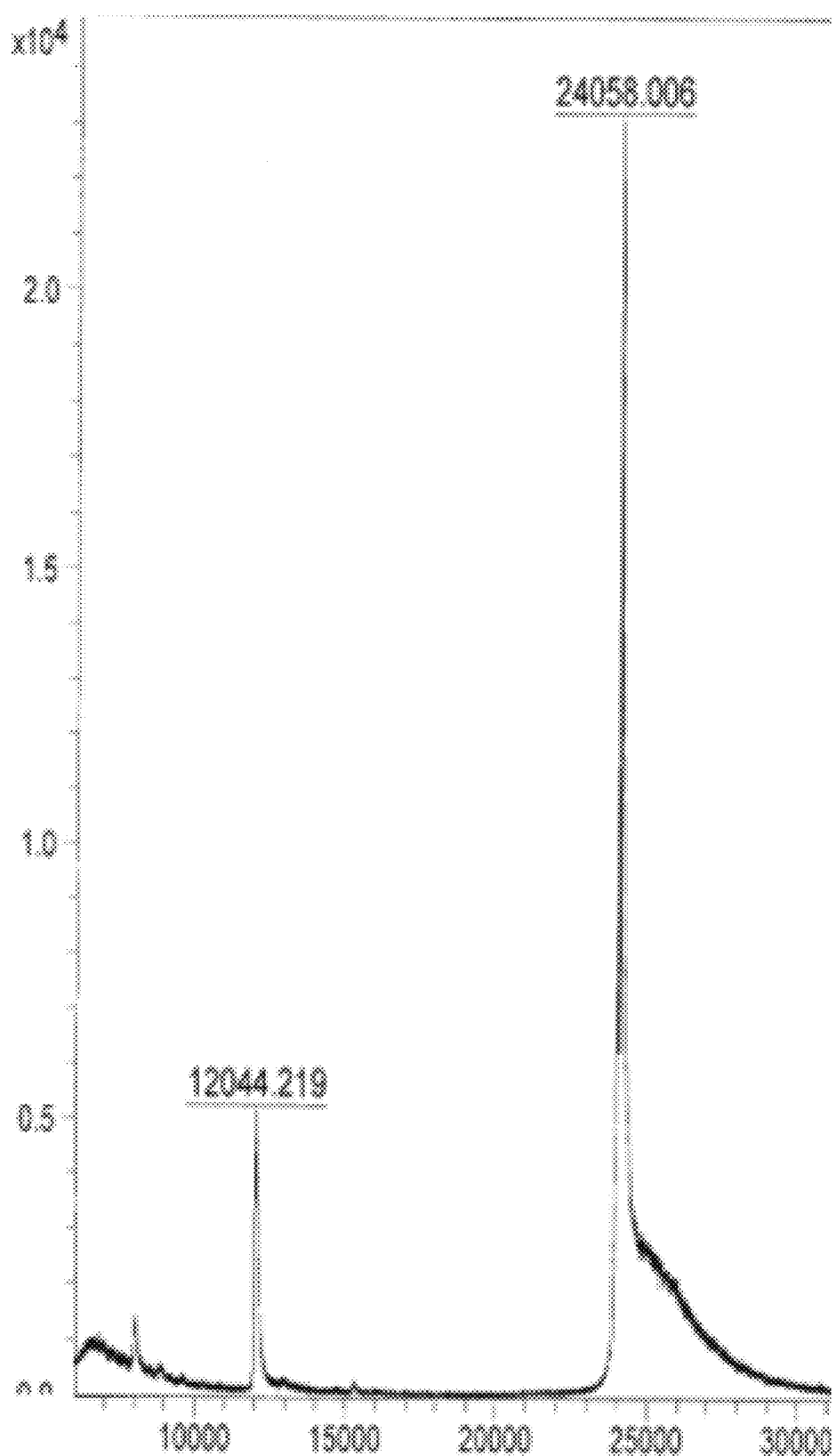
FIG. 3A CMVwild-type ("wt"); theoretical MM=24069; found MM=24058
Figure 3B:
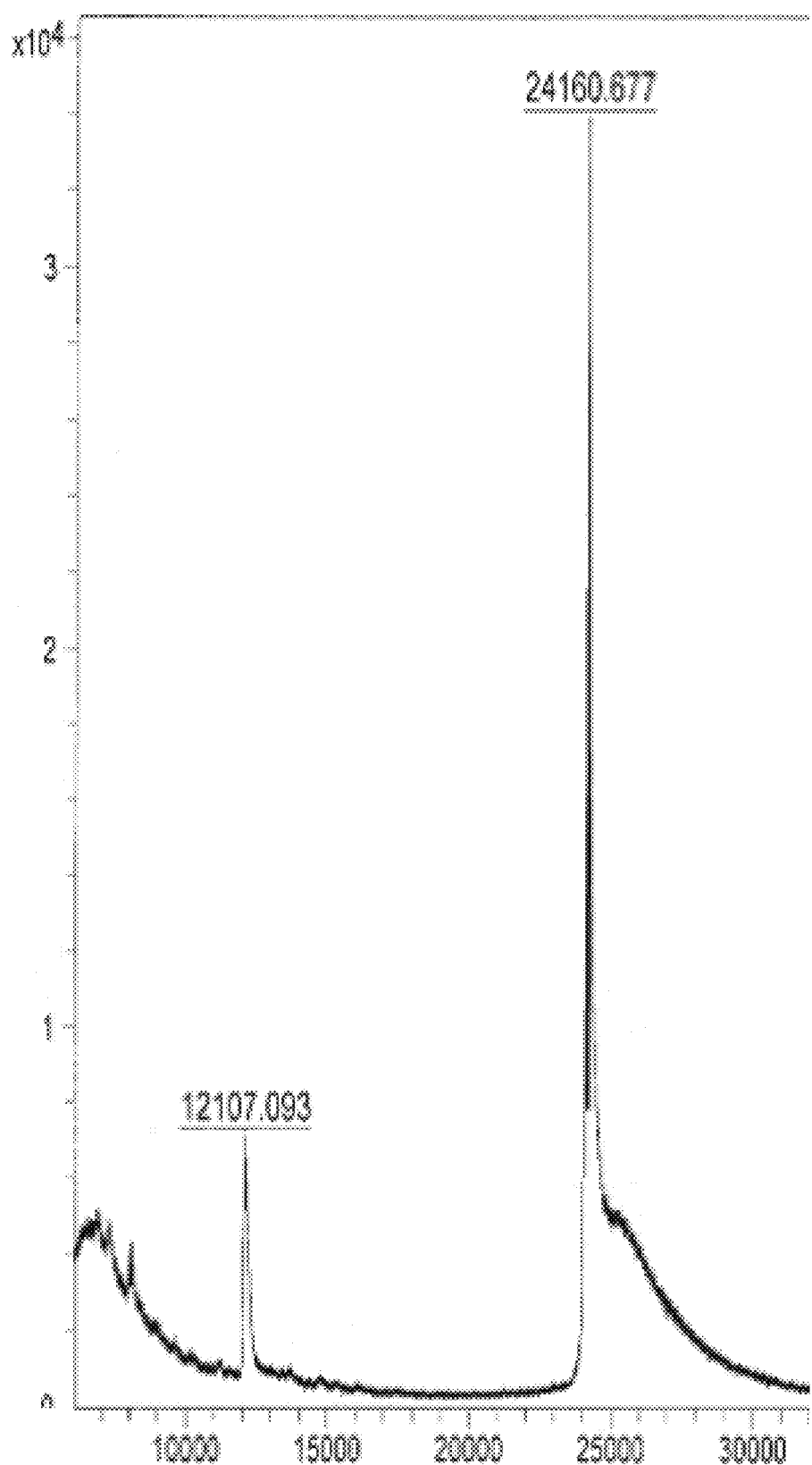
FIG. 3B CMV-Npadr; theoretical MM=24161 (without first Met); found MM=24160
Figure 3C:
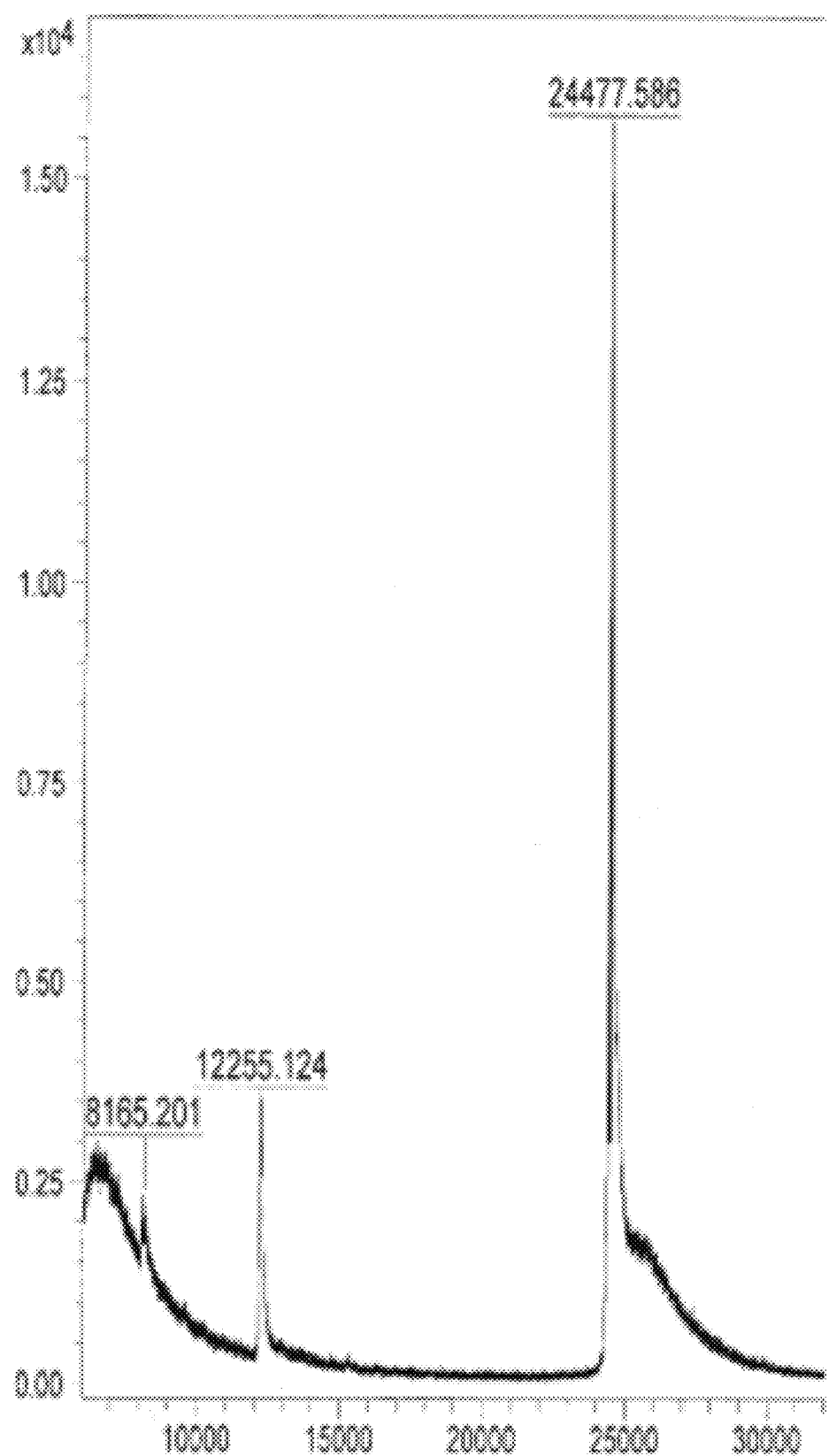
FIG. 3C CMV-Ntt830; theoretical MM=24483 (without first Met); found MM=24477
Figure 4A:
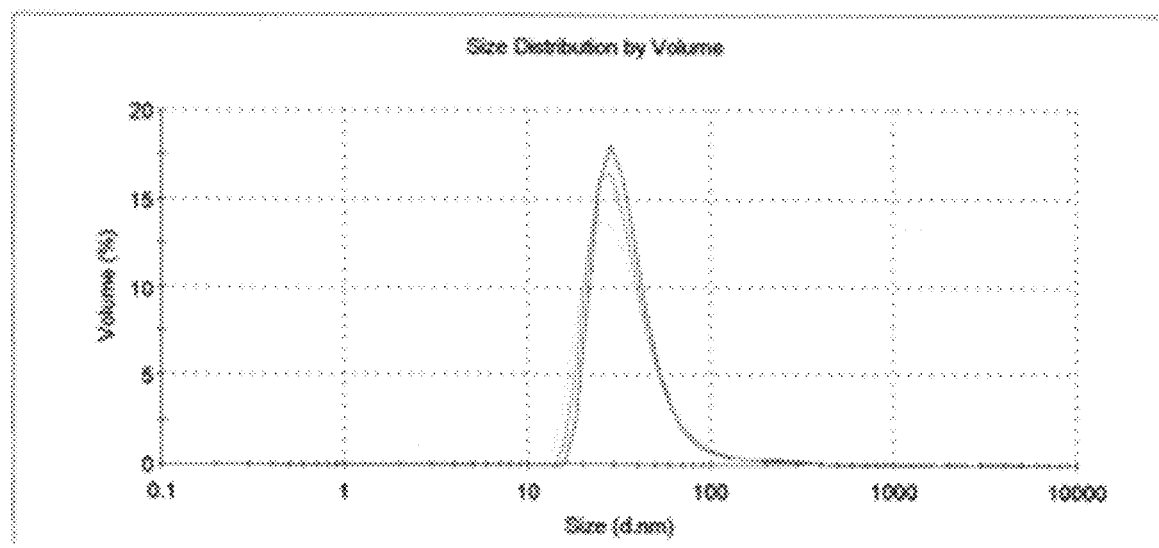
FIG. 4A Dynamic light scattering of purified CMV-Ntt830 VLPs. The size of particles was detected by using Zetasizer Nano ZS (Malvern Instruments Ltd., United Kingdom).
Figure 4B:
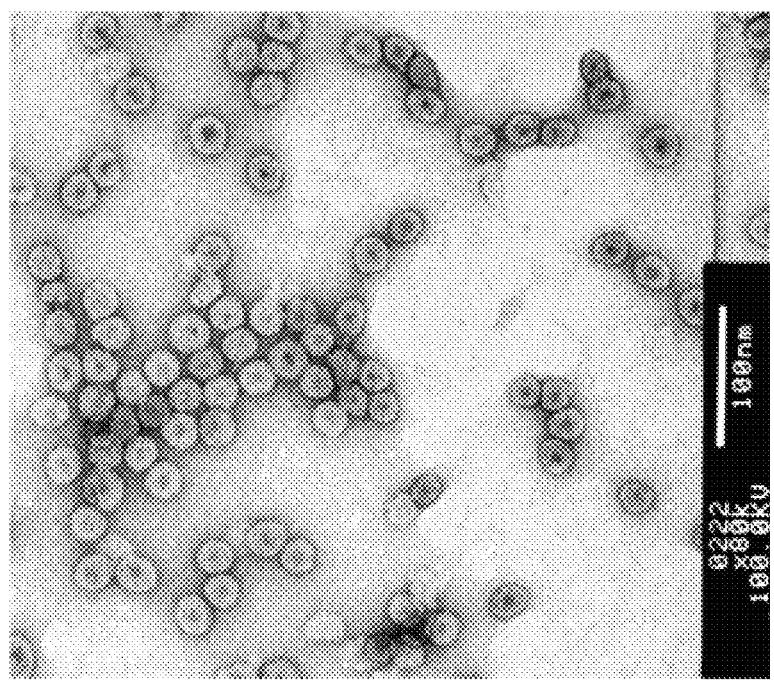
FIG. 4B Electron-microscopy analysis of purified CMV-Ntt830 VLPs. For the morphological analysis of VLPs the JEM-1230 electron microscope (Jeol Ltd., Tokyo, Japan) was used.
Figure 5A:
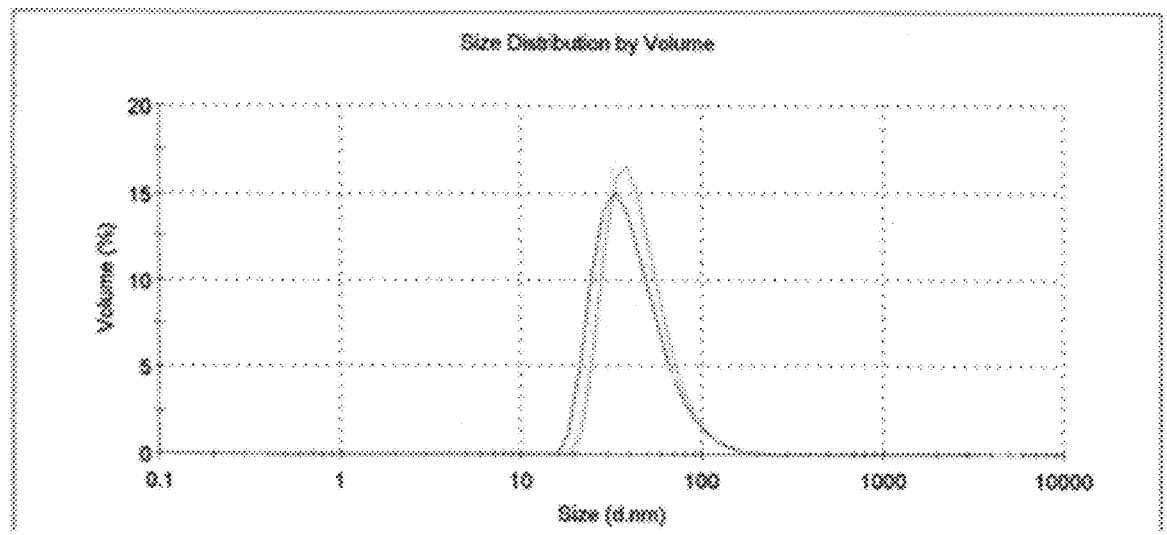
FIG. 5A Dynamic light scattering of purified CMV-Npadr VLPs. The size of particles was detected by using Zetasizer Nano ZS (Malvern Instruments Ltd., United Kingdom).
Figure 5B:
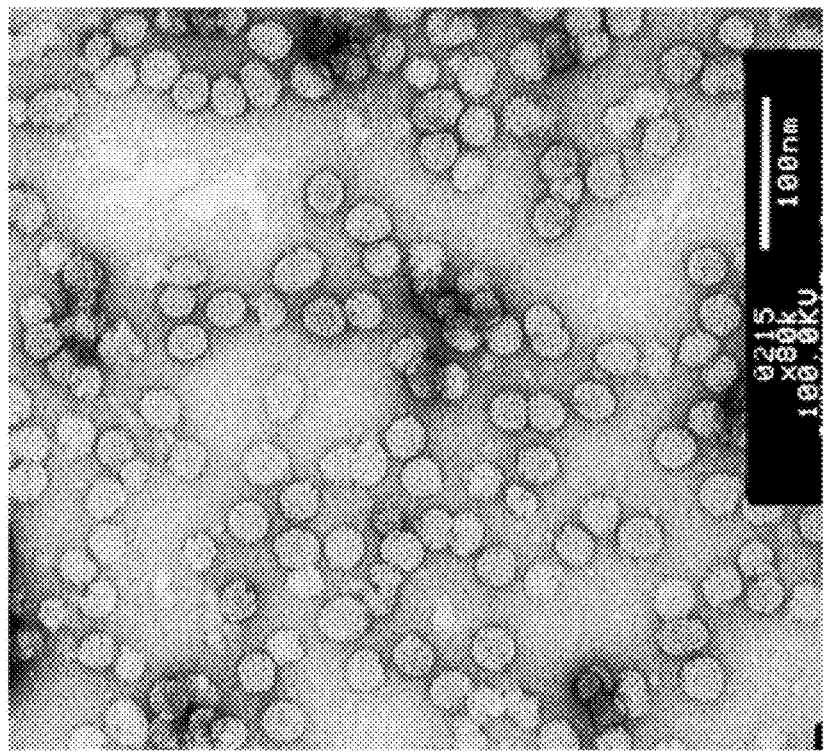
FIG. 5B Electron-microscopy analysis of purified CMV-Npadr VLPs. For the morphological analysis of VLPs the JEM-1230 electron microscope (Jeol Ltd., Tokyo, Japan) was used.

Unless defined otherwise, all technical and scientific terms used herein have the same meanings as commonly understood by one of ordinary skill in the art to which this invention belongs.

Virus-like particle (VLP): The term "virus-like particle (VLP)" as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. A virus-like particle in accordance with the invention is non-replicative and non-infectious since it lacks all or part of the viral genome or genome function. A virus-like particle in accordance with the invention may contain nucleic acid distinct from their genome. Recombinantly produced virus-like particles typically contain host cell derived RNA. A typical and preferred embodiment of a virus-like particle in accordance with the present invention is a viral capsid composed of polypeptides of the invention. A virus-like particle is typically a macromolecular assembly composed of viral coat protein which typically comprises 60, 120, 180, 240, 300, 360, or more than 360 protein subunits per virus-like particle. Typically and preferably, the interactions of these subunits lead to the formation of viral capsid or viral-capsid like structure with an inherent repetitive organization. One feature of a virus-like particle is its highly ordered and repetitive arrangement of its subunits.

Virus-like particle of CMV: The terms "virus-like particle of CMV" or CMV VLPs refer to a virus-like particle comprising, or preferably consisting essentially of, or preferably consisting of at least one CMV polypeptide. Preferably, a virus-like particle of CMV comprises said CMV polypeptide as the major, and even more preferably as the sole protein component of the capsid structure. Typically and preferably, virus-like particles of CMV resemble the structure of the capsid of CMV. Virus-like particles of CMV are non-replicative and/or non-infectious, and lack at least the gene or genes encoding for the replication machinery of the CMV, and typically also lack the gene or genes encoding the protein or proteins responsible for viral attachment to or entry into the host. This definition includes also virus-like particles in which the aforementioned gene or genes are still present but inactive. Preferred methods to render a virus-like particle of CMV non replicative and/or non-infectious is by physical or chemical inactivation, such as UV irradiation, formaldehyde treatment. Preferably, VLPs of CMV lack the gene or genes encoding for the replication machinery of the CMV, and also lack the gene or genes encoding the protein or proteins responsible for viral attachment to or entry into the host. Again more preferably, non-replicative and/or non-infectious virus-like particles are obtained by recombinant gene technology. Recombinantly produced virus-like particles of CMV according to the invention typically and preferably do not comprise the viral genome. Virus-like particles comprising more than one species of polypeptides, often referred to as mosaic VLPs are also encompassed by the invention. Thus, in one embodiment, the virus-like particle according to the invention comprises at least two different species of polypeptides, wherein at least one of said species of polypeptides is a CMV polypeptide. Preferably, a VLP of CMV is a macromolecular assembly composed of CMV coat protein which typically comprises 180 coat protein subunits per VLP. Typically and preferably, a VLP of CMV as used herein, comprises, essentially consists of, or alternatively consists of, at least one CMV polypeptide comprising or preferably consisting of (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said amino acid sequence to be mutated show a sequence identity of at least 90%, preferably of at least 95%, further preferably of at least 98% and again more preferably of at least 99%.

Polypeptide: The term "polypeptide" as used herein refers to a polymer composed of amino acid monomers which are linearly linked by peptide bonds (also known as amide bonds). The term polypeptide refers to a consecutive chain of amino acids and does not refer to a specific length of the product. Thus, peptides, and proteins are included within the definition of polypeptide.

Cucumber Mosaic Virus (CMV) polypeptide: The term "cucumber mosaic virus (CMV) polypeptide" as used herein refers to a polypeptide comprising or preferably consisting of: (i) an amino acid sequence of a coat protein of cucumber mosaic virus (CMV), or (ii) a mutated amino acid sequence, wherein the amino acid sequence to be mutated is an amino acid sequence of a coat protein of CMV, and wherein said mutated amino acid sequence and said amino acid sequence to be mutated, i.e. said coat protein of CMV, show a sequence identity of at least 90%, preferably of at least 95%, further preferably of at least 98% and again more preferably of at least 99%. Typically and preferably, the CMV polypeptide is capable of forming a virus-like particle of CMV upon expression by self-assembly.

Coat protein (CP) of cucumber mosaic virus (CMV): The term "coat protein (CP) of cucumber mosaic virus (CMV)", as used herein, refers to a coat protein of the cucumber mosaic virus which occurs in nature. Due to extremely wide host range of the cucumber mosaic virus, a lot of different strains and isolates of CMV are known and the sequences of the coat proteins of said strains and isolates have been determined and are, thus, known to the skilled person in the art as well. The sequences of said coat proteins (CPs) of CMV are described in and retrievable from the known databases such as Genbank, www.dpvweb.net, or www.ncbi.nlm.nih.gov/protein/. Examples are described in EP Application No. 14189897.3. Further examples of CMV coat proteins are provided in SEQ ID NOs 1-3. It is noteworthy that these strains and isolates have highly similar coat protein sequences at different protein domains, including the N-terminus of the coat protein. In particular, 98.1% of all completely sequenced CMV isolates share more than 85% sequence identity within the first 28 amino acids of their coat protein sequence, and still 79.5% of all completely sequenced CMV isolates share more than 90% sequence identity within the first 28 amino acids of their coat protein sequence.

Typically and preferably, the coat protein of CMV used for the present invention is capable of forming a virus-like particle of CMV upon expression by self-assembly. Preferably, the coat protein of CMV used for the present invention is capable of forming a virus-like particle of CMV upon expression by self-assembly in *E. coli*.

Modified virus-like particle (VLP) of cucumber mosaic virus (CMV): The term "modified virus-like particle (VLP) of cucumber mosaic virus (CMV)" as used herein, refers to a VLP of CMV which is a modified one in such as it comprises, or preferably consists essentially of, or preferably consists of at least one modified CMV polypeptide, wherein said modified CMV polypeptide comprises, or preferably consists of, a CMV polypeptide, and a T helper cell epitope. Typically and preferably, said T helper cell epitope (i) is fused to the N-terminus of said CMV polypeptide, (ii) is fused to the C-terminus of said CMV polypeptide, (iii) replaces a region of consecutive amino acids of said CMV polypeptide, wherein the sequence identity between said replaced region of consecutive amino acids of said CMV polypeptide and the T helper cell epitope is at least 15%, preferably at least 20%, or (iv) replaces a N-terminal region of said CMV polypeptide, and wherein said replaced N-terminal region of said CMV polypeptide consists of 5 to 15 consecutive amino acids. Preferably, said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids, and most preferably of 11, 12 or 13 consecutive amino acids. Preferably said modified VLP of CMV of the present invention is a recombinant modified VLP of CMV.

Modified CMV polypeptide: The term "modified CMV polypeptide" as used herein refers to a CMV polypeptide modified in such as defined herein, that said modified CMV polypeptide comprises, or preferably consists of, a CMV polypeptide, and a T helper cell epitope. Typically, the modified CMV polypeptide is capable of forming a virus-like particle of CMV upon expression by self-assembly. Preferably, the modified CMV polypeptide is a recombinant modified CMV polypeptide and is capable of forming a virus-like particle of CMV upon expression by self-assembly in *E. coli*.

N-terminal region of the CMV polypeptide: The term "N-terminal region of the CMV polypeptide" as used herein, refers either to the N-terminus of said CMV polypeptide, and in particular to the N-terminus of a coat protein of CMV, or to the region of the N-terminus of said CMV polypeptide or said coat protein of CMV but starting with the second amino acid of the N-terminus of said CMV polypeptide or said coat protein of CMV if said CMV polypeptide or said coat protein comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes. The term "N-terminal region of the mutated amino acid sequence of a CMV polypeptide or a CMV coat protein" as used herein, refers either to the N-terminus of said mutated amino acid sequence of said CMV polypeptide or said coat protein of CMV, or to the region of the N-terminus of said mutated amino acid sequence of said CMV polypeptide or said coat protein of CMV but starting with the second amino acid of the N-terminus of said mutated amino acid sequence of said CMV polypeptide or said coat protein of CMV if said mutated amino acid sequence comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes.

Recombinant polypeptide: In the context of the invention the term "recombinant polypeptide" refers to a polypeptide which is obtained by a process which comprises at least one step of recombinant DNA technology. Typically and preferably, a recombinant polypeptide is produced in a prokaryotic expression system. It is apparent for the artisan that recombinantly produced polypeptides which are expressed in a prokaryotic expression system such as *E. coli* may comprise an N-terminal methionine residue. The N-terminal methionine residue is typically cleaved off the recombinant polypeptide in the expression host during the maturation of the recombinant polypeptide. However, the cleavage of the N-terminal methionine may be incomplete. Thus, a preparation of a recombinant polypeptide may comprise a mixture of otherwise identical polypeptides with and without an N-terminal methionine residue. Typically and preferably, a preparation of a recombinant polypeptide comprises less than 10%, more preferably less than 5%, and still more preferably less than 1% recombinant polypeptide with an N-terminal methionine residue.

Recombinant CMV polypeptide: The term "recombinant CMV polypeptide" refers to a CMV polypeptide as defined above which is obtained by a process which comprises at least one step of recombinant DNA technology. Typically and preferably a preparation of a recombinant CMV polypeptide comprises less than 10%, more preferably less than 5%, and still more preferably less than 1% recombinant CMV polypeptide with an N-terminal methionine residue. Consequently, a recombinant virus-like particle of the invention may comprise otherwise identical recombinant polypeptides with and without an N-terminal methionine residue.

Recombinant modified CMV polypeptide: The term "recombinant modified CMV polypeptide" refers to a modified CMV polypeptide as defined above which is obtained by a process which comprises at least one step of recombinant DNA technology. Typically and preferably a preparation of a recombinant modified CMV polypeptide comprises less than 10%, more preferably less than 5%, and still more preferably less than 1% recombinant modified CMV polypeptide with an N-terminal methionine residue. Consequently, a recombinant virus-like particle of the invention may comprise otherwise identical recombinant polypeptides with and without an N-terminal methionine residue.

Recombinant virus-like particle: In the context of the invention the term "recombinant virus-like particle" refers to a virus-like particle (VLP) which is obtained by a process which comprises at least one step of recombinant DNA technology. Typically and preferably, a recombinant virus-like particle comprises at least one recombinant polypeptide, preferably a recombinant CMV polypeptide or recombinant modified CMV polypeptide. Most preferably, a recombinant virus-like particle is composed of or consists of recombinant CMV polypeptides or recombinant modified CMV polypeptides. As a consequence, if in the context of the present invention the definition of inventive recombinant VLPs are effected with reference to specific amino acid sequences comprising a N-terminal methionine residue the scope of these inventive recombinant VLPs encompass the VLPs formed by said specific amino acid sequences without said N-terminal methionine residue but as well, even though typically in a minor amount as indicated herein, the VLPs formed by said specific amino acid sequences with said N-terminal methionine. Furthermore, it is within the scope of the present invention that if the definition of inventive recombinant VLPs are effected with reference to specific amino acid sequences comprising a N-terminal methionine residue VLPs are encompassed comprising both amino acid sequences comprising still said N-terminal methionine residue and amino acid sequences lacking the N-terminal methionine residue.

Mutated amino acid sequence: The term "mutated amino acid sequence" refers to an amino acid sequence which is obtained by introducing a defined set of mutations into an amino acid sequence to be mutated. In the context of the invention, said amino acid sequence to be mutated typically and preferably is an amino acid sequence of a coat protein of CMV. Thus, a mutated amino acid sequence differs from an amino acid sequence of a coat protein of CMV in at least one amino acid residue, wherein said mutated amino acid sequence and said amino acid sequence to be mutated show a sequence identity of at least 90%. Typically and preferably said mutated amino acid sequence and said amino acid sequence to be mutated show a sequence identity of at least 91%, 92%, 93% 94%, 95%, 96%, 97%, 98%, or 99%. Preferably, said mutated amino acid sequence and said sequence to be mutated differ in at most 11, 10, 9, 8, 7, 6, 4, 3, 2, or 1 amino acid residues, wherein further preferably said difference is selected from insertion, deletion and amino acid exchange. Preferably, the mutated amino acid sequence differs from an amino acid sequence of a coat protein of CMV in least one amino acid, wherein preferably said difference is an amino acid exchange. Position corresponding to residues . . . : The position on an amino acid sequence, which is corresponding to given residues of another amino acid sequence can be identified by sequence alignment, typically and preferably by using the BLASTP algorithm, most preferably using the standard settings. Typical and preferred standard settings are: expect threshold: 10; word size: 3; max matches in a query range: 0; matrix: BLO-SUM62; gap costs: existence 11, extension 1; compositional adjustments: conditional compositional score matrix adjustment.

Sequence identity: The sequence identity of two given amino acid sequences is determined based on an alignment of both sequences. Algorithms for the determination of sequence identity are available to the artisan. Preferably, the sequence identity of two amino acid sequences is determined using publicly available computer homology programs such as the "BLAST" program (http://blast.ncbi.nlm.nih.gov/Blast.cgi) or the "CLUSTALW" (http://www.genome.jp/tools/clustalw/), and hereby preferably by the "BLAST" program provided on the NCBI homepage at http://blast.ncbi.nlm.nih.gov/Blast.cgi, using the default settings provided therein. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Amino acid exchange: The term amino acid exchange refers to the exchange of a given amino acid residue in an amino acid sequence by any other amino acid residue having a different chemical structure, preferably by another proteinogenic amino acid residue. Thus, in contrast to insertion or deletion of an amino acid, the amino acid exchange does not change the total number of amino acids of said amino acid sequence. Very preferred in the context of the invention is the exchange of an amino acid residue of said amino acid sequence to be mutated by a lysine residue or by a cysteine residue.

Epitope: The term epitope refers to continuous or discontinuous portions of an antigen, preferably a polypeptide, wherein said portions can be specifically bound by an antibody or by a T-cell receptor within the context of an MHC molecule. With respect to antibodies, specific binding excludes non-specific binding but does not necessarily exclude cross-reactivity. An epitope typically comprise 5-20 amino acids in a spatial conformation which is unique to the antigenic site.

T helper (Th) cell epitope: The term "T helper (Th) cell epitope" as used herein refers to an epitope that is capable of recognition by a helper Th cell. In another preferred embodiment, said T helper cell epitope is a universal T helper cell epitope.

Universal Th cell epitope: The term "universal Th cell epitope" as used herein refers to a Th cell epitope that is capable of binding to at least one, preferably more than one MHC class II molecules. The simplest way to determine whether a peptide sequence is a universal Th cell epitope is to measure the ability of the peptide to bind to individual MHC class II molecules. This may be measured by the ability of the peptide to compete with the binding of a known Th cell epitope peptide to the MHC class II molecule. A representative selection of HLA-DR molecules are described in e.g. Alexander J, et al., Immunity (1994) 1:751-761. Affinities of Th cell epitopes for MHC class II molecules should be at least $10^{-5}$M. An alternative, more tedious but also more relevant way to determine the "universality" of a Th cell epitope is the demonstration that a larger fraction of people (>30%) generate a measurable T cell response upon immunization and boosting one months later with a protein containing the Th cell epitope formulated in IFA. A representative collection of MHC class II molecules present in different individuals is given in Panina-Bordignon P, et al., Eur J Immunol (1989) 19:2237-2242. As a consequence, the term "universal Th cell epitope" as used herein preferably refers to a Th cell epitope that generates a measurable T cell response upon immunization and boosting (one months later with a protein containing the Th cell epitope formulated in IFA) in more than 30% of a selected group of individuals as described in Panina-Bordignon P, et al., Eur J Immunol (1989) 19:2237-2242. Moreover, and again further preferred, the term "universal Th cell epitope" as used herein preferably refers to a Th cell epitope that is capable of binding to at least one, preferably to at least two, and even more preferably to at least three DR alleles selected from of DR1, DR2w2b, DR3, DR4w4, DR4w14, DR5, DR7, DR52a, DRw53, DR2w2a; and preferably selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40. In an even again more preferable manner, the term "universal Th cell epitope" as used herein refers to a Th cell epitope that is capable of binding to at least one, preferably to at least two, and even more preferably to at least three DR alleles selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40.

Universal Th cell epitopes are described, and known to the skilled person in the art, such as by Alexander J, et al., Immunity (1994) 1:751-761, Panina-Bordignon P, et al., Eur J Immunol (1989) 19:2237-2242, Calvo-Calle J M, et al., J Immunol (1997) 159:1362-1373, and Valmori D, et al., J Immunol (1992) 149:717-721.

Peanut Allergen: The term "peanut allergen", as used herein, refers to any protein of the *Arachis hypogaea* species, and isoforms thereof, suggested to cause an allergy for a human. Preferably, the term "peanut allergen", as used herein, refers to any of the suggested peanut allergens, and isoforms thereof, as retrievable under www.allergen.org or a protein with an amino acid sequence of at least 90%, preferably of at least 92%, further preferably of at least 95%, and again further preferably of at least 98% amino acid sequence identity with such a peanut allergen and isoform thereof. More preferably, the term "peanut allergen", as used herein, refers to any of the suggested currently 17 peanut allergens, and isoforms thereof, as retrievable under www.allergen.org or a protein with an amino acid sequence of at least 90%, preferably of at least 92%, further preferably of at least 95%, and again further preferably of at least 98% amino acid sequence identity with such a peanut allergen and isoform thereof. Again more preferably, the term "peanut allergen", as used herein, refers to any one of the peanut allergens, and isoforms thereof, selected from Ara h1, Ara h2, Ara h3, Ara h4, Ara h5, Ara h6, Ara h7, Ara h8, Ara h9, Ara h10, Ara h11, Ara h12, Ara h13, Ara h14, Ara h15, Ara h16 and Ara h17, or a protein with an amino acid sequence of at least 90%, preferably of at least 92%, further preferably of at least 95%, and again further preferably of at least 98% amino acid sequence identity with such a peanut allergen and isoform thereof. Again more preferably, the term "peanut allergen", as used herein, refers to any one of the peanut allergens and isoforms thereof, selected from Ara h1, Ara h2, Ara h3, and Ara h6 or a protein with an amino acid sequence of at least 90%, preferably of at least 92%, further preferably of at least 95%, and again further preferably of at least 98% amino acid sequence identity with such a peanut allergen and isoform thereof. Again more preferably, the term "peanut allergen", as used herein, refers to any proteins selected from Ara h1, Ara h2, Ara h3 and Ara h6, and isoforms thereof, or a protein with an amino acid sequence of at least 90%, preferably of at least 92%, further preferably of at least 95%, and again further preferably of at least 98% amino acid sequence identity with such a peanut allergen. Again more preferably, the term "peanut allergen", as used herein, refers to any proteins selected from Ara h1, Ara h2, Ara h201, Ara-h202, Ara h3 and Ara h6, or a protein with an amino acid sequence of at least 90%, preferably of at least 92%, further preferably of at least 95%, and again further preferably of at least 98% amino acid sequence identity with such a peanut allergen. In a very preferred embodiment, said peanut allergen comprises, or preferably consists of, a protein with the amino sequence selected from SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30, or a protein with an amino acid sequence of at least 90%, preferably of at least 92%, further preferably of at least 95%, and again further preferably of at least 98% amino acid sequence identity with SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30. In a further very preferred embodiment, said peanut allergen comprises, or preferably consists of, a protein with the amino sequence selected from SEQ ID NO:17, SEQ ID NO:18; SEQ ID NO:19, SEQ ID NO:20, SEQ ID NO:22 or SEQ ID NO:30, or a protein with an amino acid sequence of at least 90%, preferably of at least 92%, further preferably of at least 95%, and again further preferably of at least 98% amino acid sequence identity with SEQ ID NO:17, SEQ ID NO:18; SEQ ID NO:19, SEQ ID NO:20, SEQ ID NO:22 or SEQ ID NO:30. In a further very preferred embodiment, said peanut allergen does not comprise an amino acid sequence selected from SEQ ID NO:26, SEQ ID NO:27 or SEQ ID NO:28.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. Preferred adjuvants are complete and incomplete Freund's adjuvant, aluminum containing adjuvant, preferably aluminum hydroxide, and modified muramyldipeptide. Further preferred adjuvants are mineral gels such as aluminum hydroxide, surface active substances such as lyso lecithin, pluronic polyols, polyanions, peptides, oil emulsions, keyhole limpet hemocyanins, dinitrophenol, and human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants may also comprise mixtures of these substances. Virus-like particles have been generally described as an adjuvant. However, the term "adjuvant", as used within the context of this application, refers to an adjuvant not being the inventive virus-like particle. Rather "adjuvant" relates to an additional, distinct component of the inventive compositions, vaccines or pharmaceutical compositions.

Effective amount: As used herein, the term "effective amount" refers to an amount necessary or sufficient to realize a desired biologic effect. An effective amount of the composition, or alternatively the pharmaceutical composition, would be the amount that achieves this selected result, and such an amount could be determined as a matter of routine by a person skilled in the art. Preferably, the term "effective amount", as used herein, refers to an amount necessary or sufficient to be effective to reduce levels of said at least one peanut allergen to a level that causes the reduction of at least one symptom caused by the peanut allergy. Preferably, the term "effective amount", as used herein, refers to an amount necessary or sufficient to be effective to neutralize the activity of at least one peanut allergen. The effective amount can vary depending on the particular composition being administered and the size of the subject. One of ordinary skill in the art can empirically determine the effective amount of a particular composition of the present invention without necessitating undue experimentation.

Treatment: As used herein, the terms "treatment", "treat", "treated" or "treating" refer to prophylaxis and/or therapy. In one embodiment, the terms "treatment", "treat", "treated" or "treating" refer to a therapeutic treatment. In another embodiment, the terms "treatment", "treat", "treated" or "treating" refer to a prophylactic treatment.

Attachment Site, First: As used herein, the phrase "first attachment site" refers to an element which is naturally occurring with the virus-like particle or which is artificially added to the virus-like particle, and to which the second attachment site may be linked. The first attachment site preferably is a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid residue, preferably of a lysine residue. The first attachment site is typically located on the surface, and preferably on the outer surface of the VLP. Multiple first attachment sites are present on the surface, preferably on the outer surface of the VLP, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in a preferred embodiment the first attachment site is artificially added to the VLP. In a very preferred embodiment said first attachment site is the amino group of a lysine residue of the amino acid sequence of said VLP polypeptide.

Attachment Site, Second: As used herein, the phrase "second attachment site" refers to an element which is naturally occurring with or which is artificially added to the at least one peanut allergen, and to which the first attachment site may be linked. The second attachment site of the at least one peanut allergen preferably is a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is a sulfhydryl group, preferably the sulfhydryl group of the amino acid cysteine most preferably the sulfhydryl group of a cysteine residue. The term "antigen with at least one second attachment site" or "at least one peanut allergen with at least one second attachment site" refers, therefore, to a construct comprising the at least one peanut allergen and at least one second attachment site. However, in particular for a second attachment site, which is not naturally occurring within the at least one peanut allergen, such a construct typically and preferably further comprises a "linker". In another preferred embodiment the second attachment site is associated with the at least one peanut allergen through at least one covalent bond, preferably through at least one peptide bond. In a further embodiment, the second attachment site is naturally occurring within the at least one peanut allergen. In another further very preferred embodiment, the second attachment site is artificially added to the at least one peanut allergen through a linker, wherein said linker comprises or alternatively consists of a cysteine. Preferably, the linker is fused to the at least one peanut allergen by a peptide bond or is added by chemical linkage.

Linked: The terms "linked" or "linkage" as used herein, refer to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only refer to a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker. In other preferred embodiments the first attachment site and the second attachment site are linked through at least one covalent bond, preferably through at least one peptide bond, and even more preferably through exclusively peptide bond(s).

Linker: A "linker", as used herein, either associates the second attachment site with the at least one peanut allergen or already comprises, essentially consists of, or consists of the second attachment site. Preferably, a "linker", as used herein, already comprises the second attachment site, typically and preferably—but not necessarily—as one amino acid residue, preferably as a cysteine residue. A preferred linkers are an amino acid linkers, i.e. linkers containing at least one amino acid residue. The term amino acid linker does not imply that such a linker consists exclusively of amino acid residues. However, a linker consisting exclusively of amino acid residues is a preferred embodiment of the invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Association of the linker with the at least one peanut allergen is preferably by way of at least one covalent bond, more preferably by way of at least one peptide bond.

Ordered and repetitive antigen array: As used herein, the term "ordered and repetitive antigen array" refers to a repeating pattern of at least one peanut allergens which typically and preferably is characterized by a high order of uniformity in spacial arrangement of said antigens with respect to the core particle and VLP, respectively. In one embodiment of the invention, the repeating pattern may be a geometric pattern. Preferred ordered and repetitive antigen arrays, moreover, possess strictly repetitive para-crystalline orders of at least one peanut allergens, preferably with spacing of 1 to 30 nanometers, preferably 2 to 15 nanometers, even more preferably 2 to 10 nanometers, even again more preferably 2 to 8 nanometers, and further more preferably 1.6 to 7 nanometers.

Immunostimulatory substance: As used herein, the term "immunostimulatory substance" refers to a substance capable of inducing and/or enhancing an immune response. Immunostimulatory substances, as used herein, include, but are not limited to, toll-like receptor activating substances and substances inducing cytokine secretion. Toll-like receptor activating substances include, but are not limited to, immunostimulatory nucleic acids, peptideoglycans, lipopolysaccharides, lipoteichonic acids, imidazoquinoline compounds, flagellins, lipoproteins, and immuno stimulatory organic substances such as taxol.

Immunostimulatory nucleic acid (ISS-NA): As used herein, the term immunostimulatory nucleic acid refers to a nucleic acid capable of inducing and/or enhancing an immune response. Immunostimulatory nucleic acids comprise ribonucleic acids and in particular desoxyribonucleic acids, wherein both, ribonucleic acids and desoxyribonucleic acids may be either double stranded or single stranded. Preferred ISS-NA are desoxyribonucleic acids, wherein further preferably said desoxyribonucleic acids are single stranded. Preferably, immunostimulatory nucleic acids contain at least one CpG motif comprising an unmethylated C. Very preferred immunostimulatory nucleic acids comprise at least one CpG motif, wherein said at least one CpG motif comprises or preferably consist of at least one, preferably one, CG dinucleotide, wherein the C is unmethylated. Preferably, but not necessarily, said CG dinucleotide is part of a palindromic sequence. The term immunostimulatory nucleic acid also refers to nucleic acids that contain modified bases, preferably 4-bromo-cytosine. Specifically preferred in the context of the invention are ISS-NA which are capable of stimulating IFN-alpha production in dendritic cells. Immunostimulatory nucleic acids useful for the purpose of the invention are described, for example, in WO2007/068747A1.

Oligonucleotide: As used herein, the term "oligonucleotide" refers to a nucleic acid sequence comprising 2 or more nucleotides, preferably about 6 to about 200 nucleotides, and more preferably 20 to about 100 nucleotides, and most preferably 20 to 40 nucleotides. Very preferably, oligonucleotides comprise about 30 nucleotides, more preferably oligonucleotides comprise exactly 30 nucleotides, and most preferably oligonucleotides consist of exactly 30 nucleotides. Oligonucleotides are polyribonucleotides or polydeoxribonucleotides and are preferably selected from (a) unmodified RNA or DNA, and (b) modified RNA or DNA. The modification may comprise the backbone or nucleotide analogues. Oligonucleotides are preferably selected from the group consisting of (a) single- and double-stranded DNA, (b) DNA that is a mixture of single- and double-stranded regions, (c) single- and double-stranded RNA, (d) RNA that is mixture of single- and double-stranded regions, and (e) hybrid molecules comprising DNA and RNA that are single-stranded or, more preferably, double-stranded or a mixture of single- and double-stranded regions. Preferred nucleotide modifications/analogs are selected from the group consisting of (a) peptide nucleic acid, (b) inosin, (c) tritylated bases, (d) phosphorothioates, (e) alkylphosphorothioates, (f) 5-nitroindole desoxyriboflīranosyl, (g) 5-methyldesoxycytosine, and (h) 5,6-dihydro-5,6-dihydroxydesoxythymidine. Phosphothioated nucleotides are protected against degradation in a cell or an organism and are therefore preferred nucleotide modifications. Unmodified oligonucleotides consisting exclusively of phosphodiester bound nucleotides, typically are more active than modified nucleotides and are therefore generally preferred in the context of the invention. Most preferred are oligonucleotides consisting exclusively of phosphodiester bound deoxinucleo tides, wherein further preferably said oligonucleotides are single stranded. Further preferred are oligonucleotides capable of stimulating IFN-alpha production in cells, preferably in dendritic cells. Very preferred oligonucleotides capable of stimulating IFN-alpha production in cells are selected from A-type CpGs and C-type CpGs. Further preferred are RNA-molecules without a Cap.

CpG motif: As used herein, the term "CpG motif refers to a pattern of nucleotides that includes an unmethylated central CpG, i.e. the unmethylated CpG dinucleotide, in which the C is unmethylated, surrounded by at least one base, preferably one or two nucleotides, flanking (on the 3' and the 5' side of) the central CpG. Typically and preferably, the CpG motif as used herein, comprises or alternatively consists of the unmethylated CpG dinucleotide and two nucleotides on its 5' and 3' ends. Without being bound by theory, the bases flanking the CpG confer a significant part of the activity to the CpG oligonucleotide.

Unmethylated CpG-containing oligonucleotide: As used herein, the term "unmethylated CpG-containing oligonucleotide" or "CpG" refers to an oligonucleotide, preferably to an oligodesoxynucleotide, containing at least one CpG motif. Thus, a CpG contains at least one unmethylated cytosine, guanine dinucleotide. Preferred CpGs stimulate/activate, e.g. have a mitogenic effect on, or induce or increase cytokine expression by, a vertebrate bone marrow derived cell. For example, CpGs can be useful in activating B cells, NK cells and antigen-presenting cells, such as dendritic cells, monocytes and macrophages. Preferably, CpG relates to an oligodesoxynucleotide, preferably to a single stranded oligodesoxynucleotide, containing an unmethylated cytosine followed 3' by a guanosine, wherein said unmethylated cytosine and said guanosine are linked by a phosphate bond, wherein preferably said phosphate bound is a phosphodiester bound or a phosphothioate bound, and wherein further preferably said phosphate bond is a phosphodiester bound. CpGs can include nucleotide analogs such as analogs containing phosphorothio ester bonds and can be double-stranded or single-stranded. Generally, double-stranded molecules are more stable in vivo, while single-stranded molecules have increased immune activity. Preferably, as used herein, a CpG is an oligonucleotide that is at least about ten nucleotides in length and comprises at least one CpG motif, wherein further preferably said CpG is 10 to 60, more preferably 15 to 50, still more preferably 20 to 40, still more preferably about 30, and most preferably exactly 30 nucleotides in length. A CpG may consist of methylated and/or unmethylated nucleotides, wherein said at least one CpG motif comprises at least one CG dinucleotide wherein the C is unmethylated. The CpG may also comprise methylated and unmethylated sequence stretches, wherein said at least one CpG motif comprises at least one CG dinucleotide wherein the C is unmethylated. Very preferably, CpG relates to a single stranded oligodesoxynucleotide containing an unmethylated cytosine followed 3' by a guanosine, wherein said unmethylated cytosine and said guanosine are linked by a phosphodiester bound. The CpGs can include nucleotide analogs such as analogs containing phosphorothioester bonds and can be double-stranded or single-stranded. Generally, phosphodiester CpGs are A-type CpGs as indicated below, while phosphothioester stabilized CpGs are B-type CpGs. Preferred CpG oligonucleotides in the context of the invention are A-type CpGs.

A-type CpG: As used herein, the term "A-type CpG" or "D-type CpG" refers to an oligodesoxynucleotide (ODN) comprising at least one CpG motif. A-type CpGs preferentially stimulate activation of T cells and the maturation of dendritic cells and are capable of stimulating IFN-alpha production. In A-type CpGs, the nucleotides of the at least one CpG motif are linked by at least one phosphodiester bond. A-type CpGs comprise at least one phosphodiester bond CpG motif which may be flanked at its 5' end and/or, preferably and, at its 3' end by phosphorothioate bound nucleotides. Preferably, the CpG motif, and hereby preferably the CG dinucleotide and its immediate flanking regions comprising at least one, preferably two nucleotides, are composed of phosphodiester nucleotides. Preferred A-type CpGs exclusively consist of phosphodiester (PO) bond nucleotides. Typically and preferably, the poly G motif comprises or alternatively consists of at least one, preferably at least three, at least 4, 5, 6, 7, 8, 9, 10, 11, 12, 13, 14, or 15 Gs (guanosines), most preferably by at least 10 Gs. Preferably, the A-type CpG of the invention comprises or alternatively consists of a palindromic sequence.

Packaged: The term "packaged" as used herein refers to the state of a polyanionic macromolecule or immunostimulatory substances in relation to the core particle and VLP, respectively. The term "packaged" as used herein includes binding that may be covalent, e.g., by chemically coupling, or non-covalent, e.g., ionic interactions, hydrophobic interactions, hydrogen bonds, etc. The term also includes the enclosement, or partial enclosement, of a polyanionic macromolecule. Thus, the polyanionic macromolecule or immunostimulatory substances can be enclosed by the VLP without the existence of an actual binding, in particular of a covalent binding. In preferred embodiments, the at least one polyanionic macromolecule or immunostimulatory substances is packaged inside the VLP, most preferably in a non-covalent manner. In case said immunostimulatory substances is nucleic acid, preferably a DNA, the term packaged implies that said nucleic acid is not accessible to nucleases hydrolysis, preferably not accessible to DNAse hydrolysis (e.g. DNaseI or Benzonase), wherein preferably said accessibility is assayed as described in Examples 11-17 of WO2003/024481A2.

Thus, in a first aspect, the present invention provides for a composition comprising (a) a modified virus-like particle (VLP) with at least one first attachment site, wherein said modified VLP comprises, essentially consists of, or consists of, at least one modified VLP polypeptide, wherein said modified VLP polypeptide comprises, or preferably consists of, a) a VLP polypeptide, and b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%; and (b) at least one peanut allergen with at least one second attachment site, wherein preferably said peanut allergen is selected from the peanut allergens, and isoforms thereof, of Ara h1, Ara h2, Ara h3 and Ara h6 and proteins with an amino acid sequence of at least 90%, preferably of at least 92%, further preferably of at least 95%, and again further preferably of at least 98% amino acid sequence identity with said peanut allergens and isoforms thereof; and wherein further preferably said peanut allergen comprises, or preferably consists of, a protein with the amino sequence selected from SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30, or a protein with an amino acid sequence of at least 90%, preferably of at least 92%, further preferably of at least 95%, and again further preferably of at least 98% amino acid sequence identity with SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30; wherein (a) and (b) are linked through said at least one first and said at least one second attachment site via at least one non-peptide covalent bond.

In a preferred embodiment, said virus-like particle (VLP) is a recombinant VLP. In a further preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, a) a CMV polypeptide, and b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. In a further very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 90% with SEQ ID NO:23. In a further very preferred embodiment, said VLP is a modified VLP of cucumber mosaic virus (CMV), wherein said modified CMV polypeptide comprises, preferably consists of, an amino acid sequence of SEQ ID NO:6 or SEQ ID NO:7.

In a further very preferred embodiment, said at least one peanut allergen comprises, or preferably consists of, a protein selected from Ara h1, Ara h2, Ara h3 and Ara h6, an isoform thereof, or a protein with an amino acid sequence of at least 90%, preferably of at least 92%, further preferably of at least 95%, and again further preferably of at least 98% amino acid sequence identity with such a peanut allergen or isoform. In a very preferred embodiment, said peanut allergen comprises, or preferably consists of, a protein with the amino sequence selected from SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30, or a protein with an amino acid sequence of at least 90%, preferably of at least 92%, further preferably of at least 95%, and again further preferably of at least 98% amino acid sequence identity with SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30. In a further very preferred embodiment, said peanut allergen comprises, or preferably consists of, a protein with the amino sequence selected from SEQ ID NO:17, SEQ ID NO:18; SEQ ID NO:19, SEQ ID NO:20, SEQ ID NO:22 or SEQ ID NO:30, or a protein with an amino acid sequence of at least 90%, preferably of at least 92%, further preferably of at least 95%, and again further preferably of at least 98% amino acid sequence identity with SEQ ID NO:17, SEQ ID NO:18; SEQ ID NO:19, SEQ ID NO:20, SEQ ID NO:22 or SEQ ID NO:30.

In a further very preferred embodiment, said at least one peanut allergen comprises, or preferably consists of, a protein with the amino sequence of SEQ ID NO:18, an isoform thereof, or of a protein with an amino acid sequence of at least 90%, preferably of at least 92%, further preferably of at least 95%, and again further preferably of at least 98% amino acid sequence identity with SEQ ID NO:18. In a further very preferred embodiment, said at least one peanut allergen comprises, or preferably consists of, a protein with the amino sequence of SEQ ID NO:18. In a further very preferred embodiment, said at least one peanut allergen comprises, or preferably consists of, a protein with the amino sequence of SEQ ID NO:17. In a further very preferred embodiment, said at least one peanut allergen comprises, or preferably consists of, a protein with the amino sequence of SEQ ID NO:20. In a further very preferred embodiment, said at least one peanut allergen comprises, or preferably consists of, a protein with the amino sequence of SEQ ID NO:22. In a further very preferred embodiment, said at least one peanut allergen comprises, or preferably consists of, a protein with the amino sequence of SEQ ID NO:25. In a further embodiment, said at least one peanut allergen comprises, or preferably consists of, a protein with the amino sequence of SEQ ID NO:26. In a further embodiment, said at least one peanut allergen comprises, or preferably consists of, a protein with the amino sequence of SEQ ID NO:27. In another embodiment, said at least one peanut allergen comprises, or preferably consists of, a protein with the amino sequence of SEQ ID NO:28. In a further embodiment, said peanut allergen does not comprise an amino acid sequence selected from SEQ ID NO:26, SEQ ID NO:27 or SEQ ID NO:28.

In a further very preferred embodiment, said at least one peanut allergen is derived from a peanut extract, wherein preferably said peanut extract is derived from native peanuts or roasted peanuts or a mixture thereof, and wherein further preferably said peanut extract is derived from native peanuts or roasted peanuts. In a further very preferred embodiment, said peanut extract is obtainable by (a) grinding peanuts for providing a peanut powder, wherein preferably said peanuts are native peanuts or roasted peanuts or a mixture thereof (b) suspending said peanut powder in a buffer with a pH between 7 and 9, and (c) isolating the resulting aqueous liquid supernatant of step (b) thereby providing said peanut extract.

The generation of peanut extracts is known to the skilled person in the art and described for example in WO 2013/087119. A preferred method of obtaining a peanut extract for the present invention is described in Example 7. Thus, a further preferred method of obtaining a peanut extract is described by Koppelman et al. (Koppelman et al., Food Chem Toxicol (2016), May; 91:82-90. doi: 10.1016/j.fct.2016.02.016. Epub 2016 Feb. 26).

In a further very preferred embodiment, said second attachment site is a sulfhydryl group. In a further embodiment, said sulfhydryl group is derived from reaction of said at least one peanut allergen with N-succinimidyl S-acetylthioacetate (SATA), SATP, iminothiolane or a derivative thereof. In a further very preferred embodiment, said sulfhydryl group is derived from reaction of said at least one peanut allergen with N-succinimidyl S-acetylthioacetate (SATA). In a further very preferred embodiment, said second attachment site is a sulfhydryl group, and wherein preferably said sulfhydryl group is derived from reaction of a lysine residue of said at least one peanut allergen.

In another aspect, the present invention provides a composition for use in a method of preventing or treating peanut allergy in a human, wherein an effective amount of said composition is administered to said human, and wherein said composition comprises (a) a modified virus-like particle (VLP) with at least one first attachment site, wherein said modified VLP comprises, essentially consists of, or consists of, at least one modified VLP polypeptide, wherein said modified VLP polypeptide comprises, or preferably consists of, a) a VLP polypeptide, and b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%; and (b) at least one peanut allergen with at least one second attachment site, wherein preferably said peanut allergen is selected from the peanut allergens, and isoforms thereof, of Ara h1, Ara h2, Ara h3 and Ara h6 and proteins with an amino acid sequence of at least 90%, preferably of at least 92%, further preferably of at least 95%, and again further preferably of at least 98% amino acid sequence identity with said peanut allergens and isoforms thereof; and wherein further preferably said peanut allergen comprises, or preferably consists of, a protein with the amino sequence selected from SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30, or a protein with an amino acid sequence of at least 90%, preferably of at least 92%, further preferably of at least 95%, and again further preferably of at least 98% amino acid sequence identity with SEQ ID NO:18; SEQ ID NO:17, SEQ ID NO:19, SEQ ID NO:20, SEQ ID NO:22, SEQ ID NO:25, SEQ ID NO's:26-28 or SEQ ID NO:30; wherein (a) and (b) are linked through said at least one first and said at least one second attachment site via at least one non-peptide covalent bond.

In a preferred embodiment, said virus-like particle (VLP) is derived from a plant virus. In another preferred embodiment, said VLP is a recombinant VLP, and wherein preferably said recombinant VLP is derived from a plant virus. In another preferred embodiment, said VLP is a VLP of cucumber mosaic virus (CMV).

In a preferred embodiment, said VLP is a modified VLP comprising, essentially consisting of, or alternatively consisting of, at least one modified VLP polypeptide, wherein said modified VLP polypeptide comprises, or preferably consists of, a) a VLP polypeptide, and b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%.

In a preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, a) a CMV polypeptide, and b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%.

In a preferred embodiment, said CMV polypeptide comprises, preferably consists of, an amino acid sequence of a coat protein of CMV. In another preferred embodiment, said CMV polypeptide comprises, preferably consists of a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. Typically and preferably, said mutated amino acid sequence and said amino acid sequence to be mutated differ in least one and in at most 11, 10, 9, 8, 7, 6, 5, 4, 3, or 2 amino acid residues, and wherein preferably these differences are selected from (i) insertion, (ii) deletion, (iii) amino acid exchange, and (iv) any combination of (i) to (iii).

In another preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1.

In another preferred embodiment, said CMV polypeptide comprises, or preferably consists of, (i) (a) an amino acid sequence of a coat protein of CMV, wherein said amino acid sequence comprises SEQ ID NO:23, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:23; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In a further preferred embodiment, said CMV polypeptide comprises, or preferably consists of, (a) an amino acid sequence of a coat protein of CMV, wherein said amino acid sequence comprises SEQ ID NO:23, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:23.

In another preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:23; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 98% preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 90% with SEQ ID NO:23.

In another preferred embodiment, said T helper cell epitope replaces a N-terminal region of said CMV polypeptide. In another preferred embodiment the number of amino acids of said N-terminal region replaced is equal to or lower than the number of amino acids of which said T helper cell epitope consists.

In a further very preferred embodiment, said T helper cell epitope replaces a N-terminal region of said CMV polypeptide, and wherein the number of amino acids of said N-terminal region replaced is equal to or lower than the number of amino acids of which said T helper cell epitope consists. Typically and preferably, said replaced N-terminal region of said CMV polypeptide consists of 5 to 15 consecutive amino acids, preferably of 9 to 14 consecutive amino acids, more preferably of 11 to 13 consecutive amino acids.

In a further very preferred embodiment, said N-terminal region of said CMV polypeptide corresponds to amino acids 2-12 of SEQ ID NO:1.

In another very preferred embodiment, said T helper cell epitope is a universal T helper cell epitope. In another preferred embodiment, said T helper cell epitope consists of at most 20 amino acids.

In a very preferred embodiment, said Th cell epitope is a PADRE sequence. In a further very referred embodiment, said Th cell epitope comprises, preferably consists of, the amino acid sequence of SEQ ID NO:5. In another very preferred embodiment, said Th cell epitope is a PADRE sequence, and wherein said Th cell epitope comprises, preferably consists of, the amino acid sequence of SEQ ID NO:5.

In another preferred embodiment, said T helper cell epitope is derived from a human vaccine. In a very preferred embodiment, said Th cell epitope is derived from tetanus toxin. In a further very referred embodiment, said Th cell epitope has, preferably consists of, the amino acid sequence of SEQ ID NO:4. In another very preferred embodiment, said Th cell epitope is derived from tetanus toxin, and wherein said Th cell epitope has, preferably consists of, the amino acid sequence of SEQ ID NO:4.

In a very preferred embodiment, said Th cell epitope is a PADRE sequence, and wherein said Th cell epitope comprises, preferably consists of, the amino acid sequence of SEQ ID NO:5; or wherein said Th cell epitope is derived from tetanus toxin, and wherein said Th cell epitope has, preferably consists of, the amino acid sequence of SEQ ID NO:4.

In a very preferred embodiment, said CMV polypeptide comprises, or preferably consists of, an amino acid sequence of a coat protein of CMV, wherein said amino acid sequence comprises, or preferably consists of, SEQ ID NO:1 or an amino acid sequence having a sequence identity of at least 95% of SEQ ID NO:1; and wherein said amino acid sequence comprises SEQ ID NO:23, and wherein said T helper cell epitope replaces the N-terminal region of said CMV polypeptide, and wherein said replaced N-terminal region of said CMV polypeptide consists of 11 to 13 consecutive amino acids, preferably of 11 consecutive amino acids, and wherein further preferably said N-terminal region of said CMV polypeptide corresponds to amino acids 2-12 of SEQ ID NO:1.

In another very preferred embodiment, said modified CMV polypeptide comprises, preferably consists of, an amino acid sequence of SEQ ID NO:6. In another very preferred embodiment, said modified CMV polypeptide comprises, preferably consists of, an amino acid sequence of SEQ ID NO:7. The use of a composition of any one of the claims 6 to 8, wherein said modified CMV polypeptide comprises, preferably consists of, an amino acid sequence of SEQ ID NO:6 or SEQ ID NO:7.

In a very preferred embodiment, said first attachment site and said second attachment site are linked via at least one covalent non-peptide-bond. In another very preferred embodiment, said first attachment site comprises, or preferably is, an amino group, preferably an amino group of a lysine. In a further very preferred embodiment, said second attachment site comprises, or preferably is, a sulfhydryl group, preferably a sulfhydryl group of a cysteine.

In a very preferred embodiment, the at least one first attachment site is an amino group, preferably an amino group of a lysine residue and the at least one second attachment site is a sulfhydryl group, preferably a sulfhydryl group of a cysteine residue or a sufhydryl group that has been chemically attached to the at least one peanut allergen. In a further preferred embodiment only one of said second attachment sites associates with said first attachment site through at least one non-peptide covalent bond leading to a single and uniform type of binding of said at least one peanut allergen to said modified virus-like particle, wherein said only one second attachment site that associates with said first attachment site is a sulfhydryl group, and wherein said at least one peanut allergen and said modified virus-like particle interact through said association to form an ordered and repetitive antigen array, i.e. an ordered and repetitive array of peanut allergens.

In one preferred embodiment of the invention, the at least one peanut allergen is linked to the modified VLP by way of chemical cross-linking, typically and preferably by using a heterobifunctional cross-linker. In preferred embodiments, the hetero-bifunctional cross-linker contains a functional group which can react with the preferred first attachment sites, preferably with the amino group, more preferably with the amino groups of lysine residue(s) of the modified VLP, and a further functional group which can react with the preferred second attachment site, i.e. a sulfhydryl group, preferably of cysteine(s) residue inherent of, or artificially added to the at least one peanut allergen, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, Sulfo-KMUS SVSB, SIA, and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the at least one peanut allergen and the modified VLP upon coupling. Preferred cross-linkers belonging to this class include, for example, SPDP and Sulfo-LC-SPDP (Pierce). In a very preferred embodiment, said hetero-bifunctional cross-linker is SMPH.

Linking of the at least one peanut allergen to the modified VLP by using a hetero-bifunctional cross-linker according to the preferred methods described above, allows coupling of the at least one peanut allergen to the modified VLP in an oriented fashion. Other methods of linking the at least one peanut allergen to the modified VLP include methods wherein the at least one peanut allergen is cross-linked to the modified VLP, using the carbodiimide EDC, and NHS. The at least one peanut allergen may also be first thiolated through reaction, for example with SATA, SATP or iminothiolane, or a derivative thereof or other compounds capable of introducing a sulfhydryl group known to the skilled person in the art (G. Hermanson, Bioconjugate Techniques, Elsevier 2$^{nd}$ edition 2008). The at least one peanut allergen, after deprotection if required, may then be coupled to the modified VLP as follows. After separation of the excess thiolation reagent, the at least one peanut allergen is reacted with the modified VLP, previously activated with a hetero-bifunctional cross-linker comprising a cysteine reactive moiety, and therefore displaying at least one or several functional groups reactive towards cysteine residues, to which the thiolated at least one peanut allergen can react, such as described above. Optionally, low amounts of a reducing agent are included in the reaction mixture. In further methods, the at least one peanut allergen is attached to the modified VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the modified VLP.

In a further preferred embodiment said composition further comprises at least one immuno-stimulatory substance. In a very preferred embodiment, said immunostimulatory substance is packaged into the modified VLPs of the invention. In another preferred embodiment, the immunostimulatory substance is mixed with the modified VLPs of the invention. Immunostimulatory substances useful for the invention are generally known in the art and are disclosed, inter alia, in WO2003/024481A2.

In another embodiment of the present invention, said immunostimulatory substance consists of DNA or RNA of non-eukaryotic origin. In a further preferred embodiment said immunostimulatory substance is selected from the group consisting of: (a) immunostimulatory nucleic acid; (b) peptidoglycan; (c) lipopolysaccharide; (d) lipoteichonic acid; (e) imidazoquinoline compound; (f) flagelline; (g) lipoprotein; and (h) any mixtures of at least one substance of (a) to (g). In a further preferred embodiment said immunostimulatory substance is an immunostimulatory nucleic acid, wherein said immunostimulatory nucleic acid is selected from the group consisting of: (a) ribonucleic acids; (b) deoxyribonucleic acids; (c) chimeric nucleic acids; and (d) any mixture of (a), (b) and/or (c). In a further preferred embodiment said immunostimulatory nucleic acid is a ribonucleic acid, and wherein said ribonucleic acid is bacteria derived RNA. In a further preferred embodiment said immunostimulatory nucleic is poly-(I:C) or a derivative thereof. In a further preferred embodiment said immunostimulatory nucleic acid is a deoxyribonucleic acid, wherein said deoxyribonucleic acid is an unmethylated CpG-containing oligonucleotide.

In a very preferred embodiment said immunostimulatory substance is an unmethylated CpG-containing oligonucleotide. In a further preferred embodiment said unmethylated CpG-containing oligonucleotide is an A-type CpG. In a further preferred embodiment said A-type CpG comprises the sequence GACGATCGTC (SEQ ID NO:24). In a further preferred embodiment said palindromic sequence is flanked at its 5'-terminus and at its 3'-terminus by guanosine entities. In a further preferred embodiment said palindromic sequence is flanked at its 5'-terminus by at least 3 and at most 15 guanosine entities, and wherein said palindromic sequence is flanked at its 3'-terminus by at least 3 and at most 15 guanosine entities.

In another preferred embodiment, said immunostimulatory substance is an unmethylated CpG-containing oligonucleotide, and wherein preferably said unmethylated CpG-containing oligonucleotide comprises a palindromic sequence, and wherein further preferably the CpG motif of said unmethylated CpG-containing oligonucleotide is part of a palindromic sequence, and wherein again further preferably said palindromic sequence is GACGATCGTC (SEQ ID NO:24).

In very preferred embodiments, said at least one at least one peanut allergen is linked via a sulfhydryl group to said modified VLP, again further preferably to said modified CMV VLP, wherein preferably said sulfhydryl group is comprised by said second attachment site and wherein said sulfhydryl group is not naturally occurring with said at least one peanut allergen, and wherein preferably said sulfhydryl group is derived from reaction of said at least one peanut allergen with N-succinimidyl S-acetylthioacetate (SATA), SATP, iminothiolane or a derivative thereof, further preferably wherein said sulfhydryl group is derived from reaction of said at least one peanut allergen with N-succinimidyl S-acetylthioacetate (SATA). In a further very preferred embodiment, said second attachment site is a sulfhydryl group, and wherein preferably said sulfhydryl group is derived from reaction of a lysine residue of said at least one peanut allergen.

In other preferred embodiments of the invention, the at least one peanut allergen is linked via a cysteine residue, having been added to either the N-terminus or the C-terminus of, or a natural cysteine residue within the at least one peanut allergen, to lysine residues of the modified virus-like particle. In a preferred embodiment, the composition of the invention further comprises a linker, wherein said linker associates said at least one peanut allergen with said second attachment site, and wherein preferably said linker comprises or alternatively consists of said second attachment site.

In a preferred embodiment, said at least one peanut allergen comprises, or preferably consists of, a protein with an amino acid sequence of at least 90% amino acid sequence identity with SEQ ID NO:17, SEQ ID NO:18; SEQ ID NO:19, SEQ ID NO:20, SEQ ID NO:22 or SEQ ID NO:30. In a preferred embodiment, said at least one peanut allergen comprises, or preferably consists of, a protein with an amino acid sequence of at least 92% amino acid sequence identity with SEQ ID NO:17, SEQ ID NO:18; SEQ ID NO:19, SEQ ID NO:20, SEQ ID NO:22 or SEQ ID NO:30. In a preferred embodiment, said at least one peanut allergen comprises, or preferably consists of, a protein with an amino acid sequence of at least 95% amino acid sequence identity with SEQ ID NO:17, SEQ ID NO:18; SEQ ID NO:19, SEQ ID NO:20, SEQ ID NO:22 or SEQ ID NO:30. In a preferred embodiment, said at least one peanut allergen comprises, or preferably consists of, a protein with an amino acid sequence of at least 98% amino acid sequence identity with SEQ ID NO:17, SEQ ID NO:18; SEQ ID NO:19, SEQ ID NO:20, SEQ ID NO:22 or SEQ ID NO:30.

In a very preferred embodiment, said at least one peanut allergen comprises, or preferably consists of, a protein with the amino sequence selected from SEQ ID NO:17, SEQ ID NO:18; SEQ ID NO:19, SEQ ID NO:20, SEQ ID NO:22 or SEQ ID NO:30. In a very preferred embodiment, said at least one peanut allergen comprises, or preferably consists of, a protein with the amino sequence of SEQ ID NO:17. In a very preferred embodiment, said at least one peanut allergen comprises, or preferably consists of, a protein with the amino sequence of SEQ ID NO:18. In a very preferred embodiment, said at least one peanut allergen comprises, or preferably consists of, a protein with the amino sequence of SEQ ID NO:19. In a very preferred embodiment, said at least one peanut allergen comprises, or preferably consists of, a protein with the amino sequence of SEQ ID NO:20. In a very preferred embodiment, said at least one peanut allergen comprises, or preferably consists of, a protein with the amino sequence of SEQ ID NO:22. In a very preferred embodiment, said at least one peanut allergen comprises, or preferably consists of, a protein with the amino sequence of SEQ ID NO:30.

In a further very preferred embodiment, said second attachment site is a sulfhydryl group, and wherein preferably said sulfhydryl group is derived from reaction of said at least one peanut allergen with N-succinimidyl S-acetylthioacetate (SATA) or a derivative thereof, preferably wherein said sulfhydryl group is derived from reaction of said at least one peanut allergen with N-succinimidyl S-acetylthioacetate (SATA). In a further very preferred embodiment, said second attachment site is a sulfhydryl group, and wherein preferably said sulfhydryl group is derived from reaction of a lysine residue of said at least one peanut allergen.

In a further preferred embodiment, the present invention provides for a composition comprising (a) a modified virus-like particle (VLP) with at least one first attachment site, wherein said modified VLP is a modified VLP of cucumber mosaic virus (CMV), wherein said modified CMV polypeptide comprises, preferably consists of, an amino acid sequence of SEQ ID NO:6 or SEQ ID NO:7; (b) at least one peanut allergen with at least one second attachment site, wherein said at least one peanut allergen comprises, or preferably consists of, a protein with the amino sequence selected from SEQ ID NO:17, SEQ ID NO:18; SEQ ID NO:19, SEQ ID NO:20, SEQ ID NO:22 or SEQ ID NO:30, or an isoform thereof, or a protein with an amino acid sequence of at least 90%, preferably of at least 92%, further preferably of at least 95%, and again further preferably of at least 98% amino acid sequence identity with SEQ ID NO:17, SEQ ID NO:18; SEQ ID NO:19, SEQ ID NO:20, SEQ ID NO:22 or SEQ ID NO:30, or an isoform thereof, and again further preferably said at least one peanut allergen comprises, or preferably consists of a protein with the amino sequence of SEQ ID NO:17, SEQ ID NO:18; SEQ ID NO:19, SEQ ID NO:20, SEQ ID NO:22 or SEQ ID NO:30, or an isoform thereof, and again further preferably wherein said at least one peanut allergen comprises, or preferably consists of, a protein with the amino sequence of SEQ ID NO:18, an isoform thereof, or of a protein with an amino acid sequence of at least 90%, preferably of at least 92%, further preferably of at least 95%, and again further preferably of at least 98% amino acid sequence identity with SEQ ID NO:18; wherein (a) and (b) are linked through said at least one first and said at least one second attachment site via at least one non-peptide covalent bond. In a further very preferred embodiment, said second attachment site is a sulfhydryl group, and wherein preferably said sulfhydryl group is derived from reaction of said at least one peanut allergen with N-succinimidyl S-acetylthioacetate (SATA). In a further very preferred embodiment, said second attachment site is a sulfhydryl group, and wherein preferably said sulfhydryl group is derived from reaction of a lysine residue of said at least one peanut allergen.

EXAMPLES

Example 1

Isolation and Cloning of a Coat Protein (CP) of Cucumber Mosaic Virus (CMV)

Total RNA from CMV-infected lily leaves was isolated using TRI reagent (Sigma, Saint Louis, USA) in accordance with manufacturer's instructions. For cDNA synthesis, a OneStep RT-PCR kit (Qiagen, Venlo, Netherlands) was used. For amplification of the CMV CP gene, primer sequences were chosen following analysis of CMV sequences from GenBank: CMcpF (CAC-CATGGACAAATCTGAATCAACCAGTGCTGGT) (SEQ ID NO:8) and CMcpR (CAAAGCTTATCAAACTGG-GAGCACCCCAGATGTGGGA) (SEQ ID NO:9); NcoI and HindIII sites are underlined. The corresponding PCR products were cloned into the pTZ57R/T vector (Fermentas, Vilnius, Lithuania). *E. coli* XL1-Blue cells were used as a host for cloning and plasmid amplification. To avoid selecting clones containing PCR errors, several CP gene-containing pTZ57 plasmid clones were sequenced using a BigDye cycle sequencing kit and an ABI Prism 3100 Genetic analyzer (Applied Biosystems, Carlsbad, USA). After sequencing, a cDNA of the CMV CP gene without sequence errors (SEQ ID NO:10) coding for CMV coat protein of SEQ ID NO:1 was then subcloned into the NcoI/HindIII sites of the pET28a(+) expression vector (Novagen, San Diego, USA), resulting in the expression plasmid pET-CMVwt (FIG. 1).

Example 2

Expression of CP of SEQ ID NO:1 in *E. coli* Leading to VLPs of CMV

To obtain CMV VLPs, *E. coli* C2566 cells (New England Biolabs, Ipswich, USA) were transformed with the CMV CP gene-containing plasmid pET-CMVwt. After selection of clones with the highest expression levels of target protein, *E. coli* cultures were grown in 2×TY medium containing kanamycin (25 mg/l) on a rotary shaker (200 rev/min; Infors, Bottmingen, Switzerland) at 30° C. to an OD600 of 0.8-1.0. Then, the cells were induced with 0.2 mM IPTG, and the medium was supplemented with 5 mM MgCl2. Incubation was continued on the rotary shaker at 20° C. for 18 h. The resulting biomass was collected by low-speed centrifugation and was frozen at −20° C. After thawing on ice, the cells were suspended in the buffer containing 50 mM sodium citrate, 5 mM sodium borate, 5 mM EDTA, 5 mM mercaptoethanol (pH 9.0, buffer A) and were disrupted by ultrasonic treatment. Insoluble proteins and cell debris were removed by centrifugation (13,000 rpm, 30 min at 5° C.). The soluble CMV CP protein in clarified lysate was pelleted using saturated ammonium sulfate (1:1, vol/vol) overnight at +4° C. Precipitated proteins were solubilized in the same buffer A (without mercaptoethanol) for 4 h at +4° C. Insoluble proteins were removed by low speed centrifugation (13,000 rpm, 15 min at 4° C.). Soluble CMV CP-containing protein solution was separated from the cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% Triton X-100). The gradient was divided into six fractions, starting at the bottom of the gradient, and the fractions were analyzed by SDS-PAGE (data not shown). Fractions No. 2 and No. 3 containing recombinant CMV CP were combined and were dialyzed against 200 volumes of the buffer (5 mM sodium borate, 2 mM EDTA, pH 9.0) to remove the sucrose and Triton X-100. After dialysis, CMV CP solution was sterilized by filtration through the 0.2µ filter. Next, CMV CP was concentrated using Type70 rotor (Beckman, Palo Alto, USA) ultracentrifugation through the 20% sucrose "cushion" under sterile conditions (50 000 rpm, 4 h, +5° C.). The concentration of purified CMVwt was estimated using the QuBit fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels.

CMV coat protein can be successfully expressed in *E. coli* cells and significant part obtained can be in soluble fraction. Moreover, these proteins are found directly in *E. coli* cell extracts in the form of isometric VLPs, as demonstrated by sucrose gradient analysis (FIG. 2A), dynamic light scattering and electron-microscopy analysis (FIG. 2B).

Example 3

Cloning of a Modified Coat Protein of CMV Containing a Tetanus Toxoid Epitope (CMV-Ntt830)

To replace the original amino acids at the N-terminus of CMV CP of SEQ ID NO:1 with the tetanus toxoid epitope coding sequence, the pET-CMVwt plasmid was used for PCR amplification and mutagenesis. A SalI site located within the CMVwt gene (FIG. 1) was used for cloning the corresponding PCR products.

To introduce the tetanus toxoid epitope coding sequence into the CMVwt gene, a two step PCR mutagenesis was used. For the first step amplification, the following primers were used: pET-220 (AGCACCGCCGCCGCAAGGAA (SEQ ID NO:11)-upstream from polylinker, the amplified region includes BglII site) and CMV-tt83-1R (ATTTG-GAGTTGGCCTTAATATACTGGCC-CATGGTATATCTCCTTCTTAAAGT) (SEQ ID NO:12). For the second round, the PCR product from the first amplification was diluted 1:50 and re-amplified with primers pET-220 (SEQ ID NO: 11) and CMV-tt83Sa1-R2 (GACGTCGACGCTCGGTAATCCCGATAAATTTG-GAGTTGGCCTTAATATACTG) (SEQ ID NO:13). The resulting PCR product (cDNA of SEQ ID NO:14 coding for CMV-Ntt830 of SEQ ID NO:6) was subcloned in BglII/SaLI sites of pET-CMVwt. The correct clone was identified by sequencing and designated pET-CMV-Ntt830.

Example 4

Expression of CMV-Ntt830 in *E. coli* Leading to Modified VLPs of CMV

To obtain CMV-Ntt830 VLPs, *E. coli* C2566 cells (New England Biolabs, Ipswich, USA) were transformed with the CMV-Ntt830 gene-containing plasmid pET-CMV-Ntt830. After selection of clones with the highest expression levels of target protein, *E. coli* cultures were grown in 2×TY medium containing kanamycin (25 mg/l) in a rotary shaker (200 rev/min; Infors, Bottmingen, Switzerland) at 30° C. to an OD600 of 0.8-1.0. The, cells were then induced with 0.2 mM IPTG, and the medium supplemented with 5 mM $MgCl_2$. Incubation was continued on the rotary shaker at 20° C. for 18 h. The resulting biomass was collected by low-speed centrifugation and frozen at −20° C. After thawing on ice, the cells were suspended in buffer containing 50 mM sodium citrate, 5 mM sodium borate, 5 mM EDTA, 5 mM mercaptoethanol (pH 9.0, buffer A) and disrupted by sonication. Insoluble proteins and cell debris were removed by centrifugation (13,000 rpm, 30 min at 5° C.). The soluble CMV-Ntt830 protein in clarified lysate was pelleted using saturated ammonium sulfate (1:1, vol/vol) overnight at +4° C. Precipitated proteins were solubilized in the buffer A (without mercaptoethanol) for 4 h at +4° C. Insoluble proteins were removed by low speed centrifugation (13,000 rpm, 15 min at 4° C.). Soluble CMV-Ntt830-containing protein solution was separated from cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% Triton X-100). The gradient was divided into six fractions, starting at the bottom of the gradient. Fractions containing recombinant CMV-Ntt830 were combined and dialyzed against 200 volumes of 5 mM sodium borate, 2 mM EDTA (pH 9.0) to remove the sucrose and Triton X-100. After dialysis, CMV-Ntt830 solution was sterilized by filtration through a 0.2µ filter. Next, CMV-Ntt830 was concentrated using Type70 rotor (Beckman, Palo Alto, USA) ultracentrifugation through the 20% sucrose "cushion" under sterile conditions (50 000 rpm, 4 h, +5° C.). The concentration of purified CMV-Ntt830 was estimated using the QuBit fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels. To demonstrate the presence of the tetanus toxoid epitope in CMV VLPs, mass spectrometric analysis of the purified CMV-Ntt830 VLPs was used. As shown in FIG. 3C, the major peak obtained corresponds to the theoretical molecular mass of the protein if the first methionine is removed which occurs during protein synthesis in *E. coli* cells. Dynamic light scattering and electron microscopy confirmed isometric particle morphology similar to CMVwt VLPs (FIGS. 4A and 4B).

Example 5

Cloning of a Modified Coat Protein of CMV Containing a PADRE Epitope (CMV-Npadr)

To introduce the PADRE epitope coding sequence in CMVwt gene, PCR mutagenesis was carried out using as the template for amplification and subcloning the pET-CMVwt plasmid (see also Example 2 and 3). For the amplification following primers were used: pET-220 (SEQ ID NO: 11) and CMV-padrSal-R (GACGTCGACGCGCGGCCGCCTT-GAGGGTCCACGC GGCCACAAATTTCGCCATGGT) (SEQ ID NO:15). The resulting PCR product (cDNA of SEQ ID NO:16 coding for CMV-Npadr of SEQ ID NO:7) was again subcloned in BglII/SalI sites of pET-CMVwt. The correct clone was identified by sequencing and designated as pET-CMV-Npadr.

Example 6

Expression of CMV-Npadr in *E. coli* Leading to Modified VLPs of CMV

The procedures for expression and purification of CMV-Npadr were essentially the same as for CMV-Ntt830 and are described in Example 4. To demonstrate the presence of the PADRE epitope in CMV VLPs, the mass spectrometric analysis of the purified CMV-Npadr VLPs was used. As shown in FIG. 3B, the major peak obtained corresponds to the theoretical molecular mass of the protein if the first methionine is removed which occurs during protein synthesis in *E. coli* cells. Dynamic light scattering and electron microscopy analysis confirmed isometric particle morphology, (FIG. 5A and FIG. 5B).

Example 7

Preparation of Peanut Extracts

The preparation has been conducted According to the protocol by Koppelman et al. (Koppelman et al., Food Chem Toxicol (2016), May; 91:82-90. doi: 10.1016/j.fct.2016.02.016. Epub 2016 Feb. 26)

Native and roasted peeled peanuts were ground using mortar and the pestle. As a source of roasted, salted peanuts, Felix peanuts (produced by Intersnack, Poland) were used.

4 g of resulting peanut mass was extracted with 40 ml buffer (Tris/HCl pH 8, 20 mM and 1 mM EDTA) overnight, +4° C., rotator (10 rpm). The extract was centrifuged in the Sarstedt 50 ml-tubes at 4,500 rpm (2,600×g) for 30 min at 4° C. Then, the middle layer between insoluble peanut mass (bottom) and the lipid layer (on the top) was carefully taken and transferred into new tube (50 ml; Sarstedt). The centrifugation and middle layer collection was repeated.

Figure 6:
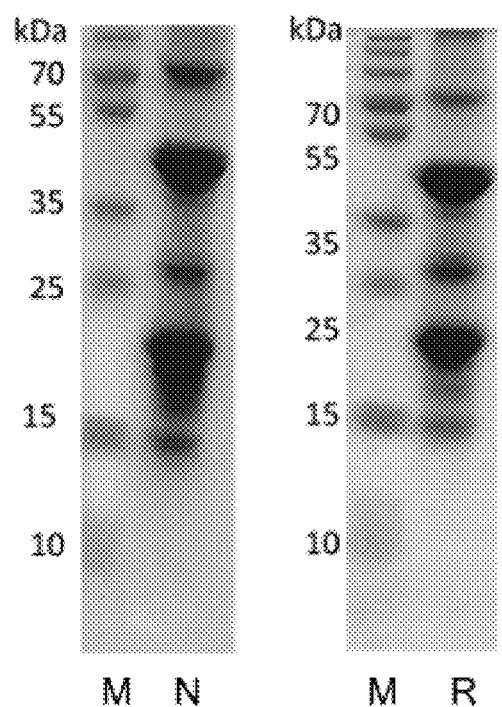
FIG. 6 SDS/PAGE analysis of peanut extracts. M—protein size marker (Thermo Scientific, #26619); N—extract from native peanuts; R—extract from roasted, salted peanuts.

Finally, the extracts was transferred in 50 ml polycarbonate tube (Beckman) and centrifuged at 11000, +4° C., 30 min. The middle layer-supernatant was collected again, aliquoted and frozen in at −70° C. The SDS/PAGE analysis is shown in FIG. 6.

Example 8

Coupling of Peanut Extracts to CMV VLPs

Total proteins of native or roasted peanuts are modified using $SAT(PEG)_4$ (PEGylated N-succinimidyl S-acetylthioacetate; Thermo Fischer, #26099) according to manufacturer's protocol. 300 μl of corresponding peanut extract (approx. 10 mg/ml, in 1×PBS, pH 7.2) was reacted with 50× molar excess of $SAT(PEG)_4$ at room temperature for 30 min. The unreacted $SAT(PEG)_4$ was removed by 4 washing steps using Amicon Ultra-0.5 10K filtration units (Merck-Millipore, Cat. No. UFC501024). Then, the deacetylation step was proceeded for generation of free sulfhydryl groups with deacetylation solution (0.5 M Hydroxylamine, 25 mM EDTA in 1×PBS, pH 7.2; Thermo Scientific, #26103; 30 μl for 300 μl reaction). Then, unreacted hydroxylamine is removed by buffer exchange using Amicon Ultra-0.5 10K filtration units.

Figure 7:
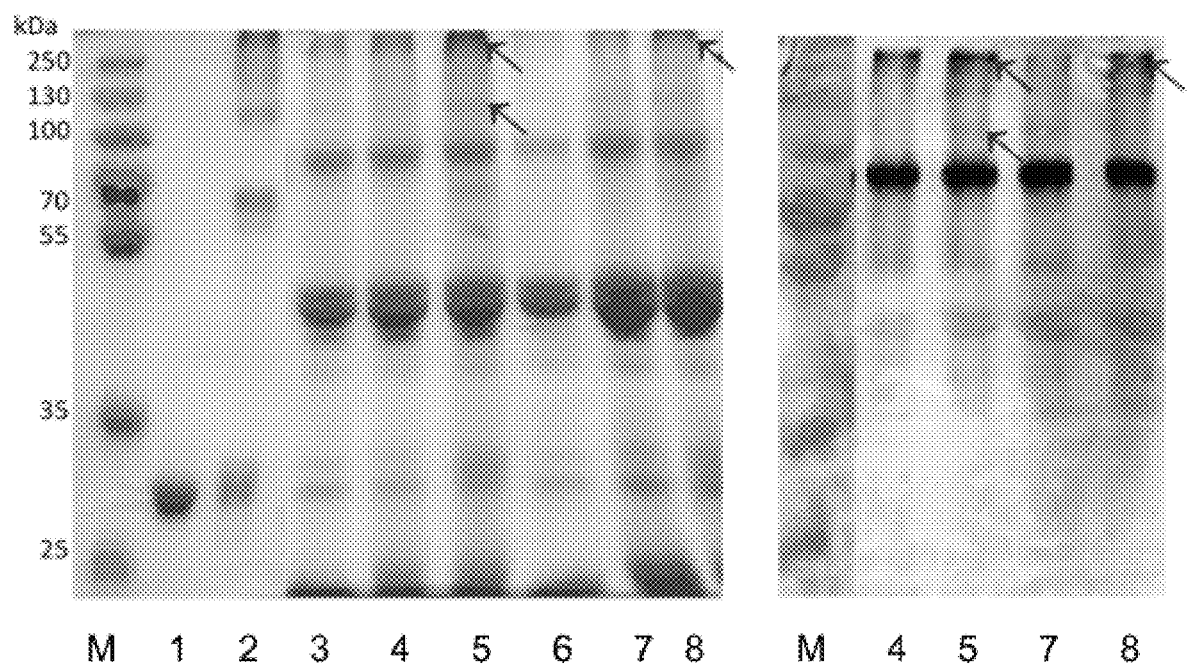
FIG. 7 SDS/PAGE and Western blot analysis of coupling procedure of total proteins of native or roasted peanuts to CMV-Ntt830 VLPs. M—protein size marker (Thermo Scientific, #26619); 1—CMV-Ntt830 VLPs; 2—CMV after derivatization with 10×SMPH and removal of SMPH; 3—total proteins from native peanuts (AraN), without modification; 4—AraN after SAT(PEG)$_4$ modification; 5—CMV-Ntt30 VLPs after coupling with AraN; 6—total proteins from roasted peanuts (AraR), without modification; 7—AraR after SAT(PEG)$_4$ modification; 8—CMV-Ntt30 VLPs after coupling with AraR. Polyclonal anti-Ara h1 antibodies (Indoor Biotechnologies, produced in rabbits) were used as primary antibodies (1:3000) for Western blot, sec FIG. 12B Mass spectrometric analysis of purified Ara-h202-nhk protein. Theoretical Mw (average mass) for Ara-h202-nhk—18877.6 Da, experimentally found 18880.7 Da for refolded and purified Ara-h202-nhk.

CMV-Ntt830 VLPs (1.5 mg/ml; 20 mM Na phosphate, 2 mM EDTA) were first derivatized with 10-fold excess of a heterobifunctional chemical cross-liker, succinimidyl-6-(maleimidopropionamido)hexanoate (SMPH). The unbound SMPH was removed by Amicon Ultra-0.5 10K filtration units. Then, SMPH-derivatized CMV VLPs (1.1 mg/ml; 100 μl) were reacted with $SAT(PEG)_4$-modified peanut extracts (approx. 5 mg/ml; 75 μl) at 22° C. for 3 h. SDS/PAGE and Western blot analysis of coupling procedure of total proteins of native or roasted peanuts to CMV-Ntt830 VLPs is shown in FIG. 7.

Example 9

Purification of Ara h1 from Native Peanuts

To 20 ml of native peanut extract (in 20 mM Tris/HCl pH 8, 1 mM EDTA; approx 10 mg/ml protein) 20 ml of 4 M ammonium sulfate solution was added and incubated on ice for 1 h, then centrifuged 15 min at 5000 rpm (+5° C., Eppendorf #5418). The pellet was discarded. To the supernatant 12.0 g of solid ammonium sulfate was added (end conc. of ammonium sulfate: 4.5 M). The solution was incubated 16 h at +5° C. on the rotator. The pellet was collected by centrifugation (15 min; 10 000 rpm). The protein fraction was further solubilized in 20 ml of 20 mM Na phosphate pH 7.5, rotate (10 rpm) 4 h at +5° C.

For column chromatography, first the Ara h1 containing solution was desalted in Sephadex G25 column. Then, the Ara h1 containing fractions were loaded into Sepharose Q HP column (XK16/20) and eluted with NaCl gradient (0-1 M in 50 mM Tris/Cl buffer, pH 7.6). Ara h1 fractions were identified by SDS/PAGE, pooled and concentrated to approx. 2 ml, using Amicon Ultra-15 (cutoff 10 kDa).

Finally, residual impurities were separated from Ara h1 using Superdex 200 column (XK16/70). Ara h1 containing fractions were pooled and concentrated again. The final preparation (approx. 2 mg/ml) was used in subsequent coupling reactions or kept at −70° C.

Example 10

Coupling of Peanut Allergen Ara h1 to CMV VLPs

Purified Ara h1 protein from native peanuts was modified using SATA (N-succinimidyl S-acetylthioacetate; Thermo Fischer, #26102) to introduce additional sulfhydryl groups according to manufacturer's protocol. 100 μl of Ara h1 (approx. 2 mg/ml, in 1×PBS, pH 7.2) was reacted with 10× molar excess of SATA at room temperature for 30 min. The unreacted SATA was removed by 4 washing steps using Amicon Ultra-0.5 10K filtration units (Merck-Millipore, Cat. No. UFC501024). Then, the deacetylation step was proceeded for generation of free sulfhydryl groups with deacetylation solution (0.5 M Hydroxylamine, 25 mM EDTA in 1×PBS, pH 7.2; Thermo Scientific, #26103; 30 μl for 300 μl reaction). Further, residual hydroxylamine was removed by buffer exchange using Amicon Ultra-0.5 10K filtration units.

Figure 8:
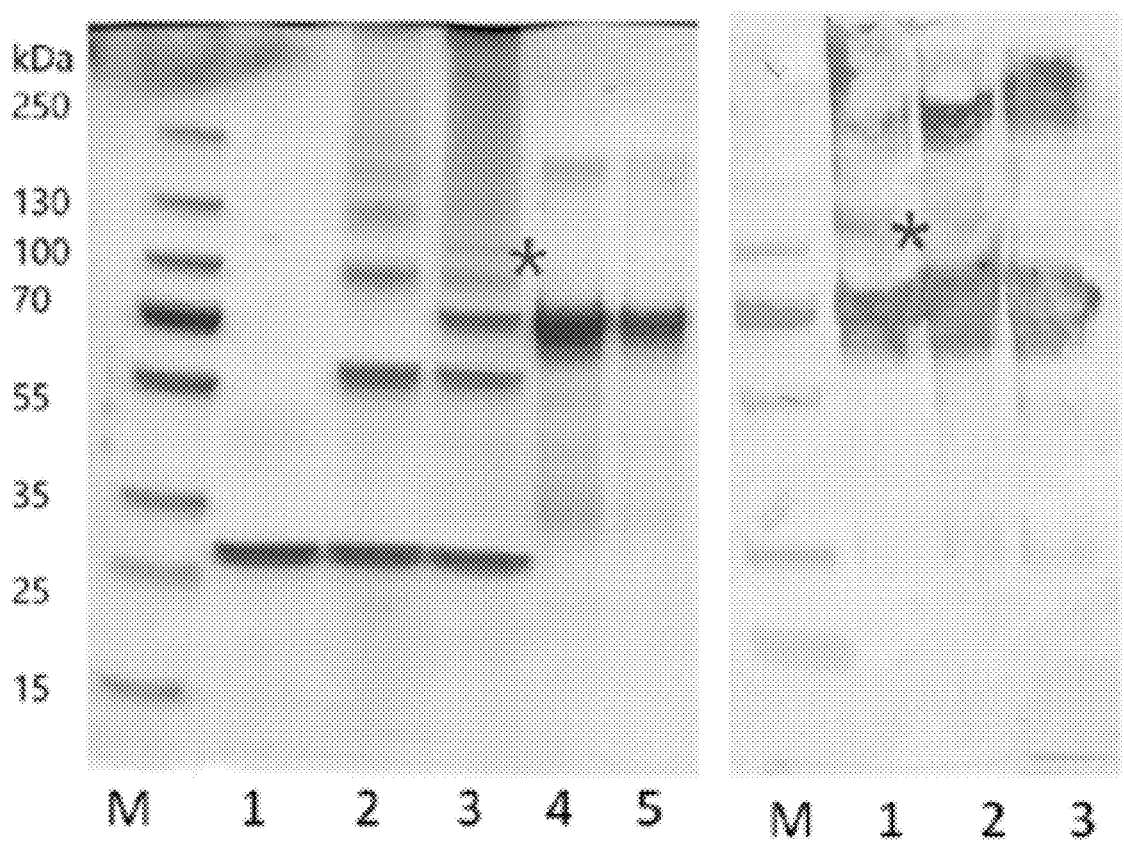
Figure 9:
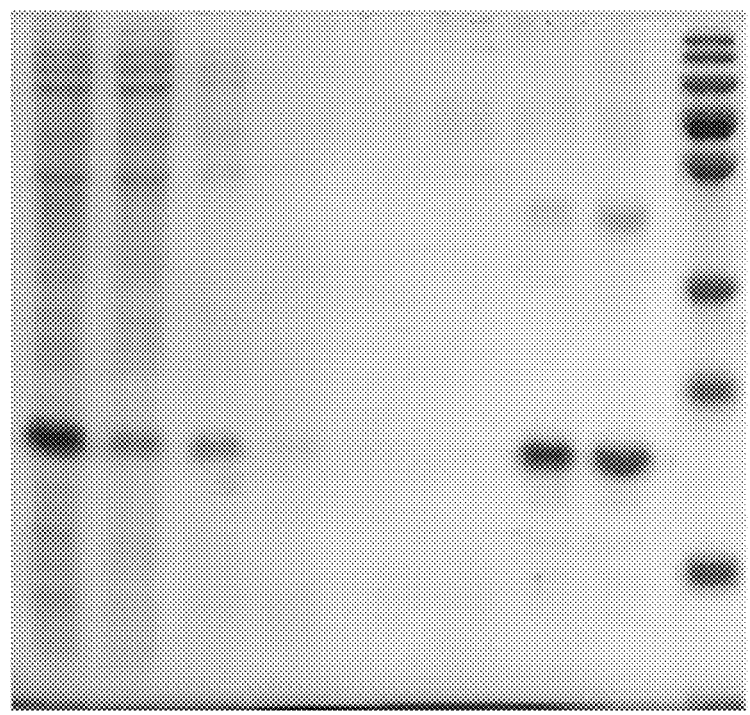
Figure 10:
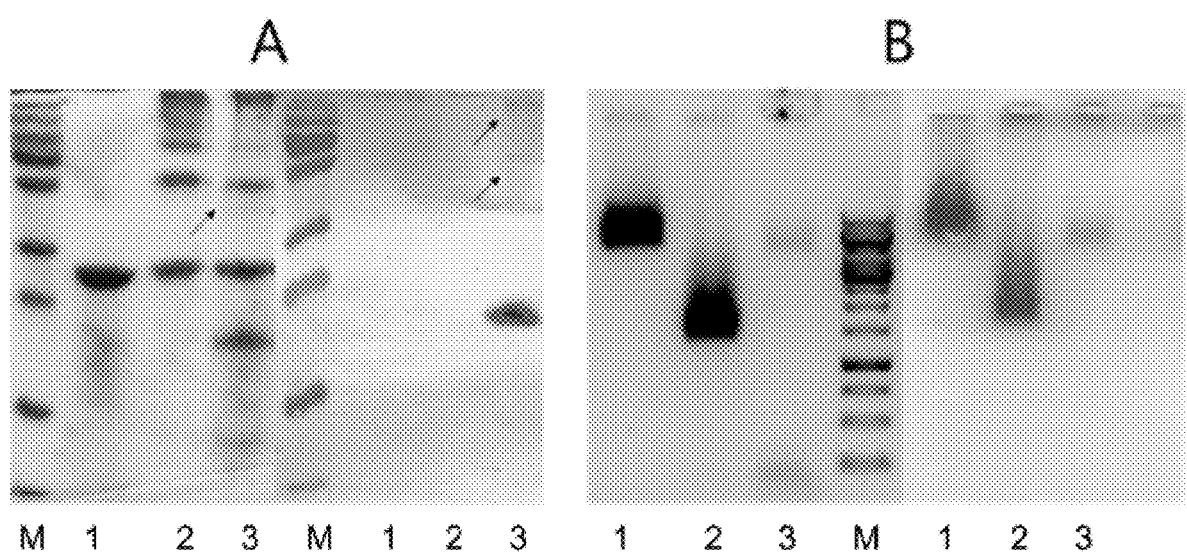
Figure 11A:
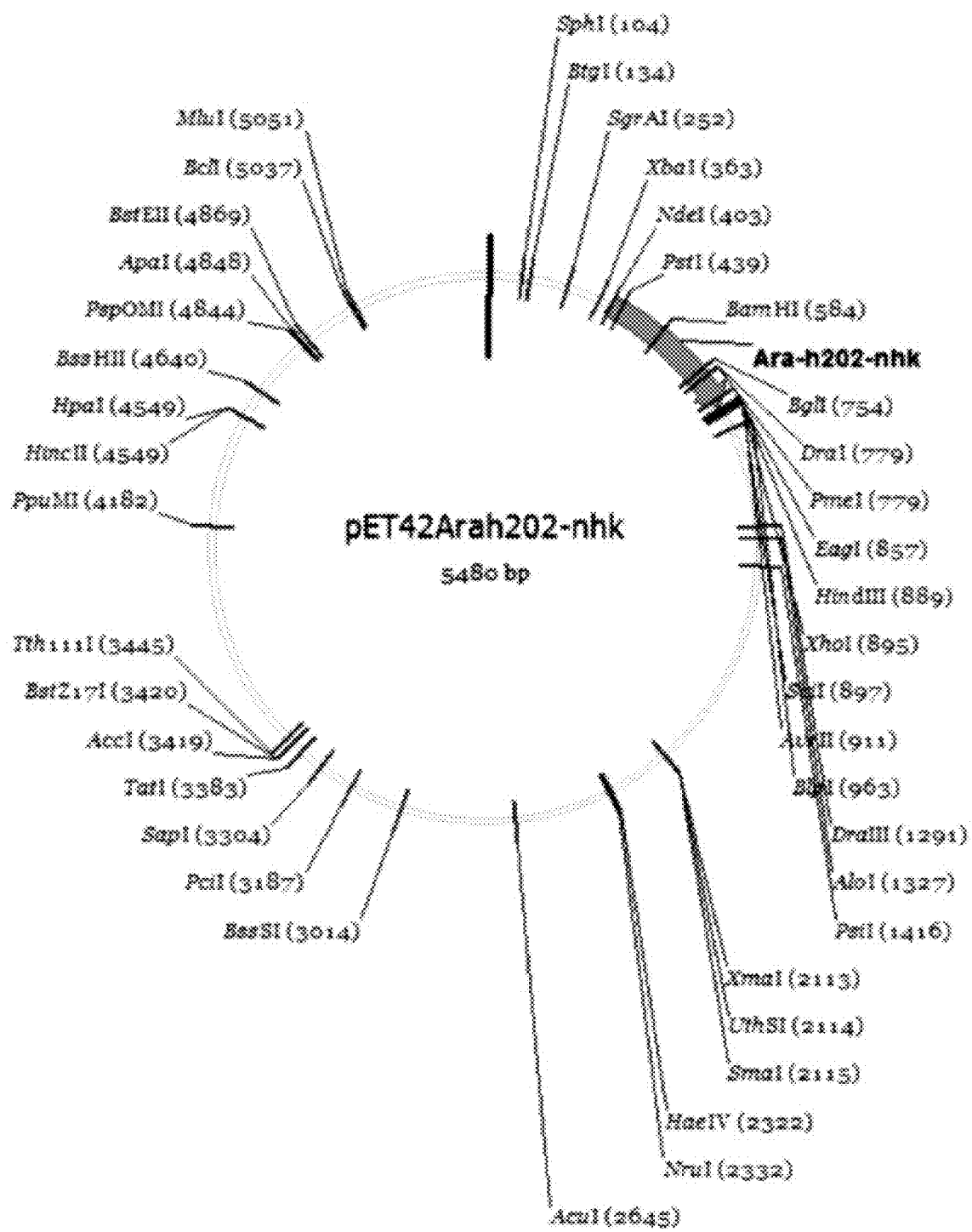

CMV-Ntt830 VLPs (1.5 mg/ml; 20 mM Na phosphate, 2 mM EDTA) were first derivatized with 10-fold excess of a heterobifunctional chemical cross-liker, succinimidyl-6-(maleimidopropionamido)hexanoate (SMPH). The unbound SMPH was removed by Amicon Ultra-0.5 10K filtration units. Then, SMPH-derivatized CMV VLPs (1.1 mg/ml; 100 μl) were reacted with 0.3× molar amount of SATA-modified Ara h1 (approx. 5 mg/ml; 75 μl) at 22° C. for 3 h. SDS/PAGE and Western blot analysis is shown in FIG. 8.

Example 11

Expression and Purification of Ara-h202 Fusion Protein

An Ara-h202 fusion protein gene coding for three "dpysps"-motifs (long version) and a hexahistine sequence and additional Cys at the 5'end of the gene was produced by oligonucleotide directed gene synthesis. The corresponding nucleotide sequence has the sequence of SEQ ID NO:21, wherein the protein sequence of Ara-h202 has the sequence of SEQ ID NO:22. After synthesis of the gene, it was excised from its helper plasmid and subcloned in frame into NcoI/XhoI sites of the plasmid pET28a(+) (Novagen, USA) resulting in the expression vector pET-n6H-Ara-h202. The hexa-histidine sequence enables purification by metal chelate affinity chromatography and the N-terminal sequence comprising MGC enables the coupling of the Ara-h202 fusion protein to CMV-Ntt830 VLPs.

The Ara-h202-expression vector pET-n6H-Ara-h202 was introduced into *E. coli* C2566 cells (New England Biolabs, Ipswich, USA) via transformation. Clones expressing the highest levels of target protein were selected and kept for further experiments. Expression of the Ara-h202 fusion protein was performed in the following way: Cultures of *E. coli* harboring expression plasmids were grown in 2×TY medium containing kanamycin (25 mg/l) on a rotary shaker (200 rev/min; Infors, Bottmingen, Switzerland) at 30° C. to an OD600 of 0.8-1.0. Expression of the Ara-h202 fusion protein genes was then induced by adding 0.2 mM IPTG. The medium was supplemented with 5 mM MgCl$_2$. Incubation was continued on a rotary shaker at 20° C. for 18 h. The resulting biomass was collected by low-speed centrifugation and frozen at −20° C. until purification.

For purification of Ara-h202 fusion protein, the USB PrepEase Kit for purification of His-tagged proteins (Affymetrix, High Wycombe, UK) was used according to manufacturer's instructions. After thawing on ice, *E. coli* cells (approx. 1.0 g) were suspended in 1×LEW buffer. Then, the cells were disrupted by ultrasonication (8 min; amplitude 70%, pulse 0.5; Hielscher UP200S device). Insoluble proteins were collected by centrifugation (13,000 rpm, 30 min at 5° C.) and resuspended in 10 mL of extraction buffer (1×LEW, 4 M urea, 5 mM dithiothreitol), sonicated (4 min, the same conditions), then mixed for 2 hours on a rotary mixer at room temperature to solubilize inclusion bodies. The solution was clarified by 5 min centrifugation at 14000 rpm and applied to a Ni-IDA column. The washing, renaturation and elution of the Ara-h202 protein from Ni-IDA column was performed as follows:

wash with 1×LEW containing 2 M urea+30% glycerol;
wash with 1×LEW containing 1 M urea+30% glycerol;
wash with 1×LEW containing 0.5 M urea+30% glycerol;
wash with 1×LEW containing 0 M urea+30% glycerol;
Elute with 1×E buffer containing 30% glycerol.

Figure 12A:
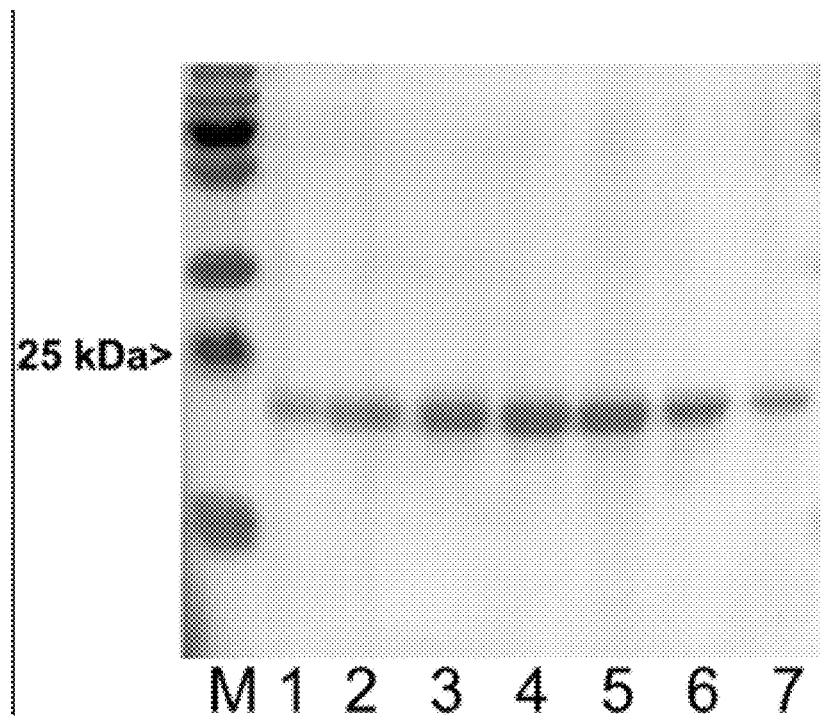
Figure 12B:
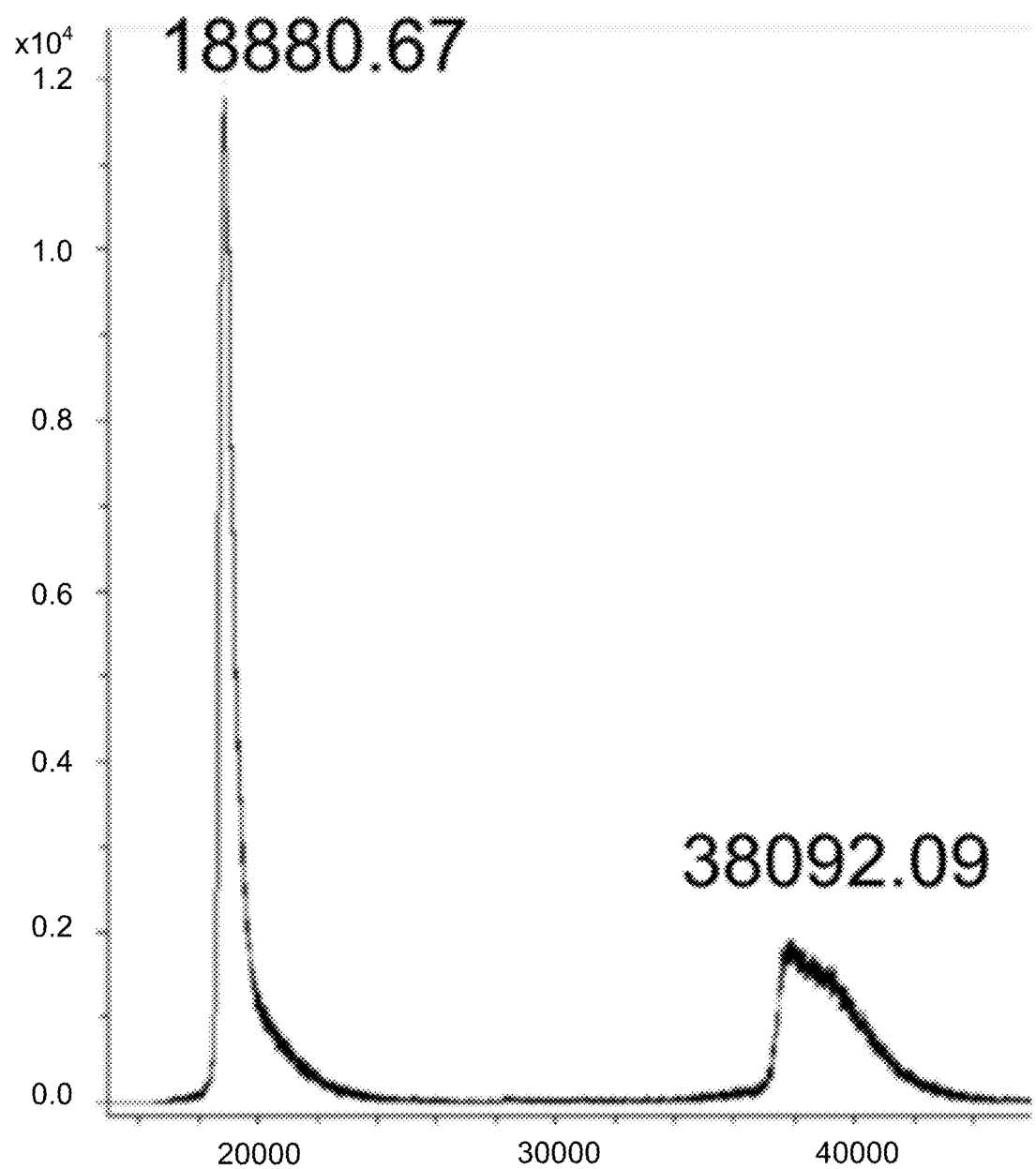
Figure 13A:
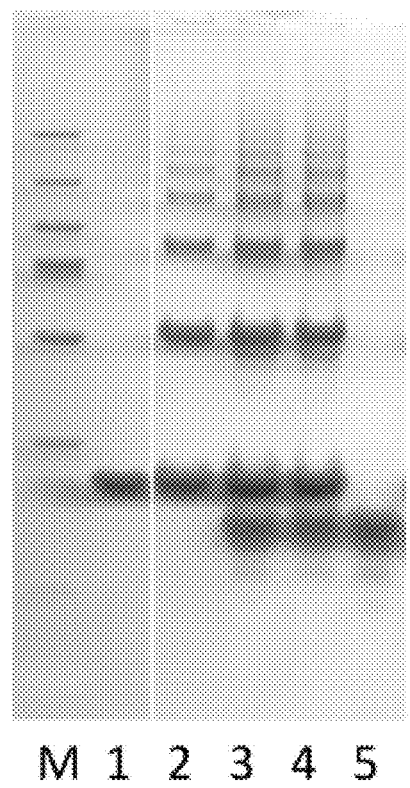
FIG. 13A SDS-PAGE analysis.
Figure 13B:
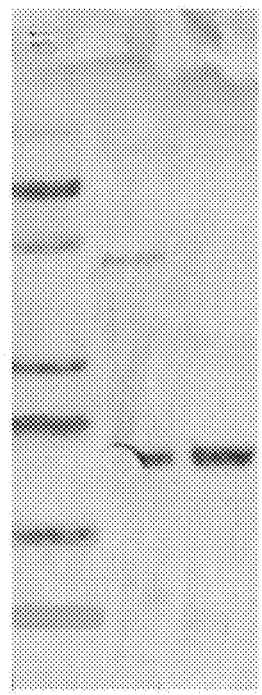
FIG. 13B Western blot analysis. M—protein size marker (Thermo Scientific, #242877); column 1—CMV-Ntt830; column2—CMV-Ntt830 after derivatization with SMPH and removal of SMPH; column 3—coupling product CMV+Ara-h202-nhk; column 4—coupling product CMV+Ara-h202-nhk after 48 h incubation at +4° C.; column 5—SATA modified Ara-h202-nhk.
Figure 14A:
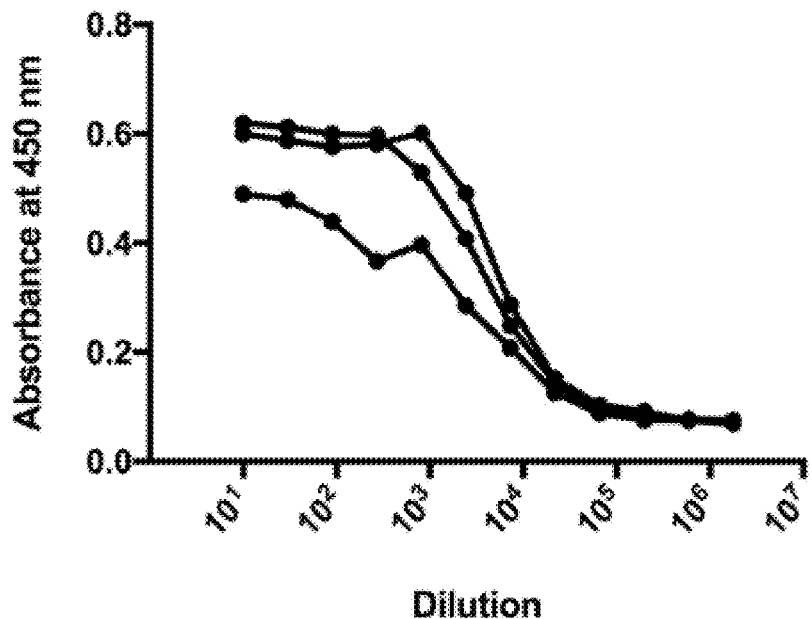
FIG. 14 For determination of antigen-specific IgG, ELISA plates were coated either with roasted peanut extract (for mice vaccinated with CMV-Ntt830-AraR, FIG. 14A) or Ara-h202-nhk (for mice vaccinated with CMV-Ntt830-Ara-h202-nhk, FIG. 14B) or Ara h1 (for mice vaccinated with CMV-Ntt830-Ara h1, FIG. 14C). Serial dilutions of mice sera (n=3) at day 7 (FIG. 14C) or 14 (FIG. 14A, B) were added to the plates. Antibodies were detected with horse-radish peroxidase (HRP) conjugated anti-mouse IgG.
Figure 14B:
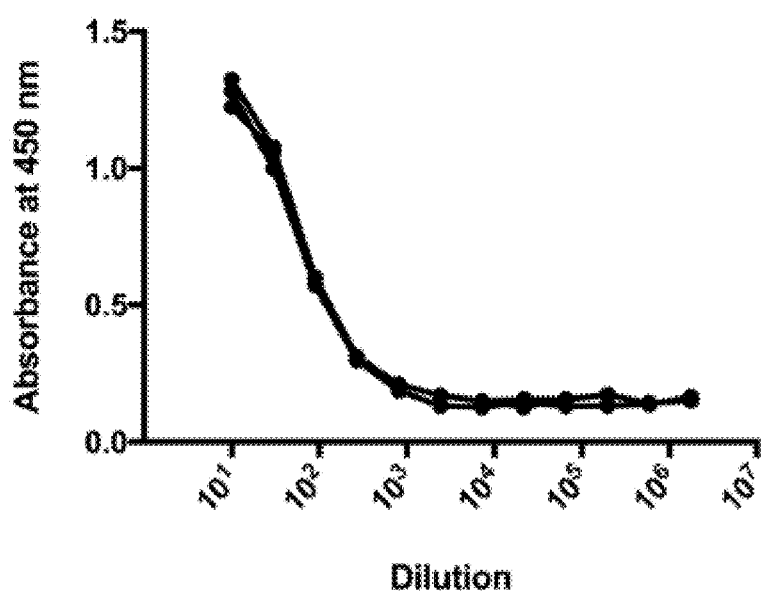
Figure 14C:
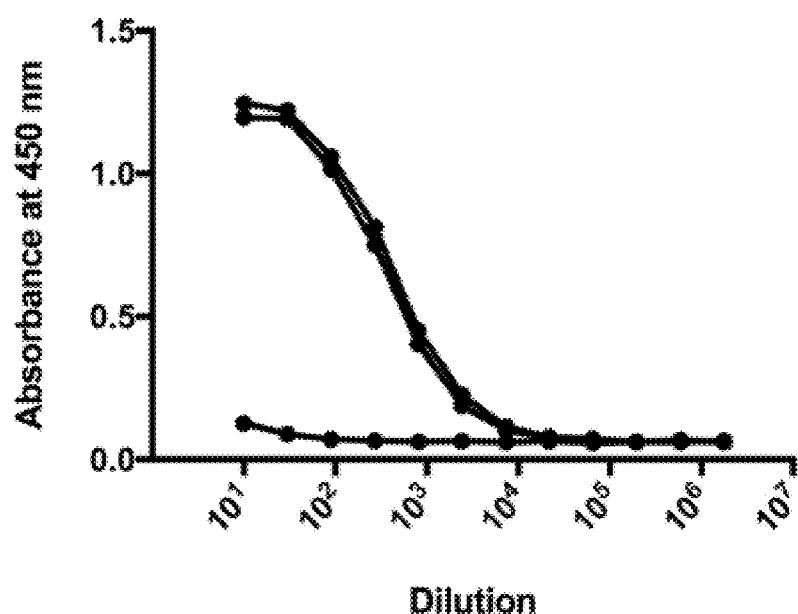
Figure 15A:
FIG. 15 Assessment of efficacy of vaccine: Mice were sensitized with roasted peanut extract at day 0, 7 and 14. At day 28 mice were vaccinated, at day 42 challenged with roasted peanut extract (FIG. 15A). Temperature changes (° C.)±SED (n=5) are shown in CMV or CMV-Ara R (FIG. 15B), CMV-Ara h202 nhk (FIG. 15C) or CMV Ara h1 (FIG. 15D).
Figure 15A:
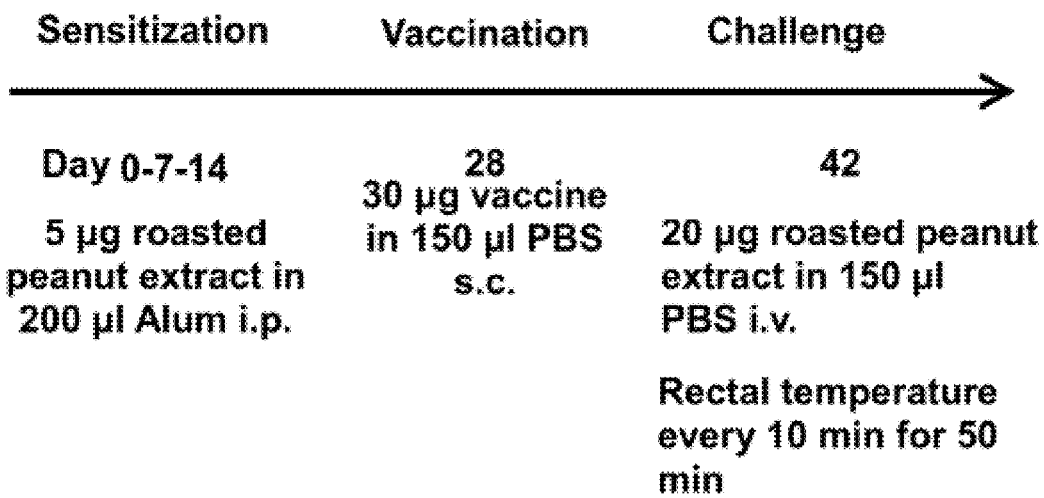
Figure 15B:
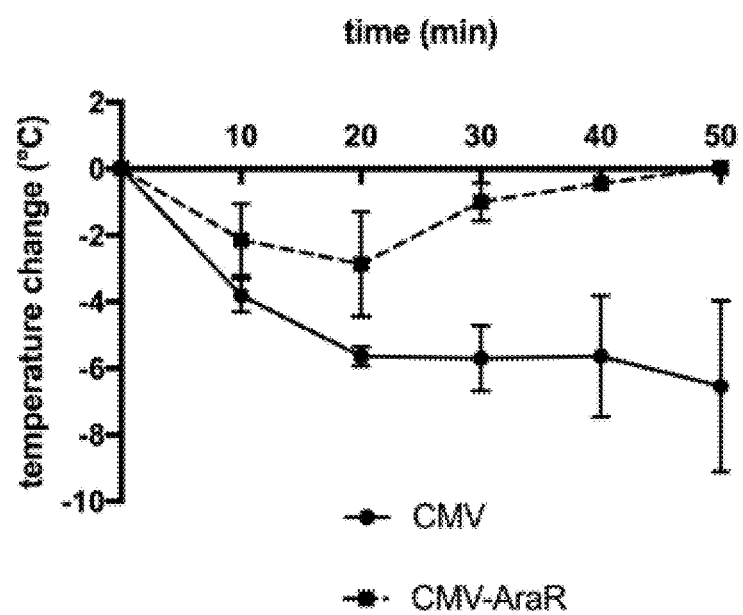
Figure 15C:
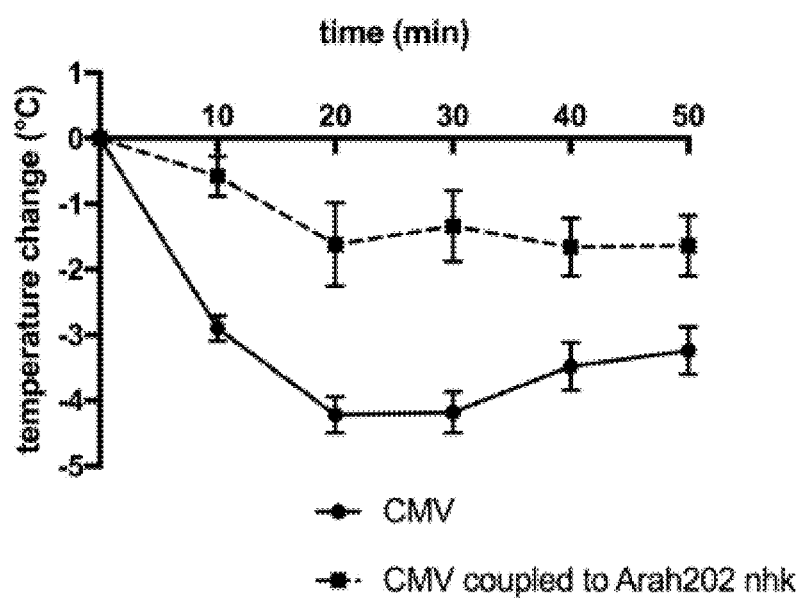
Figure 15D:
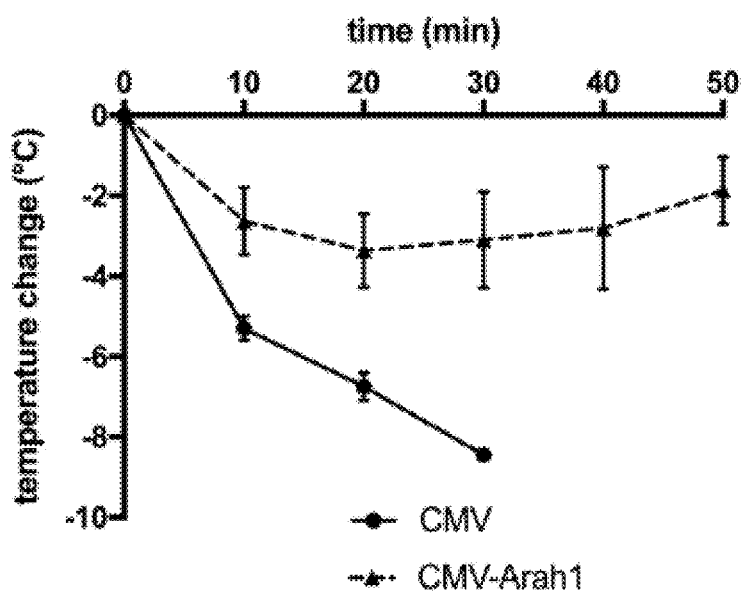

The fractions containing Ara-h202 were identified by SDS/PAGE and twice dialyzed against 50 volumes of the 1×LEW buffer containing 30% glycerol. After dialysis, the protein concentration was estimated using a QuBit fluorometer in accordance with manufacturer's instructions (Invitrogen, Eugene, USA) or by UV spectrophotometric measurement at 280 nm. Purified and refolded Ara-h202 was used in subsequent coupling reactions with CMV-Ntt830 VLPs. SDS/PAGE analysis of purification and refolding of Ara-h202 from *E. coli* C2566 cells is shown in FIG. 9.

Example 12

Coupling of Recombinant Ara-h202 Fusion Protein to CMV VLPs

Coupling of the recombinant Ara-h202 (SEQ ID NO:22) to the CMV-Ntt830 VLPs was performed as follows. To reduce the introduced Cys-residues and facilitate the coupling the refolded Ara-h202 was reduced for 1 h with a 10× excess of tri(2-carboxyethyl)phosphine hydrochloride (TCEP) in PBS (pH 8.0). Reduced Ara-h202 (20 μM) was incubated for 4 h at 22° C. with 45 μM of SMPH derivatized CMV-Ntt830. The reaction was dialysed 12 h against PBS pH 8.0. SDS/PAGE and Western blot analysis is shown in FIG. 10.

Example 13

Expression and Purification of Ara-h202 Protein

The codon-adapted gene encoding Ara-h202 protein (GenBank Seq.ID: AAM78596) was synthesized by IDT (Integrated DNA Technologies, Leuven, Belgium). The gene synthesis product (plasmid pUCIDT-Ara-h202) was used as a template for PCR reaction to amplify the Ara-h202 gene coding for additional Lys residue at protein N-terminus for SATA modification and additional Cys residue at C-terminus for SMPH modification. Following oligonucleotides were used for PCR amplification:

```
Ara-h202-nhkF:
                                        (SEQ ID NO: 31)
ACACATATGAATCATAAAGTGCGCCAGCAGTGGGAACTGCA Ara-h2-cgR:
                                        (SEQ ID NO: 32)
TGCTCGAGAAGCTTATTATCCACAACCACCATAGCGATCACGGCCGC
CGCT
```

After amplification of the Ara-h202-nhk gene, the PCR product was directly ligated into the pTZ57R/T vector. *E. coli* XL1-Blue cells were used as a host for transformation and plasmid amplification. To avoid PCR errors, several Ara-h202 gene-containing pTZ57 plasmid clones were sequenced using a BigDye cycle sequencing kit and an ABI Prism 3100 Genetic Analyser (Applied Biosystems). After sequencing, the cDNA of Ara-h202-nhk gene without sequence errors was then subcloned into the NdeI/XhoI sites of the pET42 expression vector (Novagen), resulting in the expression plasmid pET42-Ara-h202-nhk. A detailed description of resulting expression vector can be found in FIG. 11A-C.

To obtain Ara-h202-nhk protein, *E. coli* C2566 (New England Biolabs, USA) competent cells were transformed with the plasmid pET42-Ara-h202-nhk. After selection of clones with the highest expression level of target protein, *E. coli* cultures were grown in 2TY (Trypton 1.6%, yeast extract 1%, 0.5% NaCl, 0.1% glucose) medium containing kanamycin (25 mg/l) on a rotary shaker at 30° C. to the OD(600) value of 0.8-1.0. Then, the cells were induced with 0.2 mM IPTG, and the medium was supplemented with 5 mM $MgCl_2$. Incubation was continued on the rotary shaker at 20° C. for 18 h. The resulting biomass was collected by low-speed centrifugation and frozen at −20° C. The output of biomass was approx. 10 g wet biomass from 1 liter of culture, the OD(600) was approx. 6.0 at the end of cultivation. Ara-h202-nhk protein was purified as follows:

1) Suspension of 1.9 g of biomass in 10 ml of buffer (20 mM Tris/HCl 7.5, 1 mM EDTA, 0.1 mM PMSF, 0.1% TX-100, DNAse I (30 ug/10 ml), RNAse (0.5 mg/10 ml).
2) Treatment of the suspension with ultrasound for 16 min (Hielscher sonicator UP200S, Amplitude 70%, cycle 0.5).
3) Addition of additional 10 ml of the same buffer, mix on rotating mixer (60 min, room temperature, 10 rpm).
4) Centrifugation of the sample at 11000 rpm, 30 min (Eppendorf 5810R, rotor F-34-6-38) to collect insoluble inclusion bodies which contain Ara-h202 protein.
5) Inclusion bodies were solubilized in 10 ml of the following buffer: 6M guanidine-HCl; 100 mM NaCl; 5 mM EDTA; 10 mM DTT; 20 mM Tris 8.5, mixing using rotating mixer (10 rpm) overnight at room temperature.
6) Centrifugation of the sample at 11000 rpm, 30 min (Eppendorf 5810R, rotor F-34-6-38).
7) Slow (drop by drop) addition of the Ara-h202-nhk containing supernatant (10 ml) to the refolding buffer (110 ml; 0.1M CAPS pH 9.5, 0.9 M arginine, 0.3 mM reduced and 0.03 mM oxidized glutathione) and overnight incubation at room temperature; without mixing.
8) At the next day, dialysis of the refolding mixture (approx. 120 ml) against 2000 ml of buffer containing 20 mM Tris-HCl, 50 mM NaCl (overnight, +4° C.) using SpectraPor dialysis membrane (6-8 kDa, #132 655).
9) Centrifugation of the dialysate 11000 rpm, 30 min (Eppendorf 5810R);
10) Dilution of the sample to 300 ml with 50 mM Tris (pH 8.0) and loading of the solution onto anion-exchanger Sepharose Q HP (XK16/20 column), elution of the proteins with 1M NaCl in 50 mM Tris-HCl (pH 8.0);
11) Pooling of the Ara-h202 containing fractions and concentration to approx. 2 ml using Amicon Ultra-15 (cutoff 10 kDa).
12) Finally, purification of the Ara-h202-nhk on Superdex 200 column, pooling of the Ara-h202-nhk fractions, concentration to approx. 1 mg/ml and analysis of the samples using SDS-PAGE and mass spectrometry analysis (FIG. 12A, B).

Example 14

Coupling of Recombinant Ara-h202 to CMV VLPs

Refolded and purified Ara-h202-nhk protein was modified using SATA (N-succinimidyl S-acetylthioacetate; Thermo Fischer, #26102) to introduce additional sulfhydryl groups according to the manufacturer's protocol. 1.3 ml of Ara-h202-nhk (0.72 mg/ml, in 1×PBS, pH 7.2) was reacted with 4× molar excess of SATA at room temperature for 30 min. The unreacted SATA was removed by four washing steps using Amicon Ultra-0.5 (10K) filtration units (Merck-Millipore, Cat. No. UFC501024). Then, the deacetylation step was proceeded for generation of free sulfhydryl groups with deacetylation solution (0.5 M Hydroxylamine, 25 mM EDTA in 1×PBS, pH 7.2; Thermo Scientific, #26103; 30 μl for 300 μl reaction). Further, residual hydroxylamine was removed by buffer exchange using Amicon Ultra-0.5 10K filtration units.

CMV-Ntt830 VLPs (1.5 mg/ml; 20 mM Na phosphate, 2 mM EDTA) were first derivatized with 2.5-fold excess of a heterobifunctional chemical cross-linker, succinimidyl-6-(maleimidopropionamido)hexanoate (SMPH). The unbound SMPH was removed by Amicon Ultra-0.5 10K filtration units. Then, SMPH-derivatized CMV VLPs (1.1 mg/ml; 430 μl) were reacted with 2-fold molar amount of SATA-modified Ara-h202-nhk (4.7 mg/ml; 200 μl) at 22° C. for 3 h. SDS/PAGE and Western blot analysis is shown in FIG. 13.

Example 15

Vaccination Against Peanut Allergy

1. Methods 1.1 Immunogenicity of Vaccine—Antigen Specific IgG

Vaccination. Naive BALB/c mice (3 mice per group) were vaccinated with 30 μg CMV-Ntt830-AraR (CMV-Ntt830 VLPs coupled to roasted peanut extract as described in Example 8) or CMV-Ara-h202-nhk (CMV-Ntt830 VLPs coupled to Ara-h202-nhk as described in Example 14) or CMV-Ntt830-Ara h1 (CMV-Ntt830 VLPs coupled to Ara h1 as described in Example 10) in 150 μl PBS subcutaneously. After 7 or 14 days sera were collected and antigen-specific ELISA was performed (cf. next paragraph).

Determination of antigen-specific IgG. For determination of antigen-specific IgG, 96-well ELISA plates (fisher scientific) were coated either with 1 μg/ml extract of roasted peanut (for mice vaccinated with CMV-AraR) or Ara-h20-nhk (for mice vaccinated with CMV-Ara-h202-nhk) or Ara h1 (for mice vaccinated with CMV-Ara h1) in PBS at 4° C. overnight. After incubation plates were washed three times with PBS/0.05% Tween and blocked with PBS-casein solution for 2 h, and then plates were washed three times with PBS/0.05% Tween. Serial dilutions of sera were added to the plates and incubated for 2 h at 4°. Plates were washed three times with PBS/0.05% Tween. Thereafter, HRPO-labeled goat anti-mouse IgG (Jackson ImmunoResearch Laboratories) antibodies were incubated at 4° C. for 1 h, followed by addition of the substrate TMB (3,3',5,5'-Tetramethylbenzidine, Sigma-Aldrich). Optical densities were measured at 450 nm (cf. FIGS. 14A-C for ELISA for IgG against roasted peanut extract (A), Ara-h202-nhk (B), CMV-Ara h1 (C)).

1.2 Efficacy of Vaccine—Systemic Anaphylaxis

Sensitization. For peanut sensitization, 6-wk-old BALB/c mice (n=5) were injected i.p. with 5 μg roasted peanut extract (Latvian Biomedical Research & Study Centre, Riga) mixed in 200 μl Alum (10 mg/ml Al(OH)3; Alhydrogel adjuvant 2%) at day 0, 7 and 14.

Vaccination. At day 28, mice were vaccinated s.c. with 30 μg vaccine (respectively CMV for control group, CMV coupled to Ara-h202-nhk, CMV coupled to Ara h1 or CMV coupled to AraR for vaccinated groups) (Latvian Biomedical Research & Study Centre, Riga) in 150 μl PBS.

Acute systemic anaphylaxis. For induction of anaphylaxis, sensitized and vaccinated mice were challenged i.v. with 20 μg roasted peanut extract in 150 μl PBS at day 42. Temperature was measured with a rectal probe digital thermometer (MiniTemp, Vetronic Services LTD) directly before i.v. antigen challenge and monitored for 50 min every 10 min after injection. Temperature drop under 30° C. or severe signs of anaphylaxis were indications for euthanasia.

Detailed experimental design to assess efficacy of a vaccine. Mice were sensitized with 5 μg roasted peanut extract i.p. at day 0, 7 and 14. At day 28 mice were vaccinated s.c. with 30 μg vaccine (respectively CMV for control group, CMV coupled to Arah-202-nhk, CMV coupled to Ara h1 or CMV coupled to Ara R for vaccinated groups). At day 42 mice were challenged intravenously with 20 μg roasted peanut extract in 150 μl PBS (FIG. 15A). Temperature changes (° C.)±SED (n=5) are shown in CMV or CMV-Ara R (FIG. 15B), CMV-Ara-h202-nhk (FIG. 15C) or CMV Ara h1 (FIG. 15D).

2. Results 2.1 Vaccination with CMV-AraR, CMV-Ara-h202-nhk and CMV-Ara h1 is Able to Induce Antigen-Specific IgG Response in Mice Allergen-specific IgG production is a central mechanism of vaccine-based desensitization (Nicole Schmitz et al., 2009, Displaying Fel d1 on virus-like particles prevents reactogenicity despite greatly enhanced immunogenicity: A novel therapy for cat allergy). To assess immunogenicity of vaccine consisting of CMV-AraR, CMV-Ara-h202-nhk or CMV-Ara h1, ELISA plates were coated respectively with extract of roasted peanut, Ara-h202-nhk and Ara h1 and incubated with mice sera 7 or 14 days after vaccination. Specific IgG levels were detected with HRP conjugated anti-mouse IgG. As shown in FIGS. 14A, B and C, these three vaccines are able to induce a specific IgG production in mice.

2.2 Vaccination with CMV-AraR, CMV-Ara-h202-nhk or CMV-Ara h1 Protects Against Systemic Anaphylaxis To investigate whether vaccine based on CMV coupled to the extract of roasted peanut, Ara-h202-nhk or Ara h1 were able to desensitize allergic mice, roasted peanut-sensitized BALB/c mice (n=5) were vaccinated once subcutaneously with CMV-AraR, CMV-Ara-h202-nhk or CMV-Ara h1 (FIG. 15A-D). As a control CMV alone was injected. 14 days after vaccination, mice were challenged i.v. with 20 μg of roasted peanut extract. Control groups showed an anaphylactic reaction with temperature drop (in case of severe anaphylactic reaction mice had to be euthanized, FIG. 15D, CMV line). Vaccinated mice showed clearly protection due to the vaccine.

---

The invention claimed is:

1. A composition comprising (a) a modified virus-like particle (VLP) of cucumber mosaic virus (CMV) with at least one first attachment site, wherein said modified VLP of CMV comprises at least one modified CMV polypeptide, wherein said modified CMV polypeptide comprises a) a CMV polypeptide, and b) a T helper cell epitope, wherein said T helper cell epitope replaces a N-terminal region of said CMV polypeptide, and wherein said N-terminal region of said CMV polypeptide corresponds to amino acids 2-12 of SEQ ID NO:1, wherein said CMV polypeptide comprises (i) an amino acid sequence of a coat protein of CMV; or (ii) an amino acid sequence having a sequence identity of at least 90% to said coat protein of CMV; and (b) at least one peanut allergen with at least one second attachment site, wherein said peanut allergen consists of a protein consisting of the amino acid sequence of SEQ ID NO:18;

wherein (a) and (b) are linked through said at least one first and said at least one second attachment site via at least one non-peptide covalent bond.

2. The composition of claim 1, wherein said virus-like particle (VLP) is a recombinant VLP.

3. The composition of claim 1, wherein said CMV polypeptide comprises (a) an amino acid sequence of a coat protein of CMV, wherein said amino acid sequence comprises SEQ ID NO:1 or (b) an amino acid sequence having a sequence identity of at least 90% of SEQ ID NO:1; and wherein said amino sequence as defined in (a) or (b) in this claim comprises SEQ ID NO:23; or wherein said amino acid sequence as defined in (a) or (b) in this claim comprises an amino acid sequence region, wherein said amino acid sequence region has a sequence identity of at least 90% with SEQ ID NO:23.

4. The composition of claim 1, wherein said Th cell epitope is a PADRE sequence, and wherein said Th cell epitope comprises the amino acid sequence of SEQ ID NO:5; or wherein said Th cell epitope is derived from tetanus toxin, and wherein said Th cell epitope has the amino acid sequence of SEQ ID NO:4.

5. The composition of claim 1, wherein said CMV polypeptide comprises an amino acid sequence of a coat protein of CMV, wherein said amino acid sequence comprises SEQ ID NO:1 or an amino acid sequence having a sequence identity of at least 95% of SEQ ID NO:1; and wherein said amino acid sequence comprises SEQ ID NO:23, and wherein said T helper cell epitope replaces the N-terminal region of said CMV polypeptide, and wherein said replaced N-terminal region of said CMV polypeptide consists of 11 to 13 consecutive amino acids.

6. The composition of claim 1, wherein said modified CMV polypeptide comprises an amino acid sequence of SEQ ID NO:6 or SEQ ID NO:7.

7. The composition of claim 1, wherein said second attachment site is a sulfhydryl group.

8. The composition of claim 7, wherein said sulfhydryl group is derived from reaction of said at least one peanut allergen with N-succinimidyl S-acetylthioacetate (SATA) or a derivative thereof.

9. A pharmaceutical composition comprising (a) a composition of claim 1;

(b) a pharmaceutically acceptable carrier.

10. A method of preventing or treating peanut allergy in a human, wherein an effective amount of a composition is administered to said human, wherein said composition is a composition of claim 1 optionally comprising a pharmaceutically acceptable carrier.

11. The composition of claim 5, wherein said T helper cell epitope replaces the N-terminal region of said CMV polypeptide, and wherein said replaced N-terminal region of said CMV polypeptide consists of 11 consecutive amino acids.

12. The composition of claim 11, wherein said N-terminal region of said CMV polypeptide corresponds to amino acids 2-12 of SEQ ID NO:1.

13. A composition comprising (a) a modified virus-like particle (VLP) of cucumber mosaic virus (CMV) with at least one first attachment site, wherein said modified VLP of CMV comprises at least one modified CMV polypeptide, wherein said modified CMV polypeptide comprises a) a CMV polypeptide, and b) a T helper cell epitope, wherein said T helper cell epitope replaces a N-terminal region of said CMV polypeptide, and wherein said N-terminal region of said CMV polypeptide corresponds to amino acids 2-12 of SEQ ID NO:1, wherein said CMV polypeptide comprises (i) an amino acid sequence of a coat protein of CMV; or (ii) an amino acid sequence having a sequence identity of at least 90% to said coat protein of CMV; and (b) at least one peanut allergen with at least one second attachment site, wherein said peanut allergen consists of a protein with the amino acid sequence of SEQ ID NO: 22; wherein (a) and (b) are linked through said at least one first and said at least one second attachment site via at least one non-peptide covalent bond.

14. A composition comprising (a) a modified virus-like particle (VLP) of cucumber mosaic virus (CMV) with at least one first attachment site, wherein said modified VLP of CMV comprises at least one modified CMV polypeptide, wherein said modified CMV polypeptide comprises a) a CMV polypeptide, and b) a T helper cell epitope, wherein said T helper cell epitope replaces a N-terminal region of said CMV polypeptide, and wherein said N-terminal region of said CMV polypeptide corresponds to amino acids 2-12 of SEQ ID NO:1, wherein said CMV polypeptide comprises (i) an amino acid sequence of a coat protein of CMV; or (ii) an amino acid sequence having a sequence identity of at least 90% to said coat protein of CMV; and (b) at least one peanut allergen with at least one second attachment site, wherein said peanut allergen consists of a protein with the amino acid sequence of SEQ ID NO: 30; wherein (a) and (b) are linked through said at least one first and said at least one second attachment site via at least one non-peptide covalent bond.

15. The composition of claim 13, wherein said modified CMV polypeptide comprises an amino acid sequence of SEQ ID NO:6.

16. The composition of claim 13, wherein said modified CMV polypeptide comprises an amino acid sequence of SEQ ID NO:7.

17. The composition of claim 14, wherein said modified CMV polypeptide comprises an amino acid sequence of SEQ ID NO:6.

18. The composition of claim 14, wherein said modified CMV polypeptide comprises an amino acid sequence of SEQ ID NO:7.

19. A pharmaceutical composition comprising
(a) a composition of claim 15;
(b) a pharmaceutically acceptable carrier.

20. A pharmaceutical composition comprising
(a) a composition of claim 17;
(b) a pharmaceutically acceptable carrier.

* * * * *

SEQUENCE LISTING

```
<160> NUMBER OF SEQ ID NOS: 32

<210> SEQ ID NO 1
<211> LENGTH: 218
<212> TYPE: PRT
<213> ORGANISM: cucumber mosaic virus

<400> SEQUENCE: 1

Met Asp Lys Ser Glu Ser Thr Ser Ala Gly Arg Ser Arg Arg Arg
1               5                   10                  15

Pro Arg Arg Gly Ser Arg Ser Ala Pro Ser Ser Ala Asp Ala Asn Phe
                20                  25                  30

Arg Val Leu Ser Gln Gln Leu Ser Arg Leu Asn Lys Thr Leu Ala Ala
            35                  40                  45

Gly Arg Pro Thr Ile Asn His Pro Thr Phe Val Gly Ser Glu Arg Cys
    50                  55                  60

Lys Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
    130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Val Glu His Gln
        195                 200                 205

Arg Ile Pro Thr Ser Gly Val Leu Pro Val
    210                 215

<210> SEQ ID NO 2
<211> LENGTH: 217
<212> TYPE: PRT
<213> ORGANISM: cucumber mosaic virus

<400> SEQUENCE: 2

Asp Lys Ser Glu Ser Thr Ser Ala Gly Arg Asn Arg Arg Arg Arg Pro
1               5                   10                  15

Arg Arg Gly Ser Arg Ser Ala Ser Ser Ala Asp Ala Asn Phe Arg
                20                  25                  30

Val Leu Ser Gln Gln Leu Ser Arg Leu Asn Lys Thr Leu Ala Ala Gly
            35                  40                  45
```

```
Arg Pro Thr Ile Asn His Pro Thr Phe Val Gly Ser Glu Arg Cys Lys
 50                  55                  60

Pro Gly Tyr Thr Phe Ser Ser Ile Thr Leu Lys Pro Pro Lys Ile Asp
 65                  70                  75                  80

Arg Gly Ser Tyr Tyr Gly Lys Arg Leu Leu Leu Pro Asp Ser Val Thr
                 85                  90                  95

Glu Phe Asp Lys Lys Leu Val Ser Arg Ile Gln Ile Arg Val Asn Pro
                100                 105                 110

Leu Pro Lys Phe Asp Ser Thr Val Trp Val Thr Val Arg Lys Val Pro
            115                 120                 125

Ala Ser Ser Asp Leu Ser Val Ala Ala Ile Ser Ala Met Phe Ala Asp
130                 135                 140

Gly Ala Ser Pro Val Leu Val Tyr Gln Tyr Ala Ala Ser Gly Val Gln
145                 150                 155                 160

Ala Asn Asn Lys Leu Leu Tyr Asp Leu Ser Ala Met Arg Ala Asp Ile
                165                 170                 175

Gly Asp Met Arg Lys Tyr Ala Val Leu Val Tyr Ser Lys Asp Asp Ala
                180                 185                 190

Leu Glu Thr Asp Glu Leu Val Leu His Val Asp Ile Glu His Gln Arg
            195                 200                 205

Ile Pro Thr Ser Gly Val Leu Pro Val
            210                 215
```

<210> SEQ ID NO 3
<211> LENGTH: 218
<212> TYPE: PRT
<213> ORGANISM: cucumber mosaic virus

<400> SEQUENCE: 3

```
Met Asp Lys Ser Glu Ser Pro Asn Ala Ser Arg Thr Ser Arg Arg Arg
 1               5                  10                  15

Arg Pro Arg Arg Gly Ser Arg Ser Ala Ser Gly Ala Asp Ala Gly Leu
                 20                  25                  30

Arg Ala Leu Thr Gln Gln Met Leu Lys Leu Asn Lys Thr Leu Ala Ile
             35                  40                  45

Gly Arg Pro Thr Leu Asn His Pro Thr Phe Val Gly Ser Ala Ser Cys
 50                  55                  60

Lys Pro Gly Tyr Thr Phe Thr Ser Ile Thr Leu Lys Pro Pro Glu Ile
 65                  70                  75                  80

Glu Lys Gly Ser Tyr Phe Gly Arg Arg Leu Ser Leu Pro Asp Ser Val
                 85                  90                  95

Thr Asp Tyr Asp Lys Lys Leu Val Ser Arg Ile Gln Ile Arg Ile Asn
                100                 105                 110

Pro Leu Pro Lys Phe Asp Ser Thr Val Trp Val Thr Val Arg Lys Val
            115                 120                 125

Pro Ser Ser Ser Asp Leu Ser Val Ala Thr Ile Ser Ala Met Phe Gly
130                 135                 140

Asp Gly Asn Ser Pro Val Leu Val Tyr Gln Tyr Thr Ala Ser Gly Val
145                 150                 155                 160

Gln Ala Asn Asn Lys Leu Leu Tyr Asp Leu Ser Glu Met Arg Ala Asp
                165                 170                 175

Ile Gly Asp Met Arg Lys Tyr Ala Val Leu Val Tyr Ser Lys Asp Asp
                180                 185                 190
```

```
Lys Leu Glu Glu Asp Glu Ile Val Leu His Val Asp Val Glu His Gln
        195                 200                 205

Arg Ile Pro Ile Ser Arg Met Leu Pro Thr
    210                 215

<210> SEQ ID NO 4
<211> LENGTH: 14
<212> TYPE: PRT
<213> ORGANISM: artificial sequence
<220> FEATURE:
<223> OTHER INFORMATION: tetanus toxoid epitope tt830

<400> SEQUENCE: 4

Gln Tyr Ile Lys Ala Asn Ser Lys Phe Ile Gly Ile Thr Glu
1               5                   10

<210> SEQ ID NO 5
<211> LENGTH: 13
<212> TYPE: PRT
<213> ORGANISM: artificial sequence
<220> FEATURE:
<223> OTHER INFORMATION: PADRE

<400> SEQUENCE: 5

Ala Lys Phe Val Ala Ala Trp Thr Leu Lys Ala Ala Ala
1               5                   10

<210> SEQ ID NO 6
<211> LENGTH: 222
<212> TYPE: PRT
<213> ORGANISM: artificial sequence
<220> FEATURE:
<223> OTHER INFORMATION: CMV-Ntt830

<400> SEQUENCE: 6

Met Gly Gln Tyr Ile Lys Ala Asn Ser Lys Phe Ile Gly Ile Thr Glu
1               5                   10                  15

Arg Arg Arg Arg Pro Arg Arg Gly Ser Arg Ser Ala Pro Ser Ser Ala
            20                  25                  30

Asp Ala Asn Phe Arg Val Leu Ser Gln Gln Leu Ser Arg Leu Asn Lys
        35                  40                  45

Thr Leu Ala Ala Gly Arg Pro Thr Ile Asn His Pro Thr Phe Val Gly
    50                  55                  60

Ser Glu Arg Cys Lys Pro Gly Tyr Thr Phe Thr Ser Ile Thr Leu Lys
65                  70                  75                  80

Pro Pro Lys Ile Asp Arg Gly Ser Tyr Tyr Gly Lys Arg Leu Leu Leu
                85                  90                  95

Pro Asp Ser Val Thr Glu Tyr Asp Lys Lys Leu Val Ser Arg Ile Gln
            100                 105                 110

Ile Arg Val Asn Pro Leu Pro Lys Phe Asp Ser Thr Val Trp Val Thr
        115                 120                 125

Val Arg Lys Val Pro Ala Ser Ser Asp Leu Ser Val Ala Ala Ile Ser
    130                 135                 140

Ala Met Phe Ala Asp Gly Ala Ser Pro Val Leu Val Tyr Gln Tyr Ala
145                 150                 155                 160

Ala Ser Gly Val Gln Ala Asn Asn Lys Leu Leu Tyr Asp Leu Ser Ala
                165                 170                 175

Met Arg Ala Asp Ile Gly Asp Met Arg Lys Tyr Ala Val Leu Val Tyr
            180                 185                 190
```

Ser Lys Asp Asp Ala Leu Glu Thr Asp Glu Leu Val Leu His Val Asp
    195                 200                 205

Val Glu His Gln Arg Ile Pro Thr Ser Gly Val Leu Pro Val
    210                 215                 220

<210> SEQ ID NO 7
<211> LENGTH: 220
<212> TYPE: PRT
<213> ORGANISM: artificial sequence
<220> FEATURE:
<223> OTHER INFORMATION: CMV-Npadr

<400> SEQUENCE: 7

Met Ala Lys Phe Val Ala Ala Trp Thr Leu Lys Ala Ala Arg Arg
1               5                   10                  15

Arg Arg Pro Arg Arg Gly Ser Arg Ser Ala Pro Ser Ser Ala Asp Ala
            20                  25                  30

Asn Phe Arg Val Leu Ser Gln Gln Leu Ser Arg Leu Asn Lys Thr Leu
        35                  40                  45

Ala Ala Gly Arg Pro Thr Ile Asn His Pro Thr Phe Val Gly Ser Glu
    50                  55                  60

Arg Cys Lys Pro Gly Tyr Thr Phe Thr Ser Ile Thr Leu Lys Pro Pro
65                  70                  75                  80

Lys Ile Asp Arg Gly Ser Tyr Tyr Gly Lys Arg Leu Leu Leu Pro Asp
                85                  90                  95

Ser Val Thr Glu Tyr Asp Lys Lys Leu Val Ser Arg Ile Gln Ile Arg
            100                 105                 110

Val Asn Pro Leu Pro Lys Phe Asp Ser Thr Val Trp Val Thr Val Arg
        115                 120                 125

Lys Val Pro Ala Ser Ser Asp Leu Ser Val Ala Ala Ile Ser Ala Met
    130                 135                 140

Phe Ala Asp Gly Ala Ser Pro Val Leu Val Tyr Gln Tyr Ala Ala Ser
145                 150                 155                 160

Gly Val Gln Ala Asn Asn Lys Leu Leu Tyr Asp Leu Ser Ala Met Arg
                165                 170                 175

Ala Asp Ile Gly Asp Met Arg Lys Tyr Ala Val Leu Val Tyr Ser Lys
            180                 185                 190

Asp Asp Ala Leu Glu Thr Asp Glu Leu Val Leu His Val Asp Val Glu
        195                 200                 205

His Gln Arg Ile Pro Thr Ser Gly Val Leu Pro Val
    210                 215                 220

<210> SEQ ID NO 8
<211> LENGTH: 34
<212> TYPE: DNA
<213> ORGANISM: artificial sequence
<220> FEATURE:
<223> OTHER INFORMATION: primer CMcpF

<400> SEQUENCE: 8
caccatggac aaatctgaat caaccagtgc tggt                           34

<210> SEQ ID NO 9
<211> LENGTH: 37
<212> TYPE: DNA
<213> ORGANISM: artificial sequence
<220> FEATURE:
<223> OTHER INFORMATION: primer CMcpR

```
<400> SEQUENCE: 9
caaagcttat caaactggga gcaccccaga tgtggga                              37

<210> SEQ ID NO 10
<211> LENGTH: 660
<212> TYPE: DNA
<213> ORGANISM: cucumber mosaic virus

<400> SEQUENCE: 10
atggacaaat ctgaatcaac cagtgctggt cgtagccgtc gacgtcgtcc gcgtcgtggt    60
tcccgctccg cccctcctc cgcggatgct aactttagag tcttgtcgca gcagctttcg    120
cgacttaata agacgttagc agctggtcgt ccaactatta accacccaac ctttgtaggg    180
agtgaacgct gtaaacctgg gtacacgttc acatctatca ccctaaagcc accaaaaata    240
gaccgtgggt cttattatgg taaaaggttg ttattacctg attcagtcac ggaatatgat    300
aagaaacttg tttcgcgcat tcaaattcga gttaatcctt tgccgaaatt tgattcaacc    360
gtgtgggtga cagtccgtaa agttcctgcc tcttcggact tatccgttgc cgccatttct    420
gctatgtttg cggacggagc ctcaccggta ctggtttatc agtacgctgc atctggagtc    480
caagctaaca caaactgtt gtatgatctt tcggcgatgc cgctgatat aggcgacatg    540 agaaagtacg ccgtcctcgt gtattcaaaa gacgatgcac tcgagacaga cgagttagta    600
cttcatgttg acgtcgagca ccaacgtatt cccacatctg gggtgctccc agtttgataa    660

<210> SEQ ID NO 11
<211> LENGTH: 20
<212> TYPE: DNA
<213> ORGANISM: artificial sequence
<220> FEATURE:
<223> OTHER INFORMATION: primer pET-220

<400> SEQUENCE: 11
agcaccgccg ccgcaaggaa                                                20

<210> SEQ ID NO 12
<211> LENGTH: 52
<212> TYPE: DNA
<213> ORGANISM: artificial sequence
<220> FEATURE:
<223> OTHER INFORMATION: primer CMV-tt83-1R

<400> SEQUENCE: 12
atttggagtt ggccttaata tactggccca tggtatatct ccttcttaaa gt            52

<210> SEQ ID NO 13
<211> LENGTH: 52
<212> TYPE: DNA
<213> ORGANISM: artificial sequence
<220> FEATURE:
<223> OTHER INFORMATION: primer CMV-tt83Sal-R2

<400> SEQUENCE: 13
gacgtcgacg ctcggtaatc ccgataaatt tggagttggc cttaatatac tg            52

<210> SEQ ID NO 14
<211> LENGTH: 672
<212> TYPE: DNA
<213> ORGANISM: artificial sequence
<220> FEATURE:
<223> OTHER INFORMATION: cDNA coding for CMV-Ntt830
```

```
<400> SEQUENCE: 14
atgggccagt atattaaggc caactccaaa tttatcggga ttaccgagcg tcgacgtcgt      60
ccgcgtcgtg gttcccgctc cgcccctcc tccgcggatg ctaactttag agtcttgtcg     120
cagcagcttt cgcgacttaa taagacgtta gcagctggtc gtccaactat taaccaccca     180 accttttgtag ggagtgaacg ctgtaaacct gggtacacgt tcacatctat caccctaaag    240
ccaccaaaaa tagaccgtgg gtcttattat ggtaaaaggt tgttattacc tgattcagtc     300
acggaatatg ataagaaact tgtttcgcgc attcaaattc gagttaatcc tttgccgaaa     360
tttgattcaa ccgtgtgggt gacagtccgt aaagttcctg cctcttcgga cttatccgtt     420
gccgccattt ctgctatgtt tgcggacgga gcctcaccgg tactggttta tcagtacgct     480
gcatctggag tccaagctaa caacaaactg ttgtatgatc tttcggcgat gcgcgctgat     540
ataggcgaca tgagaaagta cgccgtcctc gtgtattcaa agacgatgc actcgagaca      600 gacgagttag tacttcatgt tgacgtcgag caccaacgta ttcccacatc tggggtgctc     660
ccagtttgat aa                                                          672

<210> SEQ ID NO 15
<211> LENGTH: 55
<212> TYPE: DNA
<213> ORGANISM: artificial sequence
<220> FEATURE:
<223> OTHER INFORMATION: primer CMV-padrSal-R

<400> SEQUENCE: 15
gacgtcgacg cgcggccgcc ttgagggtcc acgcggccac aaatttcgcc atggt           55

<210> SEQ ID NO 16
<211> LENGTH: 666
<212> TYPE: DNA
<213> ORGANISM: artificial sequence
<220> FEATURE:
<223> OTHER INFORMATION: cDNA coding for CMV-Npadr

<400> SEQUENCE: 16
atggcgaaat tgtggccgc gtggaccctc aaggcggccg cgcgtcgacg tcgtccgcgt        60
cgtggttccc gctccgcccc ctcctccgcg gatgctaact ttagagtctt gtcgcagcag     120 cttttcgcgac ttaataagac gttagcagct ggtcgtccaa ctattaacca cccaaccttt    180
gtagggagtg aacgctgtaa acctgggtac acgttcacat ctatcaccct aaagccacca    240
aaaatagacc gtgggtctta ttatggtaaa aggttgttat acctgattc agtcacggaa     300 tatgataaga aacttgtttc gcgcattcaa attcgagtta atcctttgcc gaaatttgat    360
tcaaccgtgt gggtgacagt ccgtaaagtt cctgcctctt cggacttatc cgttgccgcc   420
atttctgcta tgtttgcgga cggagcctca ccggtactgg tttatcagta cgctgcatct    480
ggagtccaag ctaacaacaa actgttgtat gatctttcgg cgatgcgcgc tgatataggc    540
gacatgagaa agtacgccgt cctcgtgtat tcaaaagacg atgcactcga gacagacgag   600
ttagtacttc atgttgacgt cgagcaccaa cgtattccca catctggggt gctcccagtt    660
tgataa                                                                 666

<210> SEQ ID NO 17
<211> LENGTH: 626
<212> TYPE: PRT
<213> ORGANISM: artificial sequence
<220> FEATURE:
<223> OTHER INFORMATION: Ara h1
```

```
<400> SEQUENCE: 17

Met Arg Gly Arg Val Ser Pro Leu Met Leu Leu Gly Ile Leu Val
1               5                   10                  15

Leu Ala Ser Val Ser Ala Thr His Ala Lys Ser Pro Tyr Gln Lys
            20                  25                  30

Lys Thr Glu Asn Pro Cys Ala Gln Arg Cys Leu Gln Ser Cys Gln Gln
            35                  40                  45

Glu Pro Asp Asp Leu Lys Gln Lys Ala Cys Ser Arg Cys Thr Lys
50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Arg Arg Gln Pro Arg Arg Glu Glu Gly
            100                 105                 110

Gly Arg Trp Gly Pro Ala Gly Pro Arg Glu Arg Glu Arg Glu Asp
            115                 120                 125

Trp Arg Gln Pro Arg Glu Asp Trp Arg Arg Pro Ser His Gln Gln Pro
130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
            195                 200                 205

Leu Gln Asn His Arg Ile Val Gln Ile Glu Ala Lys Pro Asn Thr Leu
210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
            275                 280                 285

Ser Met Pro Val Asn Thr Pro Gly Gln Phe Glu Asp Phe Phe Pro Ala
290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
            340                 345                 350

Trp Ser Thr Arg Ser Ser Glu Asn Asn Glu Gly Val Ile Val Lys Val
            355                 360                 365

Ser Lys Glu His Val Glu Glu Leu Thr Lys His Ala Lys Ser Val Ser
370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415
```

Val Lys Pro Asp Lys Lys Asn Pro Gln Leu Gln Asp Leu Asp Met Met
            420                 425                 430

Leu Thr Cys Val Glu Ile Lys Glu Gly Ala Leu Met Leu Pro His Phe
            435                 440                 445

Asn Ser Lys Ala Met Val Ile Val Val Asn Lys Gly Thr Gly Asn
            450                 455                 460

Leu Glu Leu Val Ala Val Arg Lys Glu Gln Gln Arg Gly Arg Arg
465                 470                 475                 480

Glu Glu Glu Glu Asp Glu Asp Glu Glu Glu Gly Ser Asn Arg Glu
                485                 490                 495

Val Arg Arg Tyr Thr Ala Arg Leu Lys Glu Gly Asp Val Phe Ile Met
                500                 505                 510

Pro Ala Ala His Pro Val Ala Ile Asn Ala Ser Ser Glu Leu His Leu
                515                 520                 525

Leu Gly Phe Gly Ile Asn Ala Glu Asn Asn His Arg Ile Phe Leu Ala
                530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
                580                 585                 590

Ser Pro Ser Ser Pro Glu Lys Glu Ser Pro Glu Lys Glu Asp Gln Glu
                595                 600                 605

Glu Glu Asn Gln Gly Gly Lys Gly Pro Leu Leu Ser Ile Leu Lys Ala
            610                 615                 620

Phe Asn
625

<210> SEQ ID NO 18
<211> LENGTH: 151
<212> TYPE: PRT
<213> ORGANISM: artificial sequence
<220> FEATURE:
<223> OTHER INFORMATION: Ara-h202

<400> SEQUENCE: 18

Arg Gln Gln Trp Glu Leu Gln Gly Asp Arg Arg Cys Gln Ser Gln Leu
1               5                   10                  15

Glu Arg Ala Asn Leu Arg Pro Cys Glu Gln His Leu Met Gln Lys Ile
            20                  25                  30

Gln Arg Asp Glu Asp Ser Tyr Gly Arg Asp Pro Tyr Ser Pro Ser Gln
        35                  40                  45

Asp Pro Tyr Ser Pro Ser Gln Asp Pro Asp Arg Arg Asp Pro Tyr Ser
50                  55                  60

Pro Ser Pro Tyr Asp Arg Arg Gly Ala Gly Ser Ser Gln His Gln Glu
65                  70                  75                  80

Arg Cys Cys Asn Glu Leu Asn Glu Phe Glu Asn Asn Gln Arg Cys Met
                85                  90                  95

Cys Glu Ala Leu Gln Gln Ile Met Glu Asn Gln Ser Asp Arg Leu Gln
            100                 105                 110

Gly Arg Gln Gln Glu Gln Gln Phe Lys Arg Glu Leu Arg Asn Leu Pro
        115                 120                 125

-continued

```
Gln Gln Cys Gly Leu Arg Ala Pro Gln Arg Cys Asp Leu Glu Val Glu
        130                 135                 140

Ser Gly Gly Arg Asp Arg Tyr
145                 150

<210> SEQ ID NO 19
<211> LENGTH: 530
<212> TYPE: PRT
<213> ORGANISM: artificial sequence
<220> FEATURE:
<223> OTHER INFORMATION: Ara h3

<400> SEQUENCE: 19

Met Ala Lys Leu Leu Glu Leu Ser Phe Cys Phe Cys Phe Leu Val Leu
1               5                   10                  15

Gly Ala Ser Ser Ile Ser Phe Arg Gln Gln Pro Glu Glu Asn Ala Cys
            20                  25                  30

Gln Phe Gln Arg Leu Asn Ala Gln Arg Pro Asp Asn Arg Ile Glu Ser
        35                  40                  45

Glu Gly Gly Tyr Ile Glu Thr Trp Asn Pro Asn Asn Gln Glu Phe Glu
    50                  55                  60

Cys Ala Gly Val Ala Leu Ser Arg Leu Val Leu Arg Arg Asn Ala Leu
65                  70                  75                  80

Arg Arg Pro Phe Tyr Ser Asn Ala Pro Gln Glu Ile Phe Ile Gln Gln
                85                  90                  95

Gly Arg Gly Tyr Phe Gly Leu Ile Phe Pro Gly Cys Pro Ser Thr Tyr
            100                 105                 110

Glu Glu Pro Ala Gln Gln Gly Arg Arg Tyr Gln Ser Gln Arg Pro Pro
        115                 120                 125

Arg Arg Leu Gln Glu Glu Asp Gln Ser Gln Gln Gln Asp Ser His
        130                 135                 140

Gln Lys Val His Arg Phe Asn Glu Gly Asp Leu Ile Ala Val Pro Thr
145                 150                 155                 160

Gly Val Ala Phe Trp Leu Tyr Asn Asp His Asp Thr Asp Val Val Ala
                165                 170                 175

Val Ser Leu Thr Asp Thr Asn Asn Asn Asp Asn Gln Leu Asp Gln Phe
            180                 185                 190

Pro Arg Arg Phe Asn Leu Ala Gly Asn His Glu Gln Glu Phe Leu Arg
        195                 200                 205

Tyr Gln Gln Gln Ser Arg Gln Ser Arg Arg Ser Leu Pro Tyr Ser
    210                 215                 220

Pro Tyr Ser Pro His Ser Arg Pro Arg Arg Glu Glu Arg Glu Phe Arg
225                 230                 235                 240

Pro Arg Gly Gln His Ser Arg Arg Glu Arg Ala Gly Gln Glu Glu Glu
                245                 250                 255

Asp Glu Gly Gly Asn Ile Phe Ser Gly Phe Thr Pro Glu Phe Leu Glu
            260                 265                 270

Gln Ala Phe Gln Val Asp Asp Arg Gln Ile Val Gln Asn Leu Trp Gly
        275                 280                 285

Glu Asn Glu Ser Glu Glu Glu Gly Ala Ile Val Thr Val Arg Gly Gly
    290                 295                 300

Leu Arg Ile Leu Ser Pro Asp Gly Thr Arg Gly Ala Asp Glu Glu Glu
305                 310                 315                 320
```

```
Glu Tyr Asp Glu Asp Gln Tyr Glu Tyr His Glu Gln Asp Gly Arg
                325                 330                 335

Gly Arg Gly Ser Arg Gly Gly Asn Gly Ile Glu Glu Thr Ile Cys
            340                 345                 350

Thr Ala Cys Val Lys Lys Asn Ile Gly Gly Asn Arg Ser Pro His Ile
            355                 360                 365

Tyr Asp Pro Gln Arg Trp Phe Thr Gln Asn Cys His Asp Leu Asn Leu
    370                 375                 380

Leu Ile Leu Arg Trp Leu Gly Leu Ser Ala Glu Tyr Gly Asn Leu Tyr
385                 390                 395                 400

Arg Asn Ala Leu Phe Val Pro His Tyr Asn Thr Asn Ala His Ser Ile
                405                 410                 415

Ile Tyr Ala Leu Arg Gly Arg Ala His Val Gln Val Val Asp Ser Asn
                420                 425                 430

Gly Asn Arg Val Tyr Asp Glu Glu Leu Gln Glu Gly His Val Leu Val
            435                 440                 445

Val Pro Gln Asn Phe Ala Val Ala Gly Lys Ser Gln Ser Glu Asn Phe
    450                 455                 460

Glu Tyr Val Ala Phe Lys Thr Asp Ser Arg Pro Ser Ile Ala Asn Phe
465                 470                 475                 480

Ala Gly Glu Asn Ser Phe Ile Asp Asn Leu Pro Glu Glu Val Val Ala
                485                 490                 495

Asn Ser Tyr Gly Leu Pro Arg Glu Gln Ala Arg Gln Leu Lys Asn Asn
            500                 505                 510

Asn Pro Phe Lys Phe Phe Val Pro Pro Phe Gln Gln Ser Pro Arg Ala
        515                 520                 525

Val Ala
    530

<210> SEQ ID NO 20
<211> LENGTH: 129
<212> TYPE: PRT
<213> ORGANISM: artificial sequence
<220> FEATURE:
<223> OTHER INFORMATION: Ara h6

<400> SEQUENCE: 20

Ala His Ala Ser Ala Met Arg Arg Glu Arg Gly Arg Gln Gly Asp Ser
1               5                   10                  15

Ser Ser Cys Glu Arg Gln Val Asp Gly Val Asn Leu Lys Pro Cys Glu
                20                  25                  30

Gln His Ile Met Gln Arg Ile Met Gly Glu Gln Glu Gln Tyr Asp Ser
            35                  40                  45

Tyr Asn Phe Gly Ser Thr Arg Ser Ser Asp Gln Gln Gln Arg Cys Cys
    50                  55                  60

Asp Glu Leu Asn Glu Met Glu Asn Thr Gln Arg Cys Met Cys Glu Ala
65                  70                  75                  80

Leu Gln Gln Ile Met Glu Asn Gln Cys Asp Gly Leu Gln Asp Arg Gln
                85                  90                  95

Met Val Gln His Phe Lys Arg Glu Leu Met Asn Leu Pro Gln Gln Cys
            100                 105                 110

Asn Phe Gly Ala Pro Gln Arg Cys Asp Leu Asp Val Ser Gly Gly Arg
        115                 120                 125

Cys
```

<210> SEQ ID NO 21
<211> LENGTH: 501
<212> TYPE: DNA
<213> ORGANISM: artificial sequence
<220> FEATURE:
<223> OTHER INFORMATION: Arah2o2

<400> SEQUENCE: 21

```
atgggctgcc gccatcatca tcatcatcat ggcgcgcgcc agcgccagca gtgggaactg      60
cagggcgatc gtcgctgcca gagccagctg aacgcgcga acctgcgtcc gtgcgaacag     120
catctgatgc agaaaattca gcgcgatgaa gatagctatg ccgcgatcc gtatagccca     180
agccaagatc cgtatagccc aagccaggat ccggatcgcc gtgatccgta tagcccaagc     240
cgtatgatc gtcgcggcgc gggcagcagc cagcatcagg aacgctgctg caacgaactg     300
aacgaatttg aaacaacca cgctgcatg tgcgaaagcg cctgcaacagat tatgaaaaac     360
cagagcgatc gcctgcaagg ccgccagcaa gaacagcagt ttaaacgcga actgcgtaac     420
ctgccgcagc agtgcggcct gcgtgcgccg cagcgctgcg atctggaagt ggaaagcggc     480
ggccgtgatc gctattaata a                                              501
```

<210> SEQ ID NO 22
<211> LENGTH: 165
<212> TYPE: PRT
<213> ORGANISM: artificial sequence
<220> FEATURE:
<223> OTHER INFORMATION: Ara-h2o2 fusion protein

<400> SEQUENCE: 22

```
Met Gly Cys Arg His His His His His Gly Ala Arg Gln Arg Gln
1               5                   10                  15

Gln Trp Glu Leu Gln Gly Asp Arg Arg Cys Gln Ser Gln Leu Glu Arg
                20                  25                  30

Ala Asn Leu Arg Pro Cys Glu Gln His Leu Met Gln Lys Ile Gln Arg
            35                  40                  45

Asp Glu Asp Ser Tyr Gly Arg Asp Pro Tyr Ser Pro Ser Gln Asp Pro
50                  55                  60

Tyr Ser Pro Ser Gln Asp Pro Arg Arg Asp Pro Tyr Ser Pro Ser
65                  70                  75                  80

Pro Tyr Asp Arg Arg Gly Ala Gly Ser Ser Gln His Gln Glu Arg Cys
                85                  90                  95

Cys Asn Glu Leu Asn Glu Phe Glu Asn Asn Gln Arg Cys Met Cys Glu
            100                 105                 110

Ala Leu Gln Gln Ile Met Glu Asn Gln Ser Asp Arg Leu Gln Gly Arg
        115                 120                 125

Gln Gln Glu Gln Gln Phe Lys Arg Glu Leu Arg Asn Leu Pro Gln Gln
    130                 135                 140

Cys Gly Leu Arg Ala Pro Gln Arg Cys Asp Leu Glu Val Glu Ser Gly
145                 150                 155                 160

Gly Arg Asp Arg Tyr
                165
```

<210> SEQ ID NO 23
<211> LENGTH: 27
<212> TYPE: PRT
<213> ORGANISM: artificial Sequence
<220> FEATURE:
<223> OTHER INFORMATION: aa 2-28 of SEQ ID NO:1

-continued

```
<400> SEQUENCE: 23

Asp Lys Ser Glu Ser Thr Ser Ala Gly Arg Ser Arg Arg Arg Pro
1               5                   10                  15

Arg Arg Gly Ser Arg Ser Ala Pro Ser Ser Ala
            20                  25

<210> SEQ ID NO 24
<211> LENGTH: 10
<212> TYPE: DNA
<213> ORGANISM: artificial sequence
<220> FEATURE:
<223> OTHER INFORMATION: palindromic CpG

<400> SEQUENCE: 24
gacgatcgtc                                                          10

<210> SEQ ID NO 25
<211> LENGTH: 135
<212> TYPE: PRT
<213> ORGANISM: artificial sequence
<220> FEATURE:
<223> OTHER INFORMATION: Ara-h201

<400> SEQUENCE: 25

Arg Gln Gln Trp Glu Leu Gln Gly Asp Arg Arg Cys Gln Ser Gln Leu
1               5                   10                  15

Glu Arg Ala Asn Leu Arg Pro Cys Glu Gln His Leu Met Gln Lys Ile
            20                  25                  30

Gln Arg Asp Glu Asp Ser Tyr Glu Arg Asp Pro Tyr Ser Pro Ser Gln
        35                  40                  45

Asp Pro Tyr Ser Pro Ser Pro Tyr Asp Arg Arg Gly Ala Gly Ser Ser
    50                  55                  60

Gln His Gln Glu Arg Cys Cys Asn Glu Leu Asn Glu Phe Glu Asn Asn
65                  70                  75                  80

Gln Arg Cys Met Cys Glu Ala Leu Gln Gln Ile Met Glu Asn Gln Ser
                85                  90                  95

Asp Arg Leu Gln Gly Arg Gln Gln Glu Gln Gln Phe Lys Arg Glu Leu
            100                 105                 110

Arg Asn Leu Pro Gln Gln Cys Gly Leu Arg Ala Pro Gln Arg Cys Asp
        115                 120                 125

Leu Asp Val Glu Ser Gly Gly
    130                 135

<210> SEQ ID NO 26
<211> LENGTH: 144
<212> TYPE: PRT
<213> ORGANISM: artificial sequence
<220> FEATURE:
<223> OTHER INFORMATION: Ara h6*

<400> SEQUENCE: 26

Ala Lys Ser Thr Ile Leu Val Ala Leu Leu Ala Leu Val Leu Val Ala
1               5                   10                  15

His Ala Ser Ala Met Arg Arg Glu Arg Gly Arg Gln Gly Asp Ser Ser
            20                  25                  30

Ser Cys Glu Arg Gln Val Asp Arg Val Asn Leu Lys Pro Cys Glu Gln
        35                  40                  45

His Ile Met Gln Arg Ile Met Gly Glu Gln Glu Gln Tyr Asp Ser Tyr
    50                  55                  60
```

```
Asp Ile Arg Ser Thr Arg Ser Ser Asp Gln Gln Arg Cys Cys Asp
 65                  70                  75                  80

Glu Leu Asn Glu Met Glu Asn Thr Gln Arg Cys Met Cys Glu Ala Leu
                 85                  90                  95

Gln Gln Ile Met Glu Asn Gln Cys Asp Arg Leu Gln Asp Arg Gln Met
            100                 105                 110

Val Gln Gln Phe Lys Arg Glu Leu Met Asn Leu Pro Gln Gln Cys Asn
        115                 120                 125

Phe Arg Ala Pro Gln Arg Cys Asp Leu Asp Val Ser Gly Gly Arg Cys
    130                 135                 140

<210> SEQ ID NO 27
<211> LENGTH: 601
<212> TYPE: PRT
<213> ORGANISM: artificial sequence
<220> FEATURE:
<223> OTHER INFORMATION: Ara h1 mature protein

<400> SEQUENCE: 27

Lys Ser Ser Pro Tyr Gln Lys Lys Thr Glu Asn Pro Cys Ala Gln Arg
 1               5                  10                  15

Cys Leu Gln Ser Cys Gln Glu Pro Asp Asp Leu Lys Gln Lys Ala
             20                  25                  30

Cys Glu Ser Arg Cys Thr Lys Leu Glu Tyr Asp Pro Arg Cys Val Tyr
             35                  40                  45

Asp Pro Arg Gly His Thr Gly Thr Thr Asn Gln Arg Ser Pro Pro Gly
     50                  55                  60

Glu Arg Thr Arg Gly Arg Gln Pro Gly Asp Tyr Asp Asp Arg Arg
 65                  70                  75                  80

Gln Pro Arg Arg Glu Glu Gly Gly Arg Trp Gly Pro Ala Gly Pro Arg
                 85                  90                  95

Glu Arg Glu Arg Glu Glu Asp Trp Arg Gln Pro Arg Glu Asp Trp Arg
            100                 105                 110

Arg Pro Ser His Gln Gln Pro Arg Lys Ile Arg Pro Glu Gly Arg Glu
        115                 120                 125

Gly Glu Gln Glu Trp Gly Thr Pro Gly Ser His Val Arg Glu Glu Thr
    130                 135                 140

Ser Arg Asn Asn Pro Phe Tyr Phe Pro Ser Arg Arg Phe Ser Thr Arg
145                 150                 155                 160

Tyr Gly Asn Gln Asn Gly Arg Ile Arg Val Leu Gln Arg Phe Asp Gln
                165                 170                 175

Arg Ser Arg Gln Phe Gln Asn Leu Gln Asn His Arg Ile Val Gln Ile
            180                 185                 190

Glu Ala Lys Pro Asn Thr Leu Val Leu Pro Lys His Ala Asp Ala Asp
        195                 200                 205

Asn Ile Leu Val Ile Gln Gln Gly Gln Ala Thr Val Thr Val Ala Asn
    210                 215                 220

Gly Asn Asn Arg Lys Ser Phe Asn Leu Asp Glu Gly His Ala Leu Arg
225                 230                 235                 240

Ile Pro Ser Gly Phe Ile Ser Tyr Ile Leu Asn Arg His Asp Asn Gln
                245                 250                 255

Asn Leu Arg Val Ala Lys Ile Ser Met Pro Val Asn Thr Pro Gly Gln
            260                 265                 270

Phe Glu Asp Phe Phe Pro Ala Ser Ser Arg Asp Gln Ser Ser Tyr Leu
        275                 280                 285
```

```
Gln Gly Phe Ser Arg Asn Thr Leu Glu Ala Ala Phe Asn Ala Glu Phe
        290                 295                 300
Asn Glu Ile Arg Arg Val Leu Leu Glu Glu Asn Ala Gly Gly Glu Gln
305                 310                 315                 320
Glu Glu Arg Gly Gln Arg Arg Trp Ser Thr Arg Ser Ser Glu Asn Asn
                325                 330                 335
Glu Gly Val Ile Val Lys Val Ser Lys Glu His Val Glu Glu Leu Thr
            340                 345                 350
Lys His Ala Lys Ser Val Ser Lys Gly Ser Glu Glu Glu Gly Asp
        355                 360                 365
Ile Thr Asn Pro Ile Asn Leu Arg Glu Gly Glu Pro Asp Leu Ser Asn
370                 375                 380
Asn Phe Gly Lys Leu Phe Glu Val Lys Pro Asp Lys Asn Pro Gln
385                 390                 395                 400
Leu Gln Asp Leu Asp Met Met Leu Thr Cys Val Glu Ile Lys Glu Gly
                405                 410                 415
Ala Leu Met Leu Pro His Phe Asn Ser Lys Ala Met Val Ile Val Val
            420                 425                 430
Val Asn Lys Gly Thr Gly Asn Leu Glu Leu Val Ala Val Arg Lys Glu
        435                 440                 445
Gln Gln Gln Arg Gly Arg Arg Glu Glu Glu Asp Glu Asp Glu Glu
    450                 455                 460
Glu Glu Gly Ser Asn Arg Glu Val Arg Arg Tyr Thr Ala Arg Leu Lys
465                 470                 475                 480
Glu Gly Asp Val Phe Ile Met Pro Ala Ala His Pro Val Ala Ile Asn
                485                 490                 495
Ala Ser Ser Glu Leu His Leu Leu Gly Phe Gly Ile Asn Ala Glu Asn
            500                 505                 510
Asn His Arg Ile Phe Leu Ala Gly Asp Lys Asp Asn Val Ile Asp Gln
        515                 520                 525
Ile Glu Lys Gln Ala Lys Asp Leu Ala Phe Pro Gly Ser Gly Glu Gln
    530                 535                 540
Val Glu Lys Leu Ile Lys Asn Gln Lys Glu Ser His Phe Val Ser Ala
545                 550                 555                 560
Arg Pro Gln Ser Gln Ser Gln Ser Pro Ser Ser Pro Glu Lys Glu Ser
                565                 570                 575
Pro Glu Lys Glu Asp Gln Glu Glu Glu Asn Gln Gly Gly Lys Gly Pro
            580                 585                 590
Leu Leu Ser Ile Leu Lys Ala Phe Asn
        595                 600

<210> SEQ ID NO 28
<211> LENGTH: 511
<212> TYPE: PRT
<213> ORGANISM: artificial sequence
<220> FEATURE:
<223> OTHER INFORMATION: Ara h3*

<400> SEQUENCE: 28

Met Ala Lys Leu Leu Ala Leu Ser Leu Cys Phe Cys Val Leu Val Leu
1               5                   10                  15
Gly Ala Ser Ser Val Thr Phe Arg Gln Gly Gly Glu Glu Asn Glu Cys
            20                  25                  30
Gln Phe Gln Arg Leu Asn Ala Gln Arg Pro Asp Asn Arg Ile Glu Ser
        35                  40                  45
```

-continued

```
Glu Gly Gly Tyr Ile Glu Thr Trp Asn Pro Asn Gln Glu Phe Gln
    50              55              60
Cys Ala Gly Val Ala Leu Ser Arg Thr Val Leu Arg Arg Asn Ala Leu
 65              70              75              80
Arg Arg Pro Phe Tyr Ser Asn Ala Pro Leu Glu Ile Tyr Val Gln Gln
                85              90              95
Gly Ser Gly Tyr Phe Gly Leu Ile Phe Pro Gly Cys Pro Ser Thr Tyr
            100             105             110
Glu Glu Pro Ala Gln Glu Gly Arg Arg Tyr Gln Ser Gln Lys Pro Ser
            115             120             125
Arg Arg Phe Gln Val Gly Gln Asp Asp Pro Ser Gln Gln Gln Gln Asp
    130             135             140
Ser His Gln Lys Val His Arg Phe Asp Glu Gly Asp Leu Ile Ala Val
145             150             155             160
Pro Thr Gly Val Ala Phe Trp Met Tyr Asn Asp Glu Asp Thr Asp Val
                165             170             175
Val Thr Val Thr Leu Ser Asp Thr Ser Ser Ile His Asn Gln Leu Asp
            180             185             190
Gln Phe Pro Arg Arg Phe Tyr Leu Ala Gly Asn Gln Glu Gln Glu Phe
            195             200             205
Leu Arg Tyr Gln Gln Gln Gln Gly Ser Arg Pro His Tyr Arg Gln Ile
    210             215             220
Ser Pro Arg Val Arg Gly Asp Glu Gln Glu Asn Glu Gly Ser Asn Ile
225             230             235             240
Phe Ser Gly Phe Ala Gln Glu Phe Leu Gln His Ala Phe Gln Val Asp
                245             250             255
Arg Gln Thr Val Glu Asn Leu Arg Gly Glu Asn Glu Arg Glu Glu Gln
            260             265             270
Gly Ala Ile Val Thr Val Lys Gly Gly Leu Arg Ile Leu Ser Pro Asp
    275             280             285
Glu Glu Asp Glu Ser Ser Arg Ser Pro Pro Asn Arg Arg Glu Glu Phe
290             295             300
Asp Glu Asp Arg Ser Arg Pro Gln Gln Arg Gly Lys Tyr Asp Glu Asn
305             310             315             320
Arg Arg Gly Tyr Lys Asn Gly Ile Glu Glu Thr Ile Cys Ser Ala Ser
                325             330             335
Val Lys Lys Asn Leu Gly Arg Ser Asn Pro Asp Ile Asn Pro Gln
            340             345             350
Ala Gly Ser Leu Arg Ser Val Asn Glu Leu Asp Leu Pro Ile Leu Gly
            355             360             365
Trp Leu Gly Leu Ser Ala Gln His Gly Thr Ile Tyr Arg Asn Ala Met
    370             375             380
Phe Val Pro His Tyr Thr Leu Asn Ala His Thr Ile Val Val Ala Leu
385             390             395             400
Asn Gly Arg Ala His Val Gln Val Val Asp Ser Asn Gly Asn Arg Val
                405             410             415
Tyr Asp Glu Glu Leu Gln Glu Gly His Val Leu Val Val Pro Gln Asn
            420             425             430
Phe Ala Val Ala Ala Lys Ala Gln Ser Glu Asn Tyr Glu Tyr Leu Ala
            435             440             445
Phe Lys Thr Asp Ser Arg Pro Ser Ile Ala Asn Gln Ala Gly Glu Asn
    450             455             460
```

Ser Ile Ile Asp Asn Leu Pro Glu Glu Val Val Ala Asn Ser Tyr Arg
465                 470                 475                 480

Leu Pro Arg Glu Gln Ala Arg Gln Leu Lys Asn Asn Asn Pro Phe Lys
            485                 490                 495

Phe Phe Val Pro Pro Phe Asp His Gln Ser Met Arg Glu Val Ala
        500                 505                 510

<210> SEQ ID NO 29
<211> LENGTH: 499
<212> TYPE: DNA
<213> ORGANISM: Artificial Sequence
<220> FEATURE:
<223> OTHER INFORMATION: Ara-h202-nhk gene

<400> SEQUENCE: 29
catatgaatc ataaagtgcg ccagcagtgg gaactgcagg gcgatcgtcg ctgccagagc    60
cagctggaac gcgcgaacct gcgtccgtgc gaacagcatc tgatgcagaa aattcagcgc   120
gatgaagata gctatggccg cgatccgtat agcccaagcc aagatccgta tagcccaagc   180
caggatccgg atcgccgtga tccgtatagc ccaagcccgt atgatcgtcg cggcgcgggc   240
agcagccagc atcaggaacg ctgctgcaac gaactgaacg aatttgaaaa caaccagcgc   300
tgcatgtgcg aagcgctgca acagattatg gaaaaccaga gcgatcgcct gcaaggccgc   360
cagcaagaac agcagtttaa acgcgaactg cgtaacctgc cgcagcagtg cggcctgcgt   420
gcgccgcagc gctgcgatct ggaagtggaa agcggcggcc gtgatcgcta tggtggttgt   480
ggataataag cttctcgag                                                499

<210> SEQ ID NO 30
<211> LENGTH: 160
<212> TYPE: PRT
<213> ORGANISM: Artificial Sequence
<220> FEATURE:
<223> OTHER INFORMATION: Ara-h-202-nhk protein

<400> SEQUENCE: 30

Met Asn His Lys Val Arg Gln Gln Trp Glu Leu Gln Gly Asp Arg Arg
1               5                   10                  15

Cys Gln Ser Gln Leu Glu Arg Ala Asn Leu Arg Pro Cys Glu Gln His
            20                  25                  30

Leu Met Gln Lys Ile Gln Arg Asp Glu Asp Ser Tyr Gly Arg Asp Pro
        35                  40                  45

Tyr Ser Pro Ser Gln Asp Pro Tyr Ser Pro Ser Gln Asp Pro Asp Arg
    50                  55                  60

Arg Asp Pro Tyr Ser Pro Ser Pro Tyr Asp Arg Arg Gly Ala Gly Ser
65                  70                  75                  80

Ser Gln His Gln Glu Arg Cys Cys Asn Glu Leu Asn Glu Phe Glu Asn
                85                  90                  95

Asn Gln Arg Cys Met Cys Glu Ala Leu Gln Gln Ile Met Glu Asn Gln
            100                 105                 110

Ser Asp Arg Leu Gln Gly Arg Gln Gln Glu Gln Phe Lys Arg Glu
        115                 120                 125

Leu Arg Asn Leu Pro Gln Gln Cys Gly Leu Arg Ala Pro Gln Arg Cys
    130                 135                 140

Asp Leu Glu Val Glu Ser Gly Gly Arg Asp Arg Tyr Gly Gly Cys Gly
145                 150                 155                 160

-continued

```
<210> SEQ ID NO 31
<211> LENGTH: 41
<212> TYPE: DNA
<213> ORGANISM: Artificial Sequence
<220> FEATURE:
<223> OTHER INFORMATION: Ara-h202-nhkF

<400> SEQUENCE: 31
acacatatga atcataaagt gcgccagcag tgggaactgc a                    41

<210> SEQ ID NO 32
<211> LENGTH: 51
<212> TYPE: DNA
<213> ORGANISM: Artificial Sequence
<220> FEATURE:
<223> OTHER INFORMATION: Ara-h2-cgR

<400> SEQUENCE: 32
tgctcgagaa gcttattatc cacaaccacc atagcgatca cggccgccgc t         51
```